(12) United States Patent
Katz et al.

(10) Patent No.: US 6,627,427 B1
(45) Date of Patent: Sep. 30, 2003

(54) HETEROLOGOUS PRODUCTION OF 15-METHYL-6-DEOXYERTHRONOLIDE B

(75) Inventors: Leonard Katz, Oakland, CA (US); Peter Revill, Oakland, CA (US)

(73) Assignee: Kosan Biosciences, Inc., Hayward, CA (US)

( * ) Notice: Subject to any disclaimer, the term of this patent is extended or adjusted under 35 U.S.C. 154(b) by 0 days.

(21) Appl. No.: 09/697,022

(22) Filed: Oct. 25, 2000

Related U.S. Application Data

(60) Provisional application No. 60/161,414, filed on Oct. 25, 1999.

(51) Int. Cl.[7] .................................................. C12N 1/20
(52) U.S. Cl. ......................................................... 435/252.3
(58) Field of Search ............................... 435/252.3, 325, 435/419, 254.11

(56) References Cited

U.S. PATENT DOCUMENTS

| | | | |
|---|---|---|---|
| 5,672,491 A | | 9/1997 | Khosla et al. |
| 5,962,290 A | | 10/1999 | Khosla et al. |
| 6,033,883 A | | 3/2000 | Barr et al. |
| 6,066,721 A | | 5/2000 | Khosla et al. |
| 6,080,555 A | | 6/2000 | Khosla et al. |
| 6,262,340 B1 | * | 7/2001 | Betlach et al. |
| 6,303,342 B1 | * | 10/2001 | Julien et al. |

FOREIGN PATENT DOCUMENTS

| | | |
|---|---|---|
| WO | WO 97/13845 | 4/1997 |
| WO | WO 98/49315 | 11/1998 |
| WO | WO 99/02669 | 1/1999 |
| WO | WO 99/03986 | 1/1999 |
| WO | WO 01/27306 | 4/2001 |
| WO | WO 01/31035 | 5/2001 |

OTHER PUBLICATIONS

Kealey et al. Production of a polyketide natural product in a nonpolyketide-producing prokaryotic and eukaryotic hosts. PNAS (1998) 95:505–509.*

Kao et al. Engineered Biosynthesis of a Complete Macrolactone in a Heterologous Host. Science (1994) 365:509–512.*

Tuchman et al. Enhanced Production of Arginine and Urea by Genetically Engineered *Escherichia coli* K–12 Strains. Applied and Environmental Microbiology (1997) 63(1):33–38.*

Wawszkiewicz et al. Propionyl–CoA* Dependent H14CO3–Exchange into Methylmalonyl–CoA in Extracts of *Streptomyces erythraeus*. Biochemische Zeitschrift (1964) 240:213–227.*

Gokhale et al. Dissecting and Exploiting Intermodular Communication in Polyketide Synthases. Science (1999) 284:482–485.*

Hsieh and Kolattukudy, "Inhibition of Erythromycin Synthesis by Disrtuption of Malonyl–Coenzyme A Decarboxylase Gene eryM in *Saccharopolyspora erythraea*" J. Bact. (1994) 176(3):714–724.

Donadio et al., Molecular Microbiology (1996) 19(5):977–984.

(List continued on next page.)

*Primary Examiner*—Ponnathapu Achutamurthy
*Assistant Examiner*—Kathleen Kerr
(74) *Attorney, Agent, or Firm*—Morrison & Foerster LLP; Kevin Kaster

(57) ABSTRACT

Recombinant host cells that comprise recombinant DNA expression vectors that drive expression of a product and a precursor for biosynthesis of that product can be used to produce useful products such as polyketides in host cells that do not naturally produce the product or produce the product at low levels due to the absence of the precursor or the presence of the precursor in rate limiting amounts.

12 Claims, 20 Drawing Sheets

OTHER PUBLICATIONS

Khosla et al., Annual Review of Biochemistry (1999) 68:219–253.
Kuhstoss et al., Gene (1996) 183:231–236.
Liu et al., Metabolic Engineering (2001) 3(1):40–48.
Pfeifer et al., Microbiology and Molecular Biology (2001) 65(1):106–118.
Pieper et al., Biochemistry (1996) 35(7):2054–2060.
Stassi et al., PNAS USA (1998) 95(13):7305–7309.
Tang et al., Journal of Bacteriology (1994) 176(19):6107–6119.
Vrijbloed et al., Journal of Bacteriology (1999) 181(18):5600–5605.
Wallace et al., European Journal of Biochemistry (1995) 233(3):954–962.
Xue et al., PNAS USA (1999) 96(21):11740–11745.

* cited by examiner

```
gatctggatg tcgaagccgg gacggagcgg gatgacggcg tcagcggcgt cttccatgtg    60
gaactcctta tccggacgac tcgacctggt tggctaagcg gagattaggt ctgcgcgcgc   120
gaaaccgccc agcggagcgc cgagatcctc acctgatcag gtaaggatct tcattcgatg   180
tcatgtagcc agatttcggc tgaactggtc cacgatcccg attcgtgacc atgcgtgtcc   240
actttggagc gggtgcgttc gttcggccta gtggcgtgct ccgcggtgat caagtgttag   300
gttagcctca gctcagcggg gtcgacggat ggagtgaacg gc gtg gcg ggc gac      354
                                              Val Ala Gly Asp
                                                           1
```

```
gtg gaa ctc gcg gac agg gct cga cga cgc gcg tgc cgg ctg ctc agg    402
Val Glu Leu Ala Asp Arg Ala Arg Arg Arg Ala Cys Arg Leu Leu Arg
 5              10                  15                  20
         XbaI
cgt tgg ctg gcc gag acg cac act ccg gtg gag ccc ggc ccg ctg tcc    450
Arg Trp Leu Ala Glu Thr His Thr Pro Val Glu Pro Gly Pro Leu Ser
            25                  30                  35 ctg cgg atc ggc ccg gtg cgg gtg tcg gcc gag gtc gct tac cgc tcg    498
Leu Arg Ile Gly Pro Val Arg Val Ser Ala Glu Val Ala Tyr Arg Ser
                40                  45                  50 ccg acg ggc gcc cac ggg ttc ggc ccg atc cgc gtc ctc gat gcc gag    546
Pro Thr Gly Ala His Gly Phe Gly Pro Ile Arg Val Leu Asp Ala Glu
            55                  60                  65 ggt gtg ccg gtg gcg ctc gcc gat ccg gtg ctg ctg gcg gcc gcc tgc    594
Gly Val Pro Val Ala Leu Ala Asp Pro Val Leu Leu Ala Ala Ala Cys
 70              75                  80 tcg gcg gac tcg cgg agc cgc tcg ctg ccg agc gcg ccg atc aac gcc    642
Ser Ala Asp Ser Arg Ser Arg Ser Leu Pro Ser Ala Pro Ile Asn Ala
 85              90                  95                 100 ccg gac gcc ggt acc gct gtc gac tgg gtg ctc tcg tcg ctc gcc gac    690
Pro Asp Ala Gly Thr Ala Val Asp Trp Val Leu Ser Ser Leu Ala Asp
                105                 110                 115 gac gag gac gac gag gtg ccc gcc ggc atg acc gcg gag gag gcg gtg    738
Asp Glu Asp Asp Glu Val Pro Ala Gly Met Thr Ala Glu Glu Ala Val
            120                 125                 130 cgc ctg ctg tcg cgg cag gtc gac gac ctg ccg cgg tcg ccg ggc gcc    786
Arg Leu Leu Ser Arg Gln Val Asp Asp Leu Pro Arg Ser Pro Gly Ala
                135                 140                 145 gac ccg tgg tcg ctg gtc gcc ggc ccg ctg gcg gcc atc ggg cgg ttc    834
Asp Pro Trp Ser Leu Val Ala Gly Pro Leu Ala Ala Ile Gly Arg Phe
        150                 155                 160 ggg cgg gcc ggg atc gcc gac gag tgc tgg ttg ctg gag gtg ctc gcc    882
Gly Arg Ala Gly Ile Ala Asp Glu Cys Trp Leu Leu Glu Val Leu Ala
165                 170                 175                 180
```

Figure 3 A

```
ggg cgg ctc cgc gcg gtc gac gac gac ctg tcc cgc tcg tgg ctg agc    930
Gly Arg Leu Arg Ala Val Asp Asp Asp Leu Ser Arg Ser Trp Leu Ser
                185                 190                 195 agt ccg acg ctc gcc gac cgc gct gtg ctc gtg ggt gag ggg ttg cgc    978
Ser Pro Thr Leu Ala Asp Arg Ala Val Leu Val Gly Glu Gly Leu Arg
            200                 205                 210 tac cgg ccg gat gtg cgg ccg gtg ccg ttc gac gtg ccg aac ccg ctg   1026
Tyr Arg Pro Asp Val Arg Pro Val Pro Phe Asp Val Pro Asn Pro Leu
        215                 220                 225 cac gag ggc aag tcc gac gtc ccg ccg ccg ccc gtg ccc gtg ctg ggc   1074
His Glu Gly Lys Ser Asp Val Pro Pro Pro Pro Val Pro Val Leu Gly
    230                 235                 240 ggg ccg tgg tcg ctg cgt ccg gtc gag gtc gcg gtc cac ggg gat ggc   1122
Gly Pro Trp Ser Leu Arg Pro Val Glu Val Ala Val His Gly Asp Gly
245                 250                 255                 260 ggg cct gac gtc gca ctg gtg cac cgc tgg atg aac acc ccg cac gtc   1170
Gly Pro Asp Val Ala Leu Val His Arg Trp Met Asn Thr Pro His Val
                265                 270                 275 gcg cac cac tgg aac cag gcg tgg ccg ctg gag cgc tgg cgg gag gaa   1218
Ala His His Trp Asn Gln Ala Trp Pro Leu Glu Arg Trp Arg Glu Glu
            280                 285                 290 ctc gcc cac cag ctc ggc ggt gag cac tcc ctg ccc tgc gtg gtc gga   1266
Leu Ala His Gln Leu Gly Gly Glu His Ser Leu Pro Cys Val Val Gly
        295                 300                 305 cac gag gga cgc gag gtc gcg tat ctg gag ctc tac cgg gtg acc cgc   1314
His Glu Gly Arg Glu Val Ala Tyr Leu Glu Leu Tyr Arg Val Thr Arg
    310                 315                 320
        HindIII
gac aag ctt gcg ggc tgc tac ccg tac ggg ccg cac gac ctc ggg gtc   1362
Asp Lys Leu Ala Gly Cys Tyr Pro Tyr Gly Pro His Asp Leu Gly Val
325                 330                 335                 340 cac atc gcg atc ggc gag cgg gag gtg ctc ggg cgc ggt ttc ggg tcg   1410
His Ile Ala Ile Gly Glu Arg Glu Val Leu Gly Arg Gly Phe Gly Ser
                345                 350                 355 tcg ctg ctg cgc gcg gtc gcg ggt gcg ctg ctg gac gcc gat ccg cgg   1458
Ser Leu Leu Arg Ala Val Ala Gly Ala Leu Leu Asp Ala Asp Pro Arg
            360                 365                 370 tgc gcg cgg gtg gtc gcc gag ccg aat gtg cac aac gag gct tcg gtg   1506
Cys Ala Arg Val Val Ala Glu Pro Asn Val His Asn Glu Ala Ser Val
        375                 380                 385
```

Figure 3 B

```
cgc gcc ttc gcc aag gcc ggg ttc gtc cgg gag agg gag atc ggc ctg   1554
Arg Ala Phe Ala Lys Ala Gly Phe Val Arg Glu Arg Glu Ile Gly Leu
    390                 395                 400 ccc gcc aag aac tcg gct ctg atg gtc ttc tcc cgg gtc t gacgaccggt  1604
Pro Ala Lys Asn Ser Ala Leu Met Val Phe Ser Arg Val (SEQ ID NO:2)
405                 410                 415 catgcccctg tgtgaacgcg tgagtaagcg caccgtgacg tgatcccccg cttgaaccaa 1664
ggttagcctt actttattg gtggagaacg atgccggagc gctccgccgt gtcgttgccg  1724
ctgaccacag cgcagtaggg catctggttc gcccagcaac tcgaccggac gaacccgatc 1784
tacaacaccg gcgagtgcgt cgagatcagc ggcccggtgg agccggtggt gttcgagcag 1844
gccctgcggt ggggcgtggc ggaggccgag gcgctgcgag cccgcgtggt cgtcgacggc 1904
gacgagccgc gccaggtcgt ggagccggag gtggacttcc cgctgccgtg ctcgacgtca 1964
gcgccgaggc ggaccc (SEQ ID NO:1)                                  1980
```

Figure 3 C

Met His Val Pro Gly Glu Glu Asn Gly His Ser Ile Ala Ile Val Gly
1           5                   10                  15
Ile Ala Cys Arg Leu Pro Gly Ser Ala Thr Pro Gln Glu Phe Trp Arg
            20                  25                  30
Leu Leu Ala Asp Ser Ala Asp Ala Leu Asp Glu Pro Pro Ala Gly Arg
            35                  40                  45
Phe Pro Thr Gly Ser Leu Ser Ser Pro Pro Ala Pro Arg Gly Gly Phe
    50                  55                  60
Leu Asp Ser Ile Asp Thr Phe Asp Ala Asp Phe Phe Asn Ile Ser Pro
65                  70                  75                  80
Arg Glu Ala Gly Val Leu Asp Pro Gln Gln Arg Leu Ala Leu Glu Leu
            85                  90                  95
Gly Trp Glu Ala Leu Glu Asp Ala Gly Ile Val Pro Arg His Leu Arg
            100                 105                 110
Gly Thr Arg Thr Ser Val Phe Met Gly Ala Met Trp Asp Asp Tyr Ala
            115                 120                 125
His Leu Ala His Ala Arg Gly Glu Ala Ala Leu Thr Arg His Ser Leu
    130                 135                 140
Thr Gly Thr His Arg Gly Met Ile Ala Asn Arg Leu Ser Tyr Ala Leu
145                 150                 155                 160
Gly Leu Gln Gly Pro Ser Leu Thr Val Asp Thr Gly Gln Ser Ser Ser
            165                 170                 175
Leu Ala Ala Val His Met Ala Cys Glu Ser Leu Ala Arg Gly Glu Ser
            180                 185                 190
Asp Leu Ala Leu Val Gly Gly Val Asn Leu Val Leu Asp Pro Ala Gly
            195                 200                 205
Thr Thr Gly Val Glu Arg Phe Gly Ala Leu Ser Pro Asp Gly Arg Cys
210                 215                 220
Tyr Thr Phe Asp Ser Arg Ala Asn Gly Tyr Ala Arg Gly Glu Gly Gly
225                 230                 235                 240
Val Val Val Val Leu Lys Pro Thr His Arg Ala Leu Ala Asp Gly Asp
            245                 250                 255
Thr Val Tyr Cys Glu Ile Leu Gly Ser Ala Leu Asn Asn Asp Gly Ala
            260                 265                 270
Thr Glu Gly Leu Thr Val Pro Ser Ala Arg Ala Gln Ala Asp Val Leu
    275                 280                 285
Arg Gln Ala Trp Glu Arg Ala Arg Val Ala Pro Thr Asp Val Gln Tyr
    290                 295                 300
Val Glu Leu His Gly Thr Gly Thr Pro Ala Gly Asp Pro Val Glu Ala
305                 310                 315                 320
Glu Gly Leu Gly Thr Ala Leu Gly Thr Ala Arg Pro Ala Glu Ala Pro
            325                 330                 335
Leu Leu Val Gly Ser Val Lys Thr Asn Ile Gly His Leu Glu Gly Ala
            340                 345                 350
Ala Gly Ile Ala Gly Leu Leu Lys Thr Val Leu Ser Ile Lys Asn Arg
            355                 360                 365
His Leu Pro Ala Ser Leu Asn Phe Thr Ser Pro Asn Pro Arg Ile Asp
    370                 375                 380
Leu Asp Ala Leu Arg Leu Arg Val His Thr Ala Tyr Gly Pro Trp Pro
385                 390                 395                 400
Ser Pro Asp Arg Pro Leu Val Ala Gly Val Ser Ser Phe Gly Met Gly
            405                 410                 415

Figure 10 A

```
Gly Thr Asn Cys His Val Val Leu Ser Glu Leu Arg Asn Ala Gly Gly
            420                 425                 430
Asp Gly Ala Gly Lys Gly Pro Tyr Thr Gly Thr Glu Asp Arg Leu Gly
        435                 440                 445
Ala Thr Glu Ala Glu Lys Arg Pro Asp Pro Ala Thr Gly Asn Gly Pro
    450                 455                 460
Asp Pro Ala Gln Asp Thr His Arg Tyr Pro Pro Leu Ile Leu Ser Ala
465                 470                 475                 480
Arg Ser Asp Ala Ala Leu Arg Ala Gln Ala Glu Arg Leu Arg His His
                485                 490                 495
Leu Glu His Ser Pro Gly Gln Arg Leu Arg Asp Thr Ala Tyr Ser Leu
            500                 505                 510
Ala Thr Arg Arg Gln Val Phe Glu Arg His Ala Val Val Thr Gly His
        515                 520                 525
Asp Arg Glu Asp Leu Leu Asn Gly Leu Arg Asp Leu Glu Asn Gly Leu
    530                 535                 540
Pro Ala Pro Gln Val Leu Leu Gly Arg Thr Pro Thr Pro Glu Pro Gly
545                 550                 555                 560
Gly Leu Val Phe Val Phe Pro Gly Gln Gly Pro Gln Trp Arg Gly Met
                565                 570                 575
Gly Val Glu Leu Met Ala Ala Ser Pro Val Phe Ala Ala Arg Met Arg
            580                 585                 590
Gln Cys Ala Asp Ala Leu Ile Pro His Thr Gly Trp Asp Pro Ile Ala
        595                 600                 605
Met Leu Asp Asp Pro Glu Val Thr Arg Arg Val Asp Val Val His Pro
    610                 615                 620
Val Cys Trp Ala Val Met Val Ser Leu Ala Ala Val Trp Glu Ala Ala
625                 630                 635                 640
Gly Val Arg Pro Asp Ala Val Ile Gly His Ser Gln Gly Glu Ile Ala
                645                 650                 655
Ala Ala Cys Val Ala Gly Ala Leu Thr Leu Glu Asp Gly Ala Arg Leu
            660                 665                 670
Val Ala Leu Arg Ser Val Leu Leu Leu Arg Glu Leu Ala Gly Arg
        675                 680                 685
Gly Ala Met Gly Ser Val Ala Leu Pro Ala Ala Asp Val Glu Ala Asp
    690                 695                 700
Ala Ala Arg Ile Asp Gly Val Trp Val Ala Gly Arg Asn Gly Ala Thr
705                 710                 715                 720
Thr Thr Thr Val Ala Gly Arg Pro Asp Ala Val Glu Thr Leu Ile Ala
                725                 730                 735
Asp Tyr Glu Ala Arg Gly Val Trp Val Arg Arg Ile Ala Val Asp Cys
            740                 745                 750
Pro Thr His Thr Pro Phe Val Asp Pro Leu Tyr Asp Glu Leu Gln Arg
        755                 760                 765
Ile Val Ala Asp Thr Thr Ser Arg Thr Pro Glu Ile Pro Trp Phe Ser
    770                 775                 780
Thr Ala Asp Glu Arg Trp Ile Asp Ala Pro Leu Asp Asp Glu Tyr Trp
785                 790                 795                 800
Phe Arg Asn Met Arg His Pro Val Gly Phe Ala Thr Ala Val Thr Ala
                805                 810                 815
Ala Arg Glu Pro Gly Asp Thr Val Phe Val Glu Val Ser Ala His Pro
            820                 825                 830
```

Figure 10 B

```
Val Leu Leu Pro Ala Ile Asp Gly Ala Thr Val Ala Thr Leu Arg Arg
        835                 840                 845
Gly Gly Gly Val His Arg Leu Leu Thr Ala Leu Ala Glu Ala His Thr
    850                 855                 860
Thr Gly Val Pro Val Asp Trp Ala Ala Val Val Pro Ala Thr Ala Thr
865                     870                 875                 880
Ala His Asp Leu Pro Thr Tyr Ala Phe His His Glu Arg Tyr Trp Ile
            885                     890                 895
Ser His Trp Leu Pro Ser Gly Glu Ala His Pro Arg Pro Ala Asp Asp
            900                 905                 910
Thr Glu Ser Gly Thr Gly Arg Thr Glu Ala Ser Pro Pro Arg Pro His
        915                 920                 925
Asp (SEQ ID NO:3)
```

Figure 10 C

```
Met His Val Pro Gly Glu Glu Asn Gly Glu Pro Leu Ala Ile Val Gly
 1            5                   10                  15
Met Ala Cys Arg Leu Pro Gly Gly Val Ala Ser Pro Glu Asp Leu Trp
            20                  25                  30
Arg Leu Leu Glu Ser Gly Gly Asp Gly Ile Thr Ala Phe Pro Thr Asp
            35                  40                  45
Arg Gly Trp Asp Val Asp Gly Leu Tyr Asp Pro Asp Pro Asp His Pro
    50                  55                  60
Gly Thr Ser Thr Val Arg His Gly Gly Phe Leu Ala Gly Val Ala Asp
65                  70                  75                  80
Phe Asp Ala Ala Phe Phe Gly Ile Ser Pro Arg Glu Ala Leu Ala Met
                85                  90                  95
Asp Pro Gln Gln Arg Leu Val Leu Glu Thr Ser Trp Glu Ala Leu Glu
            100                 105                 110
His Ala Gly Ile Leu Pro Glu Ser Leu Arg Gly Ser Asp Thr Gly Val
            115                 120                 125
Phe Met Gly Ala Phe Ser Asp Gly Tyr Gly Leu Gly Thr Asp Leu Gly
    130                 135                 140
Gly Phe Gly Ala Thr Gly Thr Gln Thr Ser Val Leu Ser Gly Arg Leu
145                 150                 155                 160
Ser Tyr Phe Tyr Gly Leu Glu Gly Pro Ala Val Thr Val Asp Thr Ala
            165                 170                 175
Cys Ser Ser Ser Leu Val Ala Leu His Gln Ala Gly Gln Ser Leu Arg
            180                 185                 190
Ser Gly Glu Cys Ser Leu Ala Leu Val Gly Gly Val Thr Val Met Ala
            195                 200                 205
Ser Pro Ser Gly Phe Val Glu Phe Ser Gln Arg Gly Leu Ala Pro
    210                 215                 220
Asp Ala Arg Cys Lys Ala Phe Ala Asp Ala Ala Asp Gly Thr Gly Phe
225                 230                 235                 240
Ala Glu Gly Ser Gly Val Leu Ile Val Glu Arg Leu Ser Asp Ala Glu
            245                 250                 255
Arg Asn Gly His Arg Val Leu Ala Val Val Arg Gly Ser Ala Val Asn
            260                 265                 270
Gln Asp Gly Ala Ser Asn Gly Leu Ser Ala Pro Asn Gly Pro Ser Gln
    275                 280                 285
Glu Arg Val Ile Arg Gln Ala Leu Ala Asn Ala Gly Leu Thr Pro Ala
    290                 295                 300
Asp Val Asp Ala Val Glu Ala His Gly Thr Gly Thr Arg Leu Gly Asp
305                 310                 315                 320
Pro Ile Glu Ala Gln Ala Val Leu Ala Thr Tyr Gly Gln Gly Arg Asp
                325                 330                 335
Thr Pro Val Leu Leu Gly Ser Leu Lys Ser Asn Ile Gly His Thr Gln
            340                 345                 350
Ala Ala Ala Gly Val Ala Gly Val Ile Lys Met Val Leu Ala Met Arg
            355                 360                 365
His Gly Thr Leu Pro Arg Thr Leu His Val Asp Thr Pro Ser Ser His
    370                 375                 380
Val Asp Trp Thr Ala Gly Ala Val Glu Leu Leu Thr Asp Ala Arg Pro
385                 390                 395                 400
Trp Pro Glu Thr Asp Arg Pro Arg Arg Ala Gly Val Ser Ser Phe Gly
                405                 410                 415
Val Ser Gly Thr Asn Ala His Val Leu Leu Glu Ala His Pro Ala Gly
            420                 425                 430
Glu Pro Pro Ala Glu Glu Pro Ser Ala Ser Lys Pro Gly Glu Pro Leu
            435                 440                 445
```

Figure 11 A

```
Ile Ala Thr Pro Leu Thr Pro Leu Pro Val Ser Ala Arg Thr Ala Thr
    450                 455                 460
Ala Leu Asp Gly Gln Val Arg Arg Leu Arg Glu His Leu Ala Ala Arg
465                 470                 475                 480
Pro Gly His Asp Pro Arg Ala Ile Ala Ala Gly Leu Leu Ala Arg Arg
                485                 490                 495
Thr Thr Phe Pro His Arg Ala Val Leu Leu Asp Asp Asp Val Val Thr
                500                 505                 510
Gly Thr Ala Leu Thr Glu Pro Arg Thr Val Phe Val Phe Pro Gly Gln
        515                 520                 525
Gly Pro Gln Trp Arg Gly Met Gly Val Glu Leu Met Ala Ala Ser Pro
    530                 535                 540
Val Phe Ala Ala Arg Met Arg Gln Cys Ala Asp Ala Leu Ile Pro His
545                 550                 555                 560
Thr Gly Trp Asp Pro Ile Ala Met Leu Asp Asp Pro Glu Val Thr Arg
                565                 570                 575
Arg Val Asp Val Val His Pro Val Cys Trp Ala Val Met Val Ser Leu
            580                 585                 590
Ala Ala Val Trp Glu Ala Ala Gly Val Arg Pro Asp Ala Val Ile Gly
        595                 600                 605
His Ser Gln Gly Glu Ile Ala Ala Ala Cys Val Ala Gly Ala Leu Thr
    610                 615                 620
Leu Glu Asp Gly Ala Arg Leu Val Ala Leu Arg Ser Val Leu Leu Leu
625                 630                 635                 640
Leu Arg Glu Leu Ala Gly Arg Gly Ala Met Gly Ser Val Ala Leu Pro
                645                 650                 655
Ala Ala Asp Val Glu Ala Asp Ala Ala Arg Ile Asp Gly Val Trp Val
            660                 665                 670
Ala Gly Arg Asn Gly Ala Thr Thr Thr Thr Val Ala Gly Arg Pro Asp
        675                 680                 685
Ala Val Glu Thr Leu Ile Ala Asp Tyr Glu Ala Arg Gly Val Trp Val
    690                 695                 700
Arg Arg Ile Ala Val Asp Cys Pro Thr His Thr Pro Phe Val Asp Pro
705                 710                 715                 720
Leu Tyr Asp Glu Leu Gln Arg Ile Val Ala Asp Thr Thr Ser Arg Thr
                725                 730                 735
Pro Glu Ile Pro Trp Phe Ser Thr Ala Asp Glu Arg Trp Ile Asp Ala
            740                 745                 750
Pro Leu Asp Asp Glu Tyr Trp Phe Arg Asn Met Arg His Pro Val Gly
        755                 760                 765
Phe Ala Thr Ala Val Thr Ala Ala Arg Glu Pro Gly Asp Thr Val Phe
    770                 775                 780
Val Glu Val Ser Ala His Pro Val Leu Leu Pro Ala Ile Asp Gly Ala
785                 790                 795                 800
Thr Val Ala Thr Leu Arg Arg Gly Gly Val His Arg Leu Leu Thr
                805                 810                 815
Ala Leu Ala Glu Ala His Thr Thr Gly Val Pro Val Asp Trp Ala Ala
            820                 825                 830
Val Val Pro Ala Thr Ala Thr Ala His Asp Leu Pro Thr Tyr Ala Phe
        835                 840                 845
His His Glu Arg Tyr Trp Ile Ser His Trp Leu Pro Ser Gly Glu Ala
    850                 855                 860
His Pro Arg Pro Ala Asp Asp Thr Glu Ser Gly Thr Gly Arg Thr Glu
865                 870                 875                 880
Ala Ser Pro Pro Arg Pro His Asp (SEQ ID NO:4)
                885
```

Figure 11 B

```
Met His Val Pro Gly Glu Glu Asn Gly Glu Pro Leu Ala Ile Val Gly
 1            5                    10                   15
Met Ala Cys Arg Leu Pro Gly Gly Val Ala Ser Pro Glu Asp Leu Trp
             20                  25                  30
Arg Leu Leu Glu Ser Gly Gly Asp Gly Ile Thr Ala Phe Pro Thr Asp
             35                  40                  45
Arg Gly Trp Asp Val Asp Gly Leu Tyr Asp Pro Asp Pro Asp His Pro
         50                  55                  60
Gly Thr Ser Thr Val Arg His Gly Gly Phe Leu Ala Gly Val Ala Asp
65                       70                  75                  80
Phe Asp Ala Ala Phe Phe Gly Ile Ser Pro Arg Glu Ala Leu Ala Met
                 85                  90                      95
Asp Pro Gln Gln Arg Leu Val Leu Glu Thr Ser Trp Glu Ala Leu Glu
             100                 105                 110
His Ala Gly Ile Leu Pro Glu Ser Leu Arg Gly Ser Asp Thr Gly Val
             115                 120                 125
Phe Met Gly Ala Phe Ser Asp Gly Tyr Gly Leu Gly Thr Asp Leu Gly
        130                 135                 140
Gly Phe Gly Ala Thr Gly Thr Gln Thr Ser Val Leu Ser Gly Arg Leu
145                 150                 155                 160
Ser Tyr Phe Tyr Gly Leu Glu Gly Pro Ala Val Thr Val Asp Thr Ala
                 165                 170                 175
Gln Ser Ser Ser Leu Val Ala Leu His Gln Ala Gly Gln Ser Leu Arg
             180                 185                 190
Ser Gly Glu Cys Ser Leu Ala Leu Val Gly Gly Val Thr Val Met Ala
         195                 200                 205
Ser Pro Ser Gly Phe Val Glu Phe Ser Gln Gln Arg Gly Leu Ala Pro
    210                 215                 220
Asp Ala Arg Cys Lys Ala Phe Ala Asp Ala Ala Asp Gly Thr Gly Phe
225             230                 235                     240
Ala Glu Gly Ser Gly Val Leu Ile Val Glu Arg Leu Ser Asp Ala Glu
             245                 250                 255
Arg Asn Gly His Arg Val Leu Ala Val Val Arg Gly Ser Ala Val Asn
             260                 265                 270
Gln Asp Gly Ala Ser Asn Gly Leu Ser Ala Pro Asn Gly Pro Ser Gln
         275                 280                 285
Glu Arg Val Ile Arg Gln Ala Leu Ala Asn Ala Gly Leu Thr Pro Ala
    290                 295                 300
Asp Val Asp Ala Val Glu Ala His Gly Thr Gly Thr Arg Leu Gly Asp
305                 310                 315                 320
Pro Ile Glu Ala Gln Ala Val Leu Ala Thr Tyr Gly Gln Gly Arg Asp
                 325                 330                 335
Thr Pro Val Leu Leu Gly Ser Leu Lys Ser Asn Ile Gly His Thr Gln
             340                 345                 350
Ala Ala Ala Gly Val Ala Gly Val Ile Lys Met Val Leu Ala Met Arg
             355                 360                 365
His Gly Thr Leu Pro Arg Thr Leu His Val Asp Thr Pro Ser Ser His
    370                 375                 380
Val Asp Trp Thr Ala Gly Ala Val Glu Leu Leu Thr Asp Ala Arg Pro
385                 390                 395                 400
Trp Pro Glu Thr Asp Arg Pro Arg Arg Ala Gly Val Ser Ser Phe Gly
             405                 410                 415
Val Ser Gly Thr Asn Ala His Val Leu Leu Glu Ala His Pro Ala Gly
             420                 425                 430
Glu Pro Pro Ala Glu Glu Pro Ser Ala Ser Lys Pro Gly Glu Pro Leu
             435                 440                 445
```

Figure 12 A

```
Ile Ala Thr Pro Leu Thr Pro Leu Pro Val Ser Ala Arg Thr Ala Thr
450                 455                 460
Ala Leu Asp Gly Gln Val Arg Arg Leu Arg Glu His Leu Ala Ala Arg
465                 470                 475                 480
Pro Gly His Asp Pro Arg Ala Ile Ala Ala Gly Leu Leu Ala Arg Arg
                485                 490                 495
Thr Thr Phe Pro His Arg Ala Val Leu Leu Asp Asp Asp Val Val Thr
            500                 505                 510
Gly Thr Ala Leu Thr Glu Pro Arg Thr Val Phe Val Phe Pro Gly Gln
            515                 520                 525
Gly Pro Gln Trp Arg Gly Met Gly Val Glu Leu Met Ala Ala Ser Pro
530                 535                 540
Val Phe Ala Ala Arg Met Arg Gln Cys Ala Asp Ala Leu Ile Pro His
545                 550                 555                 560
Thr Gly Trp Asp Pro Ile Ala Met Leu Asp Asp Pro Glu Val Thr Arg
                565                 570                 575
Arg Val Asp Val Val His Pro Val Cys Trp Ala Val Met Val Ser Leu
                580                 585                 590
Ala Ala Val Trp Glu Ala Gly Val Arg Pro Asp Ala Val Ile Gly
                595                 600                 605
His Ser Gln Gly Glu Ile Ala Ala Ala Cys Val Ala Gly Ala Leu Thr
    610                 615                 620
Leu Glu Asp Gly Ala Arg Leu Val Ala Leu Arg Ser Val Leu Leu Leu
625                 630                 635                 640
Leu Arg Glu Leu Ala Gly Arg Gly Ala Met Gly Ser Val Ala Leu Pro
                645                 650                 655
Ala Ala Asp Val Glu Ala Asp Ala Ala Arg Ile Asp Gly Val Trp Val
                660                 665                 670
Ala Gly Arg Asn Gly Ala Thr Thr Thr Thr Val Ala Gly Arg Pro Asp
                675                 680                 685
Ala Val Glu Thr Leu Ile Ala Asp Tyr Glu Ala Arg Gly Val Trp Val
                690                 695                 700
Arg Arg Ile Ala Val Asp Cys Pro Thr His Thr Pro Phe Val Asp Pro
705                 710                 715                 720
Leu Tyr Asp Glu Leu Gln Arg Ile Val Ala Asp Thr Thr Ser Arg Thr
                725                 730                 735
Pro Glu Ile Pro Trp Phe Ser Thr Ala Asp Glu Arg Trp Ile Asp Ala
                740                 745                 750
Pro Leu Asp Asp Glu Tyr Trp Phe Arg Asn Met Arg His Pro Val Gly
            755                 760                 765
Phe Ala Thr Ala Val Thr Ala Ala Arg Glu Pro Gly Asp Thr Val Phe
770                 775                 780
Val Glu Val Ser Ala His Pro Val Leu Leu Pro Ala Ile Asp Gly Ala
785                 790                 795                 800
Thr Val Ala Thr Leu Arg Arg Gly Gly Val His Arg Leu Leu Thr
                805                 810                 815
Ala Leu Ala Glu Ala His Thr Thr Gly Val Pro Val Asp Trp Ala Ala
                820                 825                 830
Val Val Pro Ala Thr Ala Thr Ala His Asp Leu Pro Thr Tyr Ala Phe
            835                 840                 845
His His Glu Arg Tyr Trp Ile Ser His Trp Leu Pro Ser Gly Glu Ala
850                 855                 860
His Pro Arg Pro Ala Asp Asp Thr Glu Ser Gly Thr Gly Arg Thr Glu
865                 870                 875                 880
Ala Ser Pro Pro Arg Pro His Asp (SEQ ID NO:5)
                885
```

Figure 12 B

HETEROLOGOUS PRODUCTION OF 15-METHYL-6-DEOXYERTHRONOLIDE B

CROSS-REFERENCE TO RELATED APPLICATIONS

This application claims priority to U.S. patent application Ser. No. 60/161,414, filed Oct. 25, 1999, and is related to U.S. patent application Ser. Nos. 60/161,703, filed Oct. 27, 1999, and 60/206,082, filed May 18, 2000, each of which is incorporated herein by reference.

REFERENCE TO GOVERNMENT FUNDING

This invention was supported in part by Grant No. AI51106. The U.S. government has certain rights in this invention.

FIELD OF THE INVENTION

The present invention provides recombinant methods and materials for producing polyketides by recombinant DNA technology. The invention relates to the fields of agriculture, animal husbandry, chemistry, medicinal chemistry, medicine, molecular biology, pharmacology, and veterinary technology.

BACKGROUND OF THE INVENTION

Polyketides represent a large family of diverse compounds synthesized from 2-carbon units through a series of condensations and subsequent modifications. Polyketides occur in many types of organisms, including fungi and mycelial bacteria, in particular, the actinomycetes. There are a wide variety of polyketide structures, and the class of polyketides encompasses numerous compounds with diverse activities. Erythromycin, FK-506, FK-520, megalomycin, narbomycin, oleandomycin, picromycin, rapamycin, spinocyn, and tylosin are examples of such compounds. Given the difficulty in producing polyketide compounds by traditional chemical methodology, and the typically low production of polyketides in wild-type cells, there has been considerable interest in finding improved or alternate means to produce polyketide compounds. See PCT publication Nos. WO 93/13663; WO 95/08548; WO 96/40968; 97/02358; and 98/27203; U.S. Pat. Nos. 4,874, 748; 5,063,155; 5,098,837; 5,149,639; 5,672,491; and 5,712,146; Fu et al., 1994, Biochemistry 33: 9321–9326; McDaniel et al., 1993, Science 262: 1546–1550; and Rohr, 1995, Angew. Chem. Int. Ed. Engl. 34(8): 881–888, each of which is incorporated herein by reference.

Polyketides are synthesized in nature by polyketide synthase (PKS) enzymes. These enzymes, which are complexes of multiple large proteins, are similar to the synthases that catalyze condensation of 2-carbon units in the biosynthesis of fatty acids. PKS enzymes are encoded by PKS genes that usually consist of three or more open reading frames (ORFs). Two major types of PKS enzymes are known; these differ in their composition and mode of synthesis. These two major types of PKS enzymes are commonly referred to as Type I or "modular" and Type II "iterative" PKS enzymes. A third type of PKS found primarily in fungal cells has features of both the Type I and Type II enzymes and is referred to as "fungal" PKS enzymes.

Modular PKSs are responsible for producing a large number of 12-, 14-, and 16-membered macrolide antibiotics including erythromycin, megalomycin, methymycin, narbomycin, oleandomycin, picromycin, and tylosin. Each ORF of a modular PKS can comprise one, two, or more "modules" of ketosynthase activity, each module of which consists of at least two (if a loading module) and more typically three (for the simplest extender module) or more enzymatic activities or "domains." These large multifunctional enzymes (>300,000 kDa) catalyze the biosynthesis of polyketide macrolactones through multistep pathways involving decarboxylative condensations between acyl thioesters followed by cycles of varying β-carbon processing activities (see O'Hagan, D. *The polyketide metabolites*; E. Horwood: New York, 1991, incorporated herein by reference).

During the past half decade, the study of modular PKS function and specificity has been greatly facilitated by the plasmid-based *Streptomyces coelicolor* expression system developed with the 6-deoxyerythronolide B (6-dEB) synthase (DEBS) genes (see Kao et al., 1994, *Science*, 265: 509–512, McDaniel et al., 1993, *Science* 262: 1546–1557, and U.S. Pat. Nos. 5,672,491 and 5,712,146, each of which is incorporated herein by reference). The advantages to this plasmid-based genetic system for DEBS are that it overcomes the tedious and limited techniques for manipulating the natural DEBS host organism, *Saccharopolyspora erythraea*, allows more facile construction of recombinant PKSs, and reduces the complexity of PKS analysis by providing a "clean" host background. This system also expedited construction of the first combinatorial modular polyketide library in Streptomyces (see PCT publication No. WO 98/49315, incorporated herein by reference).

The ability to control aspects of polyketide biosynthesis, such as monomer selection and degree of β-carbon processing, by genetic manipulation of PKSs has stimulated great interest in the combinatorial engineering of novel antibiotics (see Hutchinson, 1998, *Curr. Opin. Microbiol.* 1: 319–329; Carreras and Santi, 1998, *Curr. Opin. Biotech.* 9: 403–411; and U.S. Pat. Nos. 5,712,146 and 5,672,491, each of which is incorporated herein by reference). This interest has resulted in the cloning, analysis, and manipulation by recombinant DNA technology of genes that encode PKS enzymes. The resulting technology allows one to manipulate a known PKS gene cluster either to produce the polyketide synthesized by that PKS at higher levels than occur in nature or in hosts that otherwise do not produce the polyketide. The technology also allows one to produce molecules that are structurally related to, but distinct from, the polyketides produced from known PKS gene clusters.

One example of this technology involves the use of a PKS in which the first extender module is inactivated by mutation and synthetic molecules, called diketides. These diketides are provided to the altered PKS and bind to the second extender module. The diketides are then processed by the PKS in the normal fashion to yield a polyketide. If the diketide provided differs in structure from the corresponding diketide that is the product of the first extender module, then the polyketide will correspondingly differ from the natural polyketide produced by the intact PKS. See PCT patent publication Nos. 97/02358 and 99/03986, each of which is incorporated herein by reference. One important compound produced by this technology resulted from feeding a propyl diketide to DEBS to produce 15-methyl-6-dEB. This molecule is referred to herein as propyl-6-dEB, because it has a C-13 propyl group where 6-dEB has a C-13 ethyl group.

While the diketide feeding technology provides useful amounts of compound, the cost of producing polyketides by that technology is increased by the need to prepare the synthetic diketide. Moreover, certain polyketide producing cells degrade some of the diketide before it can be incorporated into a polyketide by the PKS, thus increasing the cost of production. Thus, there remains a need for methods to produce polyketides by other means. The present invention helps meet that need by providing recombinant host cells, expression vectors, and methods for making polyketides in diverse host cells.

SUMMARY OF THE INVENTION

The present invention provides recombinant host cells and expression vectors for making propyl-6-dEB and compounds derived therefrom. The present invention also provides methods for increasing the amounts of propyl-6-dEB produced in a host cell by providing recombinant biosynthetic pathways for production of a precursor utilized in the biosynthesis of the compound and optionally altering other biosynthetic pathways in the cell.

In one embodiment, the host cell does not produce propyl-6-dEB, and the host cell is modified by introduction of a recombinant expression vector so that it can produce the compound. In another embodiment, propyl-6-dEB is produced in the host cell in small amounts, and the host cell is modified by introduction of a recombinant expression vector so that it can produce the compound in larger amounts. In a preferred embodiment, the host cell is altered to produce the precursor butyryl CoA by transferring the genes that encode the enzymes that produce butyryl CoA from a first cell to the host cell. The transfer is accomplished using an expression vector of the invention. The expression vector drives expression of the genes and production of butyryl CoA in the second cell.

In another embodiment, the product is a polyketide other than 6-dEB that is made by a PKS that utilizes propionyl CoA. The polyketide produced by the host cell of the invention containing the PKS differs from the usual product produced by the PKS in that butyryl CoA instead of propionyl CoA is utilized by the PKS in producing the polyketide. The polyketide is a polyketide synthesized by either a modular, iterative, or fungal PKS. In one preferred embodiment, the polyketide is synthesized by a modular PKS.

In one embodiment, the host cell is either a procaryotic or eukaryotic host cell. In one embodiment, the host cell is a Saccharopolyspora host cell, including but not limited to *S. erythraea*. In another embodiment, the host cell is a Streptomyces host cell, including but not limited to *S. coelicolor*, *S. lividans*, and *S. venezuelae*. In another embodiment, the host cell is an *E. coli* host cell. In another embodiment, the host cell is a yeast host cell. In another embodiment, the host cell is a plant host cell.

In one embodiment, the invention provides a recombinant expression vector that comprises a promoter positioned to drive expression of one or more genes that encode the enzymes required for biosynthesis of butyryl CoA. In a preferred embodiment, the promoter is derived from a PKS gene. In a related embodiment, the invention provides recombinant host cells comprising one or more expression vectors that drive expression of the enzymes that produce the precursor.

In another embodiment, the invention provides a recombinant host cell that comprises not only an expression vector of the invention but also an expression vector that comprises a promoter positioned to drive expression of a PKS. In a related embodiment, the invention provides recombinant host cells comprising the vector that produces the PKS and its corresponding polyketide.

These and other embodiments of the invention are described in more detail in the following description, the examples, and claims set forth below.

BRIEF DESCRIPTION OF THE FIGURES

FIGS. 3A–C show the eryM gene sequence with the engineered XbaI and native HindIII sites (SEQ ID NO: 1 and SEQ ID NO:2).

FIGS. 10A–C show the amino acid sequence of a hybrid PKS (SEQ ID NO:3).

FIGS. 11A–B show the amino acid sequence of another hybrid PKS (SEQ ID NO:4).

FIGS. 12A–B show the amino acid sequence of a final hybrid PKS SEQ ID NO:5).

DETAILED DESCRIPTION OF THE INVENTION

Figure 1:
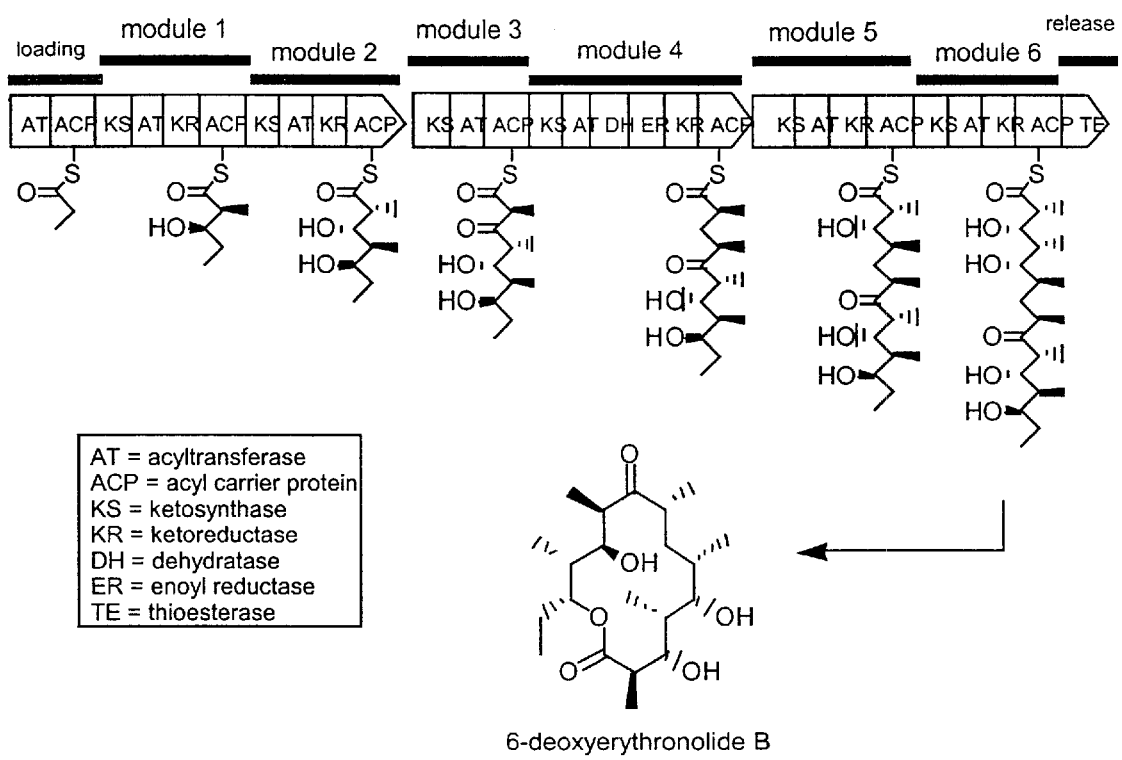
FIG. 1 shows the modules and domains of DEBS and the biosynthesis of 6-dEB from propionyl CoA and methylmalonyl CoA.

The present invention provides recombinant host cells and expression vectors for making products in host cells, which are otherwise unable to make those products due to the lack of a biosynthetic pathway to produce a precursor required for biosynthesis of the product. As used herein, the term recombinant refers to a cell, compound, or composition produced at least in part by human intervention. The present invention also provides methods for increasing the amounts of a product produced in a host cell by providing recombinant biosynthetic pathways for production of a precursor utilized in the biosynthesis of a product.

In one embodiment, the host cell does not produce the precursor, and the host cell is modified by introduction of a recombinant expression vector so that it can produce the precursor. In another embodiment, the precursor is produced in the host cell in small amounts, and the host cell is modified by introduction of a recombinant expression vector so that it can produce the precursor in larger amounts. In a preferred embodiment, the precursor is a primary metabolite that is produced in a first cell but not in a second heterologous cell. In accordance with the methods of the invention, the genes that encode the enzymes that produce the primary metabolite in the first cell are transferred to the second cell. The transfer is accomplished using an expression vector of the invention. The expression vector drives expression of the genes and production of the metabolite in the second cell.

The invention, in its most general form, concerns the introduction, in whole or in part, of a metabolic pathway from one cell into a heterologous host cell. The invention also encompasses the modification of an existing metabolic pathway, in whole or in part, in a cell, through the introduction of heterologous genetic material into the cell. In all embodiments, the resulting cell is different with regard to its cellular physiology and biochemistry in a manner such that the bio-synthesis, bio-degradation, transport, biochemical modification, or levels of intracellular metabolites allow production or improve expression of desired products. The invention is exemplified by increasing the level of polyketides produced in a heterologous host and by restricting the chemical composition of products to the desired structures.

Thus, in a preferred embodiment, the product produced by the cell is a polyketide. The polyketide is a polyketide synthesized by either a modular, iterative, or fungal PKS. The precursor is selected from the group consisting of malonyl CoA, butyryl CoA, propionyl CoA, methylmalonyl CoA, ethylmalonyl CoA, and hydroxymalonyl CoA. In an especially preferred embodiment, the polyketide utilizes butyryl or ethylmalonyl CoA in its biosynthesis. In another preferred embodiment, the polyketide is synthesized by a modular PKS.

The polyketide class of natural products includes members having diverse structural and pharmacological properties (see Monaghan and Tkacz, 1990, $Annu. Rev. Microbiol.$ 44: 271, incorporated herein by reference). Polyketides are assembled by polyketide synthases through successive condensations of activated coenzyme-A thioester monomers derived from small organic acids such as acetate, propionate, and butyrate. Active sites required for condensation include an acyltransferase (AT), acyl carrier protein (ACP), and beta-ketoacylsynthase (KS). Each condensation cycle results in a β-keto group that undergoes all, some, or none of a series of processing activities. Active sites that perform these reactions include a ketoreductase (KR), dehydratase (DH), and enoylreductase (ER). Thus, the absence of any beta-keto processing domain results in the presence of a ketone, a KR alone gives rise to a hydroxyl, a KR and DH result in an alkene, while a KR, DH, and ER combination leads to complete reduction to an alkane. After assembly of the polyketide chain, the molecule typically undergoes cyclization(s) and post-PKS modification (e.g. glycosylation, oxidation, acylation) to achieve the final active compound.

Macrolides such as erythromycin and megalomycin are synthesized by modular PKSs (see Cane et al., 1998, $Science$ 282: 63, incorporated herein by reference). For illustrative purposes, the PKS that produces the erythromycin polyketide (6-deoxyerythronolide B synthase or DEBS; see U.S. Pat. No. 5,824,513, incorporated herein by reference) is shown in FIG. 1. DEBS is the most characterized and extensively used modular PKS system. DEBS synthesizes the polyketide 6-deoxyerythronolide B (6-dEB) from propionyl CoA and methylmalonyl CoA. In modular PKS enzymes such as DEBS, the enzymatic steps for each round of condensation and reduction are encoded within a single "module" of the polypeptide (i.e., one distinct module for every condensation cycle). DEBS consists of a loading module and 6 extender modules and a chain terminating thioesterase (TE) domain within three extremely large polypeptides encoded by three open reading frames (ORFs, designated eryAI, eryAII, and eryAIII).

Each of the three polypeptide subunits of DEBS (DEBSI, DEBSII, and DEBSIII) contains 2 extender modules, DEBSI additionally contains the loading module. Collectively, these proteins catalyze the condensation and appropriate reduction of 1 propionyl CoA starter unit and 6 methylmalonyl CoA extender units. Modules 1, 2, 5, and 6 contain KR domains; module 4 contains a complete set, KR/DH/ER, of reductive and dehydratase domains; and module 3 contains no functional reductive domain. Following the condensation and appropriate dehydration and reduction reactions, the enzyme bound intermediate is lactonized by the TE at the end of extender module 6 to form 6-dEB.

More particularly, the loading module of DEBS consists of two domains, an acyl-transferase (AT) domain and an acyl carrier protein (ACP) domain. In some other PKS enzymes, the loading module is not composed of an AT and an ACP but instead utilizes an inactivated KS, an AT, and an ACP. This inactivated KS is in most instances called $KS^Q$, where the superscript letter is the abbreviation for the amino acid, glutamine, that is present instead of the active site cysteine required for activity. The AT domain of the loading module recognizes a particular acyl CoA (propionyl for DEBS, which can also accept acetyl or butyryl) and transfers it as a thiol ester to the ACP of the loading module. Concurrently, the AT on each of the extender modules recognizes a particular extender-CoA (methylmalonyl for DEBS) and transfers it to the ACP of that module to form a thioester. Once the PKS is primed with acyl- and malonyl-ACPs, the acyl group of the loading module migrates to form a thiol ester (trans-esterification) at the KS of the first extender module; at this stage, extender module 1 possesses an acyl-KS and a methylmalonyl ACP. The acyl group derived from the loading module is then covalently attached to the alpha-carbon of the malonyl group to form a carbon-carbon bond, driven by concomitant decarboxylation, and generating a new acyl-ACP that has a backbone two carbons longer than the loading unit (elongation or extension). The growing polyketide chain is transferred from the ACP to the KS of the next module, and the process continues.

The polyketide chain, growing by two carbons each module, is sequentially passed as a covalently bound thiol ester from module to module, in an assembly line-like process. The carbon chain produced by this process alone would possess a ketone at every other carbon atom, producing a polyketone, from which the name polyketide arises. Commonly, however, the beta keto group of each two-carbon unit is modified just after it has been added to the growing polyketide chain but before it is transferred to the next module by either a KR, a KR plus a DH, or a KR, a DH, and an ER. As noted above, modules may contain additional enzymatic activities as well.

Once a polyketide chain traverses the final extender module of a PKS, it encounters the releasing domain or thioesterase found at the carboxyl end of most PKSs. Here, the polyketide is cleaved from the enzyme and cyclyzed. The resulting polyketide can be modified further by tailoring or modification enzymes; these enzymes add carbohydrate groups or methyl groups, or make other modifications, i.e., oxidation or reduction, on the polyketide core molecule. For example, the final steps in conversion of 6-dEB to erythromycin A include the actions of a number of modification enzymes, such as: C-6 hydroxylation, attachment of mycarose and desosamine sugars, C-12 hydroxylation (which produces erythromycin C), and conversion of mycarose to cladinose via O-methylation.

DEBS is produced naturally in $Saccharopolyspora$ $erythraea$ and has been transferred via recombinant DNA methodology to a variety of Streptomyces species, such as $S.$ $coelicolor$ CH999 and $S. lividans$ K4-114 and K4-155, in which it functions without further modification of the host cell to produce 6-dEB (using the propionyl CoA starter unit) and 8,8a-deoxyoleandolide (using the acetyl CoA starter unit). These two compounds differ from one another with regard to the substituent at the C-13 position: 6-dEB has an ethyl and 8,8a-deoxyoleandolide a methyl at the C-13 position. Using a recombinant version of the DEBSI protein, researchers reported that DEBS could also accept a butyryl Co A starter unit (see Pieper et al., 1996, *Biochemistry* 35: 2054–2060, incorporated herein by reference). If the complete DEBS enzyme utilized butyryl CoA as a starter unit, then the product of the PKS would be propyl-6-dEB.

Propyl-6-dEB has also been prepared using a recombinant DEBS enzyme in which the KS domain of extender module 1 was inactivated by a mutation changing the active site cysteine residue to an alanine residue. When the recombinant PKS was provided an activated form of a synthetic diketide having the structure of a diketide produced by the DEBS-mediated condensation of a butyryl CoA starter unit and a methylmalonyl CoA extender unit, propyl-6-dEB was produced. Moreover, when propyl-6-dEB was provided to *Saccharopolyspora erythraea* cells, the cells could take up the aglycone and convert it to the corresponding propyl analogs of erythromycin A, B, C, and D. See PCT patent publication Nos. 99/03986, 97/02358, and 98/49315, incorporated herein by reference. Propyl erythromycin A is a particularly useful compound in that it has potent antibiotic activity and can be readily converted to even more active compounds, such as the ketolides (see PCT patent applications U.S.00/09914 and U.S.00/09915, both of which are incorporated herein by reference) by chemical methodology.

Although the above results demonstrate that DEBS can accept butyryl CoA as a starter unit, complete the synthesis of propyl-6-dEB, and then modify the aglycone to yield the propyl erythromycins, the propyl erythromycins have not been reported in fermentations of erythromycin producing *Saccharopolyspora erythraea* strains. In one embodiment, the present invention provides recombinant *S. erythraea* strains that produce propyl-6-dEB and the propyl erythromycins.

In a first aspect, this embodiment of the invention is exemplified by recombinant *Saccharopolyspora erythraea* strains in which the eryM gene has been inactivated by mutation. The eryM gene encodes a malonyl decarboxylase that converts methylmalonyl CoA to propionyl CoA. When the eryM gene is inactivated by mutation, the production of erythromycin in *S. erythraea* in minimal media is dependent on the feeding of exogenous propionic acid. See Hsieh & Kolattukudy, 1994, *J. Bacteriol.* 176: 714–724, incorporated herein by reference. In accordance with a method of the invention, an eryM mutant strain is provided with exogenous butyric acid and fermented to produce propyl-6-dEB and the propyl erythromycins.

While the above method can result in the production of the desired compounds, the requirement of adding exogenous butyric acid to the fermentation media is not only inconvenient but also limits production to the amount of butyric acid that can be taken up by the cells. This can be addressed by the addition of transporter and CoA ligase genes of the appropriate specificity (see, e.g., U.S. patent application Serial No. 60/206,082, filed May 18, 2000, incorporated herein by reference). As another means of overcoming this potential limitation, the present invention provides recombinant host cells that make butyryl CoA. Because these host cells can make butyryl CoA, providing exogenous butyric acid to the media is not required, although it may in some instances increase the amount of propyl-6-dEB and propyl erythromycins produced.

Figure 2:
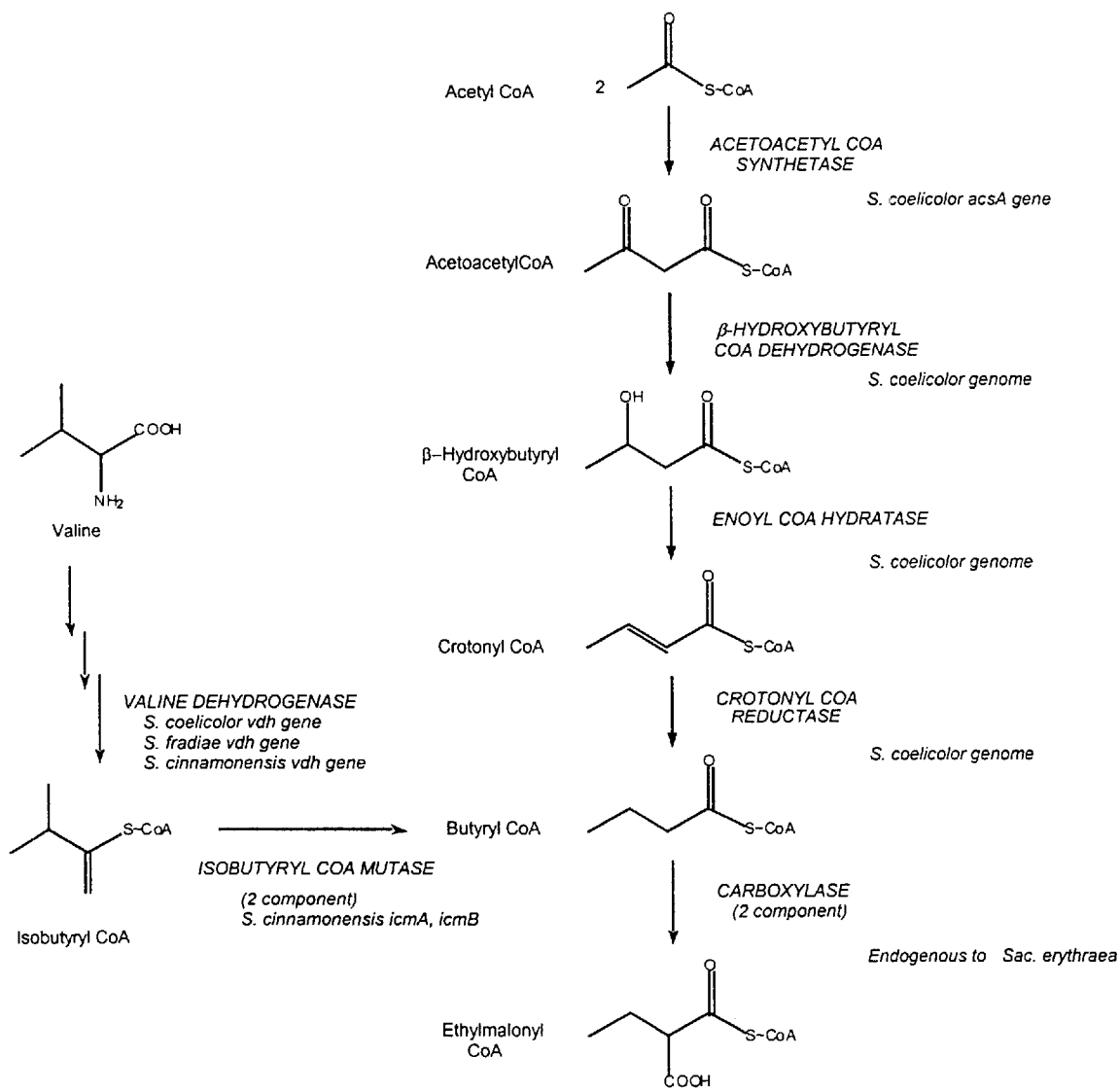
FIG. 2 shows biosynthetic pathways for the production of butyryl CoA and ethylmalonyl CoA.

The present invention provides a wide variety of such host cells. In general, these host cells comprise one or more biosynthetic pathways for producing butyryl CoA. FIG. 2 shows two illustrative pathways. On the left side of the Figure, the pathway starting with valine is shown. On the right side of the Figure, the pathway starting with acetyl CoA is shown. The host cells of the invention can comprise either or both of these pathways. In one embodiment, the recombinant host cell is derived from a host cell that lacks either pathway, and the genes for one or both pathways are added to provide the host cell of the invention. In another embodiment, the recombinant host cell is derived from a host cell that has one pathway but lacks the other, and the genes for the other pathway are added to provide the host cell of the invention.

As shown on the left side of FIG. 2, butyryl CoA can be synthesized from valine by a pathway in which valine is first converted to isobutyryl CoA by the enzyme valine dehydrogenase. This enzyme is the product of the vdh gene, which can be isolated from *Streptomyces coelicolor, S. fradiae, S. cinnamonensis*, and other host cells. Isobutyryl CoA is then converted to butyryl CoA by isobutyryl CoA mutase. This enzyme is present in *S. cinnamonensis* in a two subunit form; the subunits are the products of the icmA and icmB genes. Genes encoding this enzyme can also be isolated from other host cells.

As shown on the right side of FIG. 2, butyryl CoA can be synthesized from acetyl CoA by a pathway in which acetyl CoA is first converted to acetoacetyl CoA by the enzyme acetoacetyl CoA synthetase. This enzyme is the product of the acsA gene, which can be isolated from *Streptomyces coelicolor* and other host cells. Acetoacetyl CoA is then converted to beta-hydroxybutyryl CoA by the enzyme beta-hydroxybutyryl CoA dehydrogenase. The gene (bdh) encoding this enzyme can be isolated from *Streptomyces coelicolor* and other host cells. Beta-hydroxybutyryl CoA is then converted to crotonyl CoA by the enzyme enoyl CoA hydratase. The gene (ech) encoding this enzyme can be isolated from *Streptomyces coelicolor* and other host cells. Crotonyl CoA is then converted to butyryl CoA by the enzyme crotonyl CoA reductase. The gene (ccr) encoding this enzyme can be isolated from *Streptomyces coelicolor* and other host cells.

Those of skill in the art will recognize that, depending on the host cell selected, not all of the genes in a pathway may be required. This is because some host cells will express one or more genes in a pathway naturally, requiring the addition of only a few of the genes to complete the pathway. This aspect of the invention is illustrated with *Saccharopolyspora erythraea*, which is modified in accordance with the invention to make propyl-6-dEB and the propyl erythromycins instead of 6-dEB and the erythromycins. Thus, as discussed above, one can modify *S. erythraea* cells to knock out or otherwise inactivate the eryM gene. The thus modified host cells can be cultured in fermentation media comprising butyric acid to provide the desired propyl-6-dEB and propyl erythromycins.

To improve production of the desired compounds, the cells can be transformed with a recombinant DNA expression vector that comprises the ccr gene. The cells may contain enough endogenous product of acsA, bdh, and ech genes that merely the addition of the ccr gene will increase the production of propyl-6-dEB and the propyl erythromycins. Optionally, however, the cells are transformed with a recombinant DNA expression vector that comprises the ccr, acsA, bdh, and ech genes to provide the propyl-6-dEB and propyl erythromycins in high yield.

Alternatively, the cells can be transformed with a recombinant DNA expression vector that comprises the icmA and icmB genes (hereinafter referred to as the icm gene). The cells may contain enough endogenous product of the vdh gene that merely the addition of the icm gene will increase the production of propyl-6-dEB and the propyl erythromycins. Optionally, however, the cells are transformed with a recombinant DNA expression vector that comprises the icm and vdh genes to provide the propyl-6-dEB and propyl erythromycins in high yield.

The invention also provides recombinant *Saccharopolyspora erythraea* host cells in which various combinations of recombinant genes are expressed. These host cells include but are not limited to host cells that comprise the following sets of genes:

(i) ccr and icm;

(ii) ccr, acsA, bdh, ech, and icm;

(iii) ccr, acsA, bdh, ech, icm, and vdh; and (iv) icm, vdh, and ccr.

Thus, the invention provides a diverse collection of recombinant *S. erythraea* host cells that produce propyl-6-dEB and the propyl erythromycins in high yield.

In another embodiment, the invention provides a method for the production of 14,15-propenylerythromycin and/or the corresponding 14,15-propenyl-6-deoxyerythronolide B using a recombinant host cell that comprises isobutyryl CoA mutase, valine dehydrogenase, and butyryl CoA dehydrogenase genes. In a preferred embodiment, the host cell is a *Saccharopolyspora erythraea* host cell that optionally does not express a functional eryM gene product. In one embodiment, the butyryl CoA dehydrogenase (bcd) gene is obtained from *Clostridium acetobutylicum* or *Mycobacterium tuberculosis* (fadE25).

The host cells of the invention can also be employed for the expression of recombinant PKS genes for a variety of purposes. As but one non-limiting example, any PKS gene that contains at least one AT domain that binds ethylmalonyl CoA can be expressed in recombinant host cells of the invention that express a carboxylase that converts butyryl CoA to ethylmalonyl CoA. A number of PKS enzymes contain AT domains that bind ethylmalonyl CoA, including but not limited to, the niddamycin PKS and the FK-520 PKS.

The present invention also provides a recombinant PKS gene that encodes a PKS that has an ethylmalonyl CoA specific AT domain. These recombinant PKS genes of the invention are useful in the production of propyl-6-dEB and are characterized by having a loading module comprised of a $KS^Q$ domain, an ethylmalonyl CoA specific AT domain, and an ACP domain, followed by 6 extender modules specific for methylmalonyl CoA. PKS genes that are especially suitable for modification to yield the hybrid PKS of the invention include the DEBS eryA genes, the oleA genes (for oleandomycin), and the meg genes (for megalomycin).

In another embodiment, the present invention provides a hybrid PKS in which the loading module is comprised of a $KS^Q$ domain, an ethylmalonyl CoA specific AT domain, and an ACP domain, and which also contains two or more, preferably 6, but optionally 7, extender modules, wherein at least one extender module has an AT domain specific for malonyl CoA. For example, the loading module can be linked to the 5 extender modules of methymycin or the 6 extender modules of narbomycin or picromycin.

The host cells of the invention are particularly suited for expressing such hybrid PKS genes, because the host cells make butyryl CoA, which is converted to ethylmalonyl CoA. The loading module AT domain binds the ethylmalonyl CoA produced, and the $KS^Q$ domain decarboxylates the ethylmalonyl CoA during its incorporation into the polyketide. Thus, the polyketide produced is propyl-6-dEB if the extender modules are those encoded by the eryA, oleA, or megA genes, and propyl-narbonolide if the extender modules are those encoded by the pica genes.

The present invention provides recombinant DNA expression vectors and methods for making a polyketide and its required precursors in any host cell. In one embodiment, the host cell is either a procaryotic or eukaryotic host cell. The recombinant expression vectors of the invention comprise a promoter positioned to drive expression of one or more genes that encode the enzymes required for biosynthesis of a precursor. In a preferred embodiment, the promoter is derived from a PKS gene. In another embodiment, the invention provides a recombinant host cell that comprises not only an expression vector of the invention but also an expression vector that comprises a promoter positioned to drive expression of a PKS. In a related embodiment, the invention provides recombinant host cells comprising the vector that produces the PKS and its corresponding polyketide.

The methods of the invention involve the introduction of genetic material into a host strain of choice to modify or alter the cellular physiology and biochemistry of the host. Through the introduction of genetic material, the host strain acquires new properties, e.g. the ability to produce a new, or greater quantities of, an intracellular metabolite. In an illustrative embodiment of the invention, the introduction of genetic material into the host strain results in a new or modified ability to produce butyryl CoA. The genetic material introduced into the host strain contains gene(s), or parts of genes, coding for one or more of the enzymes involved in the bio-synthesis/bio-degradation of butyryl CoA and may also include additional elements for the expression and/or regulation of expression of these genes, e.g. promoter sequences.

Those of skill in the art will recognize that, due to the degenerate nature of the genetic code, a variety of DNA compounds differing in their nucleotide sequences can be used to encode a given amino acid sequence of the invention. The native DNA sequence encoding the biosynthetic enzymes described above are referenced herein merely to illustrate a preferred embodiment of the invention, and the invention includes DNA compounds of any sequence that encode the amino acid sequences of the polypeptides and proteins of the enzymes utilized in the methods of the invention. In similar fashion, a polypeptide can typically tolerate one or more amino acid substitutions, deletions, and insertions in its amino acid sequence without loss or significant loss of a desired activity. The present invention includes such polypeptides with alternate amino acid sequences, and the amino acid sequences encoded by the DNA sequences shown herein merely illustrate preferred embodiments of the invention.

Thus, in an especially preferred embodiment, the present invention provides DNA molecules in the form of recombinant DNA expression vectors or plasmids, as described in more detail below, that encode one or more precursor biosynthetic enzymes. Generally, such vectors can either replicate in the cytoplasm of the host cell or integrate into the chromosomal DNA of the host cell. In either case, the vector can be a stable vector (i.e., the vector remains present over many cell divisions, even if only with selective pressure) or a transient vector (i.e., the vector is gradually lost by host cells with increasing numbers of cell divisions). The invention provides DNA molecules in isolated (i.e., not pure, but existing in a preparation in an abundance and/or concentration not found in nature) and purified (i.e., substantially free of contaminating materials or substantially free of materials with which the corresponding DNA would be found in nature) form.

In one important embodiment, the invention provides methods for the heterologous expression of one or more of the biosynthetic genes involved in butyryl CoA biosynthesis and recombinant DNA expression vectors useful in the method. Thus, included within the scope of the invention are recombinant expression vectors that include such nucleic acids. The term expression vector refers to a nucleic acid that can be introduced into a host cell or cell-free transcription and translation system. An expression vector can be maintained permanently or transiently in a cell, whether as part of the chromosomal or other DNA in the cell or in any cellular compartment, such as a replicating vector in the cytoplasm. An expression vector also comprises a promoter that drives expression of an RNA, which typically is translated into a polypeptide in the cell or cell extract. For efficient translation of RNA into protein, the expression vector also typically contains a ribosome-binding site sequence positioned upstream of the start codon of the coding sequence of the gene to be expressed. Other elements, such as enhancers, secretion signal sequences, transcription termination sequences, and one or more marker genes by which host cells containing the vector can be identified and/or selected, may also be present in an expression vector. Selectable markers, i.e., genes that confer antibiotic resistance or sensitivity, are preferred and confer a selectable phenotype on transformed cells when the cells are grown in an appropriate selective medium.

The various components of an expression vector can vary widely, depending on the intended use of the vector and the host cell(s) in which the vector is intended to replicate or drive expression. Expression vector components suitable for the expression of genes and maintenance of vectors in *E. coli*, yeast, Streptomyces, and other commonly used cells are widely known and commercially available. For example, suitable promoters for inclusion in the expression vectors of the invention include those that function in eucaryotic or procaryotic host cells. Promoters can comprise regulatory sequences that allow for regulation of expression relative to the growth of the host cell or that cause the expression of a gene to be turned on or off in response to a chemical or physical stimulus. For *E. coli* and certain other bacterial host cells, promoters derived from genes for biosynthetic enzymes, antibiotic-resistance conferring enzymes, and phage proteins can be used and include, for example, the galactose, lactose (lac), maltose, tryptophan (trp), beta-lactamase (bla), bacteriophage lambda PL, and T5 promoters. In addition, synthetic promoters, such as the tac promoter (U.S. Pat. No. 4,551,433), can also be used. For *E. coli* expression vectors, it is useful to include an *E. coli* origin of replication, such as from pUC, p1P, p1I, and pBR.

Thus, recombinant expression vectors contain at least one expression system, which, in turn, is composed of at least a portion of PKS and/or other biosynthetic gene coding sequences operably linked to a promoter and optionally termination sequences that operate to effect expression of the coding sequence in compatible host cells. The host cells are modified by transformation with the recombinant DNA expression vectors of the invention to contain the expression system sequences either as extrachromosomal elements or integrated into the chromosome. The resulting host cells of the invention are useful in methods to produce PKS enzymes as well as polyketides and antibiotics and other useful compounds derived therefrom.

Preferred host cells for purposes of selecting vector components for expression vectors of the present invention include fungal host cells such as yeast and procaryotic host cells such as *E. coli*, but mammalian host cells can also be used. In hosts such as yeasts, plants, or mammalian cells that ordinarily do not produce polyketides, it may be necessary to provide, also typically by recombinant means, suitable holo-ACP synthases to convert the recombinantly produced PKS to functionality. Provision of such enzymes is described, for example, in PCT publication Nos. WO 97/13845 and 98/27203, each of which is incorporated herein by reference.

The recombinant host cells of the invention can express all of the polyketide biosynthetic genes or only a subset of the same. For example, if only the genes for a PKS are expressed in a host cell that otherwise does not produce polyketide modifying enzymes (such as hydroxylation, epoxidation, or glycosylation enzymes) that can act on the polyketide produced, then the host cell produces unmodified polyketides, called macrolide aglycones. Such macrolide aglycones can be hydroxylated and glycosylated by adding them to the fermentation of a strain such as, for example, *Streptomyces antibioticus* or *Saccharopolyspora erythraea*, that contains the requisite modification enzymes.

There are a wide variety of diverse organisms that can modify macrolide aglycones to provide compounds with, or that can be readily modified to have, useful activities. For example, *Saccharopolyspora erythraea* can convert 6-dEB to a variety of useful compounds. The erythronolide 6-dEB is converted by the eryF gene product to erythronolide B, which is, in turn, glycosylated by the eryB gene product to obtain 3-O-mycarosylerythronolide B, which contains L-mycarose at C-3. The enzyme eryC gene product then converts this compound to erythromycin D by glycosylation with D-desosamine at C-5. Erythromycin D, therefore, differs from 6-dEB through glycosylation and by the addition of a hydroxyl group at C-6. Erythromycin D can be converted to erythromycin B in a reaction catalyzed by the eryG gene product by methylating the L-mycarose residue at C-3. Erythromcyin D is converted to erythromycin C by the addition of a hydroxyl group at C-12 in a reaction catalyzed by the eryK gene product. Erythromycin A is obtained from erythromycin C by methylation of the mycarose residue in a reaction catalyzed by the eryG gene product. The unmodified polyketides provided by the present invention, such as, for example, propyl-6-dEB are converted in *S. erythraea* to the corresponding derivatives of erythromycins A, B, C, and D. To ensure that only the desired compound is produced, one can use an *S. erythraea* eryA mutant that is unable to produce 6-dEB but can still carry out the desired conversions (Weber et al., 1985, *J. Bacteriol.* 164(1): 425–433). Another mutant strain useful in this regard is the KS1 null mutant strain that is typically employed in diketide feeding, as this strain is unable to produce erythromycins in the absence of added diketide. Also, one can employ other mutant strains, such as eryB, eryC, eryG, and/or eryK mutants, or mutant strains having mutations in multiple genes, to accumulate a preferred compound. The conversion can also be carried out in large fermentors for commercial production.

Moreover, there are other useful organisms that can be employed to hydroxylate and/or glycosylate the compounds of the invention. As described above, the organisms can be mutants unable to produce the polyketide normally produced in that organism, the fermentation can be carried out on plates or in large fermentors, and the compounds produced can be chemically altered after fermentation. Thus, *Streptomyces venezuelae*, which produces picromycin, contains enzymes that can transfer a desosaminyl group to the C-5 hydroxyl and a hydroxyl group to the C-12 position. In addition, S. venezuelae contains a glucosylation activity that glucosylates the 2'-hydroxyl group of the desosamine sugar. This latter modification reduces antibiotic activity, but the glucosyl residue is removed by enzymatic action prior to release of the polyketide from the cell. Another organism, S. narbonensis, contains the same modification enzymes as S. venezuelae, except the C-12 hydroxylase. Thus, the present invention provides the compounds produced by hydroxylation and glycosylation of the macrolide aglycones of the invention by action of the enzymes endogenous to S. narbonensis and S. venezuelae.

Other organisms suitable for making compounds of the invention include Micromonospora megalomicea, Streptomyces antibioticus, S. fradiae, and S. thermotolerans. M. megalomicea glycosylates the C-3 hydroxyl with mycarose, the C-5 hydroxyl with desosamine, and the C-6 hydroxyl with megosamine, and hydroxylates the C-6 position. S. antibioticus produces oleandomycin and contains enzymes that hydroxylate the C-6 and C-12 positions, glycosylate the C-3 hydroxyl with oleandrose and the C-5 hydroxyl with desosamine, and form an epoxide at C-8-C-8a. S. fradiae contains enzymes that glycosylate the C-5 hydroxyl with mycaminose and then the 4'-hydroxyl of mycaminose with mycarose, forming a disaccharide. S. thermotolerans contains the same activities as S. fradiae, as well as acylation activities. Thus, the present invention provides the compounds produced by hydroxylation and glycosylation of the macrolide aglycones of the invention by action of the enzymes endogenous to M. megalomicea, S. antibioticus, S. fradiae, and S. thermotolerans.

The present invention also provides methods and genetic constructs for producing the glycosylated and/or hydroxylated compounds of the invention directly in the host cell of interest. Thus, the genes that encode polyketide modification enzymes can be included in the host cells of the invention. Lack of adequate resistance to a polyketide can be overcome by providing the host cell with an MLS resistance gene (ermE and mgt/lrm, for example), which confers resistance to several 14-membered macrolides (see Cundliffe, 1989, Annu. Rev. Microbiol. 43:207–33; Jenkins and Cundliffe, 1991, Gene 108:55–62; and Cundliffe, 1992, Gene, 115:75–84, each of which is incorporated herein by reference).

The recombinant host cells of the invention can be used to produce polyketides (both macrolide aglycones and their modified derivatives) that are naturally occurring or produced by recombinant DNA technology. In one important embodiment, the recombinant host cells of the invention are used to produce hybrid PKS enzymes. For purposes of the invention, a hybrid PKS is a recombinant PKS that comprises all or part of one or more extender modules, loading module, and/or thioesterase/cyclase domain of a first PKS and all or part of one or more extender modules, loading module, and/or thioesterase/cyclase domain of a second PKS.

Those of skill in the art will recognize that all or part of either the first or second PKS in a hybrid PKS of the invention need not be isolated from a naturally occurring source. For example, only a small portion of an AT domain determines its specificity. See PCT patent application No. WO US99/15047, and Lau et al., infra, incorporated herein by reference. The state of the art in DNA synthesis allows the artisan to construct de novo DNA compounds of size sufficient to construct a useful portion of a PKS module or domain. Thus, the desired derivative coding sequences can be synthesized using standard solid phase synthesis methods such as those described by Jaye et al., 1984, J. Biol. Chem. 259: 6331, and instruments for automated synthesis are available commercially from, for example, Applied Biosystems, Inc. For purposes of the invention, such synthetic DNA compounds are deemed to be a portion of a PKS.

A hybrid PKS for purposes of the present invention can result not only:

(i) from fusions of heterologous domain (where heterologous means the domains in a module are derived from at least two different naturally occurring modules) coding sequences to produce a hybrid module coding sequence contained in a PKS gene whose product is incorporated into a PKS, but also:

(ii) from fusions of heterologous module (where heterologous module means two modules are adjacent to one another that are not adjacent to one another in naturally occurring PKS enzymes) coding sequences to produce a hybrid coding sequence contained in a PKS gene whose product is incorporated into a PKS, (iii) from expression of one or more PKS genes from a first PKS gene cluster with one or more PKS genes from a second PKS gene cluster, and (iv) from combinations of the foregoing.

Various hybrid PKSs of the invention illustrating these various alternatives are described herein.

Recombinant methods for manipulating modular PKS genes to make hybrid PKS enzymes are described in U.S. Pat. Nos. 5,672,491; 5,843,718; 5,830,750; and 5,712,146; and in PCT publication Nos. 98/49315 and 97/02358, each of which is incorporated herein by reference. A number of genetic engineering strategies have been used with DEBS to demonstrate that the structures of polyketides can be manipulated to produce novel natural products, primarily analogs of the erythromycins (see the patent publications referenced supra and Hutchinson, 1998, Curr Opin Microbiol. 1:319–329, and Baltz, 1998, Trends Microbiol. 6:76–83, incorporated herein by reference).

These techniques include: (i) deletion or insertion of modules to control chain length, (ii) inactivation of reduction/dehydration domains to bypass beta-carbon processing steps, (iii) substitution of AT domains to alter starter and extender units, (iv) addition of reduction/dehydration domains to introduce catalytic activities, and (v) substitution of ketoreductase KR domains to control hydroxyl stereochemistry. In addition, engineered blocked mutants of DEBS have been used for precursor directed biosynthesis of analogs that incorporate synthetically derived starter units. For example, more than 100 novel polyketides were produced by engineering single and combinatorial changes in multiple modules of DEBS. Hybrid PKS enzymes based on DEBS with up to three catalytic domain substitutions were constructed by cassette mutagenesis, in which various DEBS domains were replaced with domains from the rapamycin PKS (see Schweke et al., 1995, Proc. Nat. Acad. Sci. USA 92, 7839–7843, incorporated herein by reference) or one more of the DEBS KR domains was deleted. Functional single domain replacements or deletions were combined to generate DEBS enzymes with double and triple catalytic domain substitutions (see McDaniel et al., 1999, Proc. Nat. Acad. Sci. USA 96, 1846–1851, incorporated herein by reference).

Methods for generating libraries of polyketides have been greatly improved by cloning PKS genes as a set of three or more mutually selectable plasmids, each carrying a different wild-type or mutant PKS gene, then introducing all possible combinations of the plasmids with wild-type, mutant, and hybrid PKS coding sequences into the same host (see U.S. patent application Serial No. 60/129,731, filed Apr. 16, 1999, and PCT Pub. No. 98/27203, each of which is incorporated herein by reference). This method can also incorporate the use of a KS1° mutant, which by mutational biosynthesis can produce polyketides made from diketide starter units (see Jacobsen et al., 1997, *Science* 277, 367–369, incorporated herein by reference), as well as the use of a truncated gene that leads to 12-membered macrolides or an elongated gene that leads to 16-membered ketolides. Moreover, by utilizing in addition one or more vectors that encode glycosyl biosynthesis and transfer genes, such as those of the present invention for megosamine, desosamine, oleandrose, cladinose, and/or mycarose (in any combination), a large collection of glycosylated polyketides can be prepared.

The following table lists references describing illustrative PKS genes and corresponding enzymes that can be utilized in the construction of the recombinant hybrid PKSs and the corresponding DNA compounds that encode them. Also presented are various references describing tailoring enzymes and corresponding genes that can be employed in accordance with the methods of the invention.

Avermectin
  U.S. Pat. No. 5,252,474 to Merck.
  MacNeil et al., 1993, *Industrial Microorganisms: Basic and Applied Molecular Genetics*, Baltz, Hegeman, & Skatrud, eds. (ASM), pp. 245–256, A Comparison of the Genes Encoding the Polyketide Synthases for Avermectin, Erythromycin, and Nemadectin.
  MacNeil et al., 1992, *Gene* 115: 119–125, Complex Organization of the *Streptomyces avermitilis* genes encoding the avermectin polyketide synthase.
Candicidin (FR008)
  Hu et al., 1994, *Mol. Microbiol.* 14: 163–172.
Epothilone
  PCT patent publication No. WO US99/43653 to Kosan.
Erythromycin
  PCT Pub. No. 93/13663 to Abbott.
  U.S. Pat. No. 5,824,513 to Abbott.
  Donadio et al., 1991, *Science* 252:675–9.
  Cortes et al., Nov. 8, 1990, *Nature* 348:176–8, An unusually large multifunctional polypeptide in the erythromycin producing polyketide synthase of *Saccharopolyspora erythraea*.
  Glycosylation Enzymes
  PCT Pat. App. Pub. No. 97/23630 to Abbott.
FK-506
  Motamedi et al., 1998, The biosynthetic gene cluster for the macrolactone ring of the immunosuppressant FK506, *Eur. J. biochem.* 256: 528–534.
  Motamedi et al., 1997, Structural organization of a multifunctional polyketide synthase involved in the biosynthesis of the macrolide immunosuppressant FK506, *Eur. J. Biochem.* 244: 74–80.
  Methyltransferase
  U.S. Pat. No. 5,264,355, issued Nov. 23, 1993, Methylating enzyme from Streptomyces MA6858. 31-O-desmethyl-FK506 methyltransferase.
  Motamedi et al., 1996, Characterization of methyltransferase and hydroxylase genes involved in the biosynthesis of the immunosuppressants FK506 and FK520, *J. Bacteriol.* 178: 5243–5248.
FK-520
  PCT patent publication No. WO US00/020601 to Kosan.
  See also Nielsen et al., 1991, *Biochem.* 30:5789–96 (enzymology of pipecolate incorporation).
Lovastatin
  U.S. Pat. No. 5,744,350 to Merck.
Narbomycin (and Picromycin)
  PCT patent publication No. WO US99/61599 to Kosan.
Nemadectin
  MacNeil et al., 1993, supra.
Niddamycin
  Kakavas et al., 1997, Identification and characterization of the niddamycin polyketide synthase genes from *Streptomyces caelestis*, *J. Bacteriol.* 179: 7515–7522.
Oleandomycin
  Swan et al., 1994, Characterisation of a *Streptomyces antibioticus* gene encoding a type I polyketide synthase which has an unusual coding sequence, *Mol. Gen. Genet.* 242: 358–362.
  PCT patent publication No. WO US00/026349 to Kosan.
  Olano et al., 1998, Analysis of a *Streptomyces antibioticus* chromosomal region involved in oleandomycin biosynthesis, which encodes two glycosyltransferases responsible for glycosylation of the macrolactone ring, *Mol. Gen. Genet.* 259(3): 299–308.
Platenolide
  EP Pat. App. Pub. No. 791,656 to Lilly.
Rapamycin
  Schwecke et al., August 1995, The biosynthetic gene cluster for the polyketide rapamycin, *Proc. Natl. Acad. Sci. USA* 92:7839–7843.
  Aparicio et al., 1996, Organization of the biosynthetic gene cluster for rapamycin in *Streptomyces hygroscopicus*: analysis of the enzymatic domains in the modular polyketide synthase, *Gene* 169: 9–16.
Rifamycin
  August et al., Feb. 13, 1998, Biosynthesis of the ansamycin antibiotic rifamycin: deductions from the molecular analysis of the rif biosynthetic gene cluster of *Amycolatopsis mediterranei* S669, *Chemistry & Biology*, 5(2): 69–79.
Soraphen
  U.S. Pat. No. 5,716,849 to Novartis.
  Schupp et al., 1995, *J. Bacteriology* 177: 3673–3679. A *Sorangium cellulosum* (Myxobacterium) Gene Cluster for the Biosynthesis of the Macrolide Antibiotic Soraphen A: Cloning, Characterization, and Homology to Polyketide Synthase Genes from Actinomycetes.
Spiramycin
  U.S. Pat. No. 5,098,837 to Lilly.
  Activator Gene
  U.S. Pat. No. 5,514,544 to Lilly.
Tylosin
  EP Pub. No. 791,655 to Lilly.
  Kuhstoss et al., 1996, *Gene* 183:231–6., Production of a novel polyketide through the construction of a hybrid polyketide synthase.
  U.S. Pat. No. 5,876,991 to Lilly.
  Tailoring enzymes
  Merson-Davies and Cundliffe, 1994, *Mol. Microbiol.* 13: 349–355. Analysis of five tylosin biosynthetic genes from the tylBA region of the *Streptomyces fradiae* genome.

As the above Table illustrates, there are a wide variety of PKS genes that serve as readily available sources of DNA and sequence information for use in constructing the hybrid PKS-encoding DNA compounds of the invention.

In constructing hybrid PKSs, certain general methods may be helpful. For example, it is often beneficial to retain the framework of the module to be altered to make the hybrid PKS. Thus, if one desires to add DH and ER functionalities to a module, it is often preferred to replace the KR domain of the original module with a KR, DH, and ER domain-containing segment from another module, instead of merely inserting DH and ER domains. One can alter the stereochemical specificity of a module by replacement of the KS domain with a KS domain from a module that specifies a different stereochemistry. See Lau et al., 1999, "Dissecting the role of acyltransferase domains of modular polyketide synthases in the choice and stereochemical fate of extender units" *Biochemistry* 38(5):1643–1651, incorporated herein by reference. One can alter the specificity of an AT domain by changing only a small segment of the domain. See Lau et al., supra. One can also take advantage of known linker regions in PKS proteins to link modules from two different PKSs to create a hybrid PKS. See Gokhale et al., Apr. 16, 1999, Dissecting and Exploiting Intermodular Communication in Polyketide Synthases", *Science* 284: 482–485, incorporated herein by reference.

The hybrid PKS-encoding DNA compounds can be and often are hybrids of more than two PKS genes. Even where only two genes are used, there are often two or more modules in the hybrid gene in which all or part of the module is derived from a second (or third) PKS gene.

There are at least five degrees of freedom for constructing a hybrid PKS in terms of the polyketide that will be produced. First, the polyketide chain length is determined by the number of extender modules in the PKS, and the present invention includes hybrid PKSs that contain 6, as wells as fewer or more than 6, extender modules. Second, the nature of the carbon skeleton of the PKS is determined by the specificities of the acyl transferases that determine the nature of the extender units at each position, e.g., malonyl, methylmalonyl, ethylmalonyl, or other substituted malonyl. Third, the loading module specificity also has an effect on the resulting carbon skeleton of the polyketide. The loading module may use a different starter unit, such as acetyl, butyryl, and the like. As noted above, another method for varying loading module specificity involves inactivating the KS activity in extender module 1 (KS1) and providing alternative substrates, called diketides, that are chemically synthesized analogs of extender module 1 diketide products, for extender module 2. This approach was illustrated in PCT publication Nos. 97/02358 and 99/03986, incorporated herein by reference, wherein the KS1 activity was inactivated through mutation. Fourth, the oxidation state at various positions of the polyketide will be determined by the dehydratase and reductase portions of the modules. This will determine the presence and location of ketone and alcohol moieties and C—C double bonds or C—C single bonds in the polyketide. Finally, the stereochemistry of the resulting polyketide is a function of three aspects of the synthase. The first aspect is related to the AT/KS specificity associated with substituted malonyls as extender units, which affects stereochemistry only when the reductive cycle is missing or when it contains only a ketoreductase, as the dehydratase would abolish chirality. Second, the specificity of the ketoreductase may determine the chirality of any beta-OH. Finally, the enoylreductase specificity for substituted malonyls as extender units may influence the stereochemistry when there is a complete KR/DH/ER available.

Thus, the modular PKS systems generally permit a wide range of polyketides to be synthesized. As compared to the aromatic PKS systems, the modular PKS systems accept a wider range of starter units, including aliphatic monomers (acetyl, propionyl, butyryl, isovaleryl, etc.), aromatics (aminohydroxybenzoyl), alicyclics (cyclohexanoyl), and heterocyclics (thiazolyl). Certain modular PKSs have relaxed specificity for their starter units (Kao et al., 1994, *Science*, supra). Modular PKSs also exhibit considerable variety with regard to the choice of extender units in each condensation cycle. The degree of beta-ketoreduction following a condensation reaction can be altered by genetic manipulation (Donadio et al., 1991, *Science*, supra; Donadio et al., 1993, *Proc. Natl. Acad. Sci. USA* 90: 7119–7123). Likewise, the size of the polyketide product can be varied by designing mutants with the appropriate number of modules (Kao et al., 1994, *J. Am. Chem. Soc.* 116:11612–11613). Lastly, modular PKS enzymes are particularly well known for generating an impressive range of asymmetric centers in their products in a highly controlled manner. The polyketides, antibiotics, and other compounds produced by the methods of the invention are typically single stereoisomeric forms. Although the compounds of the invention can occur as mixtures of stereoisomers, it may be beneficial in some instances to generate individual stereoisomers. Thus, the combinatorial potential within modular PKS pathways based on any naturally occurring modular PKS scaffold is virtually unlimited.

While hybrid PKSs are most often produced by "mixing and matching" portions of PKS coding sequences, mutations in DNA encoding a PKS can also be used to introduce, alter, or delete an activity in the encoded polypeptide. Mutations can be made to the native sequences using conventional techniques. The substrates for mutation can be an entire cluster of genes or only one or two of them; the substrate for mutation may also be portions of one or more of these genes. Techniques for mutation include preparing synthetic oligonucleotides including the mutations and inserting the mutated sequence into the gene encoding a PKS subunit using restriction endonuclease digestion. See, e.g., Kunkel, 1985, *Proc. Natl. Acad. Sci. USA* 82: 448; Geisselsoder et al., 1987, *BioTechniques* 5:786. Alternatively, the mutations can be effected using a mismatched primer (generally 10–20 nucleotides in length) that hybridizes to the native nucleotide sequence, at a temperature below the melting temperature of the mismatched duplex. The primer can be made specific by keeping primer length and base composition within relatively narrow limits and by keeping the mutant base centrally located. See Zoller and Smith, 1983, *Methods Enzymol.* 100:468. Primer extension is effected using DNA polymerase, the product cloned, and clones containing the mutated DNA, derived by segregation of the primer extended strand, selected. Identification can be accomplished using the mutant primer as a hybridization probe. The technique is also applicable for generating multiple point mutations. See, e.g., Dalbie-McFarland et al., 1982, *Proc. Natl. Acad. Sci. USA* 79: 6409. PCR mutagenesis can also be used to effect the desired mutations.

Random mutagenesis of selected portions of the nucleotide sequences encoding enzymatic activities can also be accomplished by several different techniques known in the art, e.g., by inserting an oligonucleotide linker randomly into a plasmid, by irradiation with X-rays or ultraviolet light, by incorporating incorrect nucleotides during in vitro DNA synthesis, by error-prone PCR mutagenesis, by preparing synthetic mutants, or by damaging plasmid DNA in vitro with chemicals. Chemical mutagens include, for example, sodium bisulfite, nitrous acid, nitrosoguanidine, hydroxylamine, agents which damage or remove bases thereby preventing normal base-pairing such as hydrazine or formic acid, analogues of nucleotide precursors such as 5-bromouracil, 2-aminopurine, or acridine intercalating agents such as proflavine, acriflavine, quinacrine, and the like. Generally, plasmid DNA or DNA fragments are treated with chemical mutagens, transformed into *E. coli* and propagated as a pool or library of mutant plasmids.

In constructing a hybrid PKS of the invention, regions encoding enzymatic activity, i.e., regions encoding corresponding activities from different PKS synthases or from different locations in the same PKS, can be recovered, for example, using PCR techniques with appropriate primers. By "corresponding" activity encoding regions is meant those regions encoding the same general type of activity. For example, a KR activity encoded at one location of a gene cluster "corresponds" to a KR encoding activity in another location in the gene cluster or in a different gene cluster. Similarly, a complete reductase cycle could be considered corresponding. For example, KR/DH/ER can correspond to a KR alone.

If replacement of a particular target region in a host PKS is to be made, this replacement can be conducted in vitro using suitable restriction enzymes. The replacement can also be effected in vivo using recombinant techniques involving homologous sequences framing the replacement gene in a donor plasmid and a receptor region in a recipient plasmid. Such systems, advantageously involving plasmids of differing temperature sensitivities are described, for example, in PCT publication No. WO 96/40968, incorporated herein by reference. The vectors used to perform the various operations to replace the enzymatic activity in the host PKS genes or to support mutations in these regions of the host PKS genes can be chosen to contain control sequences operably linked to the resulting coding sequences in a manner such that expression of the coding sequences can be effected in an appropriate host.

However, simple cloning vectors may be used as well. If the cloning vectors employed to obtain PKS genes encoding derived PKS lack control sequences for expression operably linked to the encoding nucleotide sequences, the nucleotide sequences are inserted into appropriate expression vectors. This need not be done individually, but a pool of isolated encoding nucleotide sequences can be inserted into expression vectors, the resulting vectors transformed or transfected into host cells, and the resulting cells plated out into individual colonies. The invention provides a variety of recombinant DNA compounds in which the various coding sequences for the domains and modules of the PKS are flanked by non-naturally occurring restriction enzyme recognition sites.

The various PKS nucleotide sequences can be cloned into one or more recombinant vectors as individual cassettes, with separate control elements, or under the control of, e.g., a single promoter. The PKS subunit encoding regions can include flanking restriction sites to allow for the easy deletion and insertion of other PKS subunit encoding sequences so that hybrid PKSs can be generated. The design of such unique restriction sites is known to those of skill in the art and can be accomplished using the techniques described above, such as site-directed mutagenesis and PCR.

The expression vectors containing nucleotide sequences encoding a variety of PKS enzymes for the production of different polyketides are then transformed into the appropriate host cells to construct the library. In one straightforward approach, a mixture of such vectors is transformed into the selected host cells and the resulting cells plated into individual colonies and selected to identify successful transformants. Each individual colony has the ability to produce a particular PKS synthase and ultimately a particular polyketide. Typically, there will be duplications in some, most, or all of the colonies; the subset of the transformed colonies that contains a different PKS in each member colony can be considered the library. Alternatively, the expression vectors can be used individually to transform hosts, which transformed hosts are then assembled into a library. A variety of strategies are available to obtain a multiplicity of colonies each containing a PKS gene cluster derived from the naturally occurring host gene cluster so that each colony in the library produces a different PKS and ultimately a different polyketide. The number of different polyketides that are produced by the library is typically at least four, more typically at least ten, and preferably at least 20, and more preferably at least 50, reflecting similar numbers of different altered PKS gene clusters and PKS gene products. The number of members in the library is arbitrarily chosen; however, the degrees of freedom outlined above with respect to the variation of starter, extender units, stereochemistry, oxidation state, and chain length enables the production of quite large libraries.

Methods for introducing the recombinant vectors of the invention into suitable hosts are known to those of skill in the art and typically include the use of $CaCl_2$ or agents such as other divalent cations, lipofection, DMSO, protoplast transformation, infection, transfection, and electroporation. The polyketide producing colonies can be identified and isolated using known techniques and the produced polyketides further characterized. The polyketides produced by these colonies can be used collectively in a panel to represent a library or may be assessed individually for activity.

The libraries of the invention can thus be considered at four levels: (1) a multiplicity of colonies each with a different PKS encoding sequence; (2) the proteins produced from the coding sequences; (3) the polyketides produced from the proteins assembled into a function PKS; and (4) antibiotics or compounds with other desired activities derived from the polyketides.

Colonies in the library are induced to produce the relevant synthases and thus to produce the relevant polyketides to obtain a library of polyketides. The polyketides secreted into the media can be screened for binding to desired targets, such as receptors, signaling proteins, and the like. The supernatants per se can be used for screening, or partial or complete purification of the polyketides can first be effected. Typically, such screening methods involve detecting the binding of each member of the library to receptor or other target ligand. Binding can be detected either directly or through a competition assay. Means to screen such libraries for binding are well known in the art. Alternatively, individual polyketide members of the library can be tested against a desired target. In this event, screens wherein the biological response of the target is measured can more readily be included. Antibiotic activity can be verified using typical screening assays such as those set forth in Lehrer et al., 1991, *J. Immunol. Meth.* 137:167–173, incorporated herein by reference, and in the Examples below.

The invention provides methods for the preparation of a large number of polyketides. These polyketides are useful intermediates in formation of compounds with antibiotic or other activity through hydroxylation, epoxidation, and glycosylation reactions as described above. In general, the polyketide products of the PKS must be further modified, typically by hydroxylation and glycosylation, to exhibit antibiotic activity. Hydroxylation results in the novel polyketides of the invention that contain hydroxyl groups at C-6, which can be accomplished using the hydroxylase encoded by the eryF gene, and/or C-12, which can be accomplished using the hydroxylase encoded by the picK or eryK gene. Also, the oleP gene is available in recombinant form, which can be used to express the oleP gene product in any host cell. A host cell, such as a Streptomyces host cell or a *Saccharopolyspora erythraea* host cell, modified to express the oleP gene thus can be used to produce polyketides comprising the C-8-C-8a epoxide present in oleandomycin. Thus the invention provides such modified polyketides. The presence of hydroxyl groups at these positions can enhance the antibiotic activity of the resulting compound relative to its unhydroxylated counterpart.

Methods for glycosylating the polyketides are generally known in the art; the glycosylation may be effected intracellularly by providing the appropriate glycosylation enzymes or may be effected in vitro using chemical synthetic means as described herein and in PCT publication No. WO 98/49315, incorporated herein by reference. Preferably, glycosylation with desosamine, mycarose, and/or megosamine is effected in accordance with the methods of the invention in recombinant host cells provided by the invention. In general, the approaches to effecting glycosylation mirror those described above with respect to hydroxylation. The purified enzymes, isolated from native sources or recombinantly produced may be used in vitro. Alternatively and as noted, glycosylation may be effected intracellularly using endogenous or recombinantly produced intracellular glycosylases. In addition, synthetic chemical methods may be employed.

The antibiotic modular polyketides may contain any of a number of different sugars, although D-desosamine, or a close analog thereof, is most common. Erythromycin, picromycin, megalomicin, narbomycin, and methymycin contain desosamine. Erythromycin also contains L-cladinose (3-O-methyl mycarose). Tylosin contains mycaminose (4-hydroxy desosamine), mycarose and 6-deoxy-D-allose. 2-acetyl-1-bromodesosamine has been used as a donor to glycosylate polyketides by Masamune et al., 1975, *J. Am. Chem. Soc.* 97: 3512–3513. Other, apparently more stable donors include glycosyl fluorides, thioglycosides, and trichloroacetimidates; see Woodward et al., 1981, *J. Am. Chem. Soc.* 103: 3215; Martin et al., 1997, *J. Am. Chem. Soc.* 119: 3193; Toshima et al., 1995, *J. Am. Chem. Soc.* 117: 3717; Matsumoto et al., 1988, *Tetrahedron Lett.* 29: 3575. Glycosylation can also be effected using the polyketide aglycones as starting materials and using *Saccharopolyspora erythraea* or *Streptomyces venezuelae* or other host cell to make the conversion, preferably using mutants unable to synthesize macrolides, as discussed above.

Thus, a wide variety of polyketides can be produced by the hybrid PKS enzymes of the invention. These polyketides are useful as antibiotics and as intermediates in the synthesis of other useful compounds. In one important aspect, the invention provides methods for making antibiotic compounds related in structure to erythromycin, a potent antibiotic compound. The invention also provides novel ketolide compounds, polyketide compounds with potent antibiotic activity of significant interest due to activity against antibiotic resistant strains of bacteria. See Griesgraber et al., 1996, *J. Antibiot.* 49: 465–477, incorporated herein by reference. Most if not all of the ketolides prepared to date are synthesized using erythromycin A, a derivative of 6-dEB, as an intermediate. See Griesgraber et al., supra; Agouridas et al., 1998, *J. Med. Chem.* 41: 4080–4100, U.S. Pat. Nos. 5,770,579; 5,760,233; 5,750,510; 5,747,467; 5,747,466; 5,656,607; 5,635,485; 5,614,614; 5,556,118; 5,543,400; 5,527,780; 5,444,051; 5,439,890; 5,439,889; and PCT publication Nos. WO 98/09978 and 98/28316, each of which is incorporated herein by reference.

As noted above, the hybrid PKS genes of the invention can be expressed in a host cell that contains the desosamine, megosamine, and/or mycarose biosynthetic genes and corresponding transferase genes as well as the required hydroxylase gene(s), which may be either pick, megK, or eryK (for the C-12 position) and/or megF or eryF (for the C-6 position). The resulting compounds have antibiotic activity but can be further modified, as described in the patent publications referenced above, to yield a desired compound with improved or otherwise desired properties. Alternatively, the aglycone compounds can be produced in the recombinant host cell, and the desired glycosylation and hydroxylation steps carried out in vitro or in vivo, in the latter case by supplying the converting cell with the aglycone, as described above.

As described above, there are a wide variety of diverse organisms that can modify compounds such as those described herein to provide compounds with or that can be readily modified to have useful activities. For example, *Saccharopolyspora erythraea* can convert 6-dEB to a variety of useful compounds. The compounds provided by the present invention can be provided to cultures of *Saccharopolyspora erythraea* and converted to the corresponding derivatives of erythromycins A, B, C, and D. To ensure that only the desired compound is produced, one can use an *S. erythraea* eryA mutant that is unable to produce 6-dEB but can still carry out the desired conversions (Weber et al., 1985, *J. Bacteriol.* 164(1): 425–433). Also, one can employ other mutant strains, such as eryB, eryC, eryG, and/or eryK mutants, or mutant strains having mutations in multiple genes, to accumulate a preferred compound. The conversion can also be carried out in large fermentors for commercial production. Each of the erythromycins A, B, C, and D has antibiotic activity, although erythromycin A has the highest antibiotic activity. Moreover, each of these compounds can form, under treatment with mild acid, a C-6 to C-9 hemiketal with motilide activity. For formation of hemiketals with motilide activity, erythromycins B, C, and D, are preferred, as the presence of a C-12 hydroxyl allows the formation of an inactive compound that has a hemiketal formed between C-9 and C-12.

Thus, the present invention provides the compounds produced by hydroxylation and glycosylation of the compounds of the invention by action of the enzymes endogenous to *Saccharopolyspora erythraea* and mutant strains of *S. erythraea*. Such compounds are useful as antibiotics or as motilides directly or after chemical modification. For use as antibiotics, the compounds of the invention can be used directly without further chemical modification. Erythromycins A, B, C, and D all have antibiotic activity, and the corresponding compounds of the invention that result from the compounds being modified by *Saccharopolyspora erythraea* also have antibiotic activity. These compounds can be chemically modified, however, to provide other compounds of the invention with potent antibiotic activity. For example, alkylation of erythromycin at the C-6 hydroxyl can be used to produce potent antibiotics (clarithromycin is C-6-O-methyl), and other useful modifications are described in, for example, Griesgraber et al., 1996, *J. Antibiot.* 49: 465–477, Agouridas et al., 1998, *J. Med. Chem.* 41: 4080–4100, U.S. Pat. Nos. 5,770,579; 5,760,233; 5,750,510; 5,747,467; 5,747,466; 5,656,607; 5,635,485; 5,614,614; 5,556,118; 5,543,400; 5,527,780; 5,444,051; 5,439,890; and 5,439,889; and PCT publication Nos. WO 98/09978 and 98/28316, each of which is incorporated herein by reference.

For use as motilides, the compounds of the invention can be used directly without further chemical modification. Erythromycin and certain erythromycin analogs are potent agonists of the motilin receptor that can be used clinically as prokinetic agents to induce phase III of migrating motor complexes, to increase esophageal peristalsis and LES pressure in patients with GERD, to accelerate gastric emptying in patients with gastric paresis, and to stimulate gall bladder contractions in patients after gallstone removal and in diabetics with autonomic neuropathy. See Peeters, 1999, Motilide Web Site, http://www.med.kuleuven.ac.be/med/gih/motilid.htm, and Omura et al., 1987, Macrolides with gastrointestinal motor stimulating activity, *J. Med. Chem.* 30: 1941–3). The corresponding compounds of the invention that result from the compounds of the invention being modified by *Saccharopolyspora erythraea* also have motilide activity, particularly after conversion, which can also occur in vivo, to the C-6 to C-9 hemiketal by treatment with mild acid. Compounds lacking the C-12 hydroxyl are especially preferred for use as motilin agonists. These compounds can also be further chemically modified, however, to provide other compounds of the invention with potent motilide activity.

Moreover, and also as noted above, there are other useful organisms that can be employed to hydroxylate and/or glycosylate the compounds of the invention. As described above, the organisms can be mutants unable to produce the polyketide normally produced in that organism, the fermentation can be carried out on plates or in large fermentors, and the compounds produced can be chemically altered after fermentation. In addition to *Saccharopolyspora erythraea, Streptomyces venezuelae, S. narbonensis, S. antibioticus, Micromonospora megalomicea, S. fradiae,* and *S. thermotolerans* can also be used. In addition to antibiotic activity, compounds of the invention produced by treatment with *M megalomicea* enzymes can have antiparasitic activity as well. Thus, the present invention provides the compounds produced by hydroxylation and glycosylation by action of the enzymes endogenous to *S. erythraea, S. venezuelae, S. narbonensis, S. antibioticus, M. megalomicea, S. fradiae,* and *S. thermotolerans.*

The compounds of the invention can be isolated from the fermentation broths of these cultured cells and purified by standard procedures. The compounds can be readily formulated to provide the pharmaceutical compositions of the invention. The pharmaceutical compositions of the invention can be used in the form of a pharmaceutical preparation, for example, in solid, semisolid, or liquid form. This preparation will contain one or more of the compounds of the invention as an active ingredient in admixture with an organic or inorganic carrier or excipient suitable for external, enteral, or parenteral application. The active ingredient may be compounded, for example, with the usual non-toxic, pharmaceutically acceptable carriers for tablets, pellets, capsules, suppositories, solutions, emulsions, suspensions, and any other form suitable for use.

The carriers which can be used include water, glucose, lactose, gum acacia, gelatin, mannitol, starch paste, magnesium trisilicate, talc, corn starch, keratin, colloidal silica, potato starch, urea, and other carriers suitable for use in manufacturing preparations, in solid, semi-solid, or liquified form. In addition, auxiliary stabilizing, thickening, and coloring agents and perfumes may be used. For example, the compounds of the invention may be utilized with hydroxypropyl methylcellulose essentially as described in U.S. Pat. No. 4,916,138, incorporated herein by reference, or with a surfactant essentially as described in EPO patent publication No. 428,169, incorporated herein by reference.

Oral dosage forms may be prepared essentially as described by Hondo et al., 1987, *Transplantation Proceedings* XIX, Supp. 6: 17–22, incorporated herein by reference. Dosage forms for external application may be prepared essentially as described in EPO patent publication No. 423,714, incorporated herein by reference. The active compound is included in the pharmaceutical composition in an amount sufficient to produce the desired effect upon the disease process or condition.

For the treatment of conditions and diseases caused by infection, a compound of the invention may be administered orally, topically, parenterally, by inhalation spray, or rectally in dosage unit formulations containing conventional non-toxic pharmaceutically acceptable carriers, adjuvant, and vehicles. The term parenteral, as used herein, includes subcutaneous injections, and intravenous, intramuscular, and intrasternal injection or infusion techniques.

Dosage levels of the compounds of the invention are of the order from about 0.01 mg to about 50 mg per kilogram of body weight per day, preferably from about 0.1 mg to about 10 mg per kilogram of body weight per day. The dosage levels are useful in the treatment of the above-indicated conditions (from about 0.7 mg to about 3.5 mg per patient per day, assuming a 70 kg patient). In addition, the compounds of the invention may be administered on an intermittent basis, i.e., at semi-weekly, weekly, semi-monthly, or monthly intervals.

The amount of active ingredient that may be combined with the carrier materials to produce a single dosage form will vary depending upon the host treated and the particular mode of administration. For example, a formulation intended for oral administration to humans may contain from 0.5 mg to 5 mg of active agent compounded with an appropriate and convenient amount of carrier material, which may vary from about 5 percent to about 95 percent of the total composition. Dosage unit forms will generally contain from about 0.5 mg to about 500 mg of active ingredient. For external administration, the compounds of the invention may be formulated within the range of, for example, 0.00001% to 60% by weight, preferably from 0.001% to 10% by weight, and most preferably from about 0.005% to 0.8% by weight.

It will be understood, however, that the specific dose level for any particlular patient will depend on a variety of factors. These factors include the activity of the specific compound employed; the age, body weight, general health, sex, and diet of the subject; the time and route of administration and the rate of excretion of the drug; whether a drug combination is employed in the treatment; and the severity of the particular disease or condition for which therapy is sought.

A detailed description of the invention having been provided above, the following examples are given for the purpose of illustrating the present invention and shall not be construed as being a limitation on the scope of the invention or claims.

EXAMPLE 1

Construction of eryM Knockout Strains and Production of 15-Methyl-erythromycins

This example describes the construction of two recombinant DNA vectors designed to disrupt the eryM gene in *Saccharopolyspora erythraea* by single crossover. These vectors can be used to generate a strain of *S. erythraea* that produces higher titers of 15-methyl erythromycin A or C than does wild-type *S. erythraea* under the same conditions without the need for the addition of an exogenous diketide. The desired strain differs from the wild-type strain in that intracellular pools of propanoyl-CoA are greatly reduced, pools of butanoyl-CoA are greatly elevated, and pools of methylmalonyl-CoA remain high. It has been shown in vitro that 6-dEB synthase accepts butanoyl-CoA as the starter equally efficiently as propanoyl-CoA (Pieper et al., 1996, *Biochemistry* 35:2054). It has been reported that disruption of the eryM gene, which encodes methylmalonyl decarboxylase, causes loss of erythromycin production that can be restored by feeding propionate, methylpropionate, or propanol in a wild-type strain of *S. erythraea* (Hsieh and Kolattukudy, 1994, *J. Bact.* 176:714). This results suggests that the EryM decarboxylase catalyzes the primary flux from methylmalonyl CoA to propionyl CoA. This example shows how to disrupt eryM by single-crossover for illustrative purposes. Preferred strains of the invention are modified by deletion of the eryM gene by double crossover, leaving no marker in the chromosome.

The *Saccharopolyspora erythraea* eryM gene was isolated by PCR of the coding region. The cloning vectors pWHM3 and pOJ260 are well-known Streptomyces vectors. An internal fragment of the eryM gene was isolated by PCR and cloned into the XbaI and HindIII sites of the vectors pWHM3 (confers thiostrepton resistance) and pOJ260 (confers apramycin resistance) for gene disruption. The resulting vectors were propagated in *E. coli* ET12567 to obtain unmethylated DNA. The eryM gene sequence showing the engineered XbaI and native HindIII sites used to clone the internal fragment into the vectors is shown in FIGS. 3A–C. The XbaI site introduces a stop codon into the reading frame, ensuring that insertion by homologous recombination will disrupt the gene.

The above constructs were then introduced into a high-producing *Saccharopolyspora erythraea* strain for gene disruption by homologous recombination. Protoplast transformation of this strain was very difficult, transformants were only obtained only using alkali-denatured, non-methylated DNA of only the pOJ260-derived construct. The transformant strains were grown in TSB for DNA isolation and in a standard two-stage shake flask fermentation procedure to evaluate production (two days growth in vegetative medium, 10% crossing volume into fermentation medium and daily feeds of 0.6% soy oil and 40 mM propanol over nine days). Metabolites were quantitated by ion counting in a mass spectrometer relative to a roxithromycin internal standard.

Putative eryM knockout transform ants were shown to be correct by Southern blot hybridization. The mutant displayed the same morphology as the parent strain, both in liquid medium and on agar plates (i.e., gray colonies with brown pigment in agar).

Figure 4:
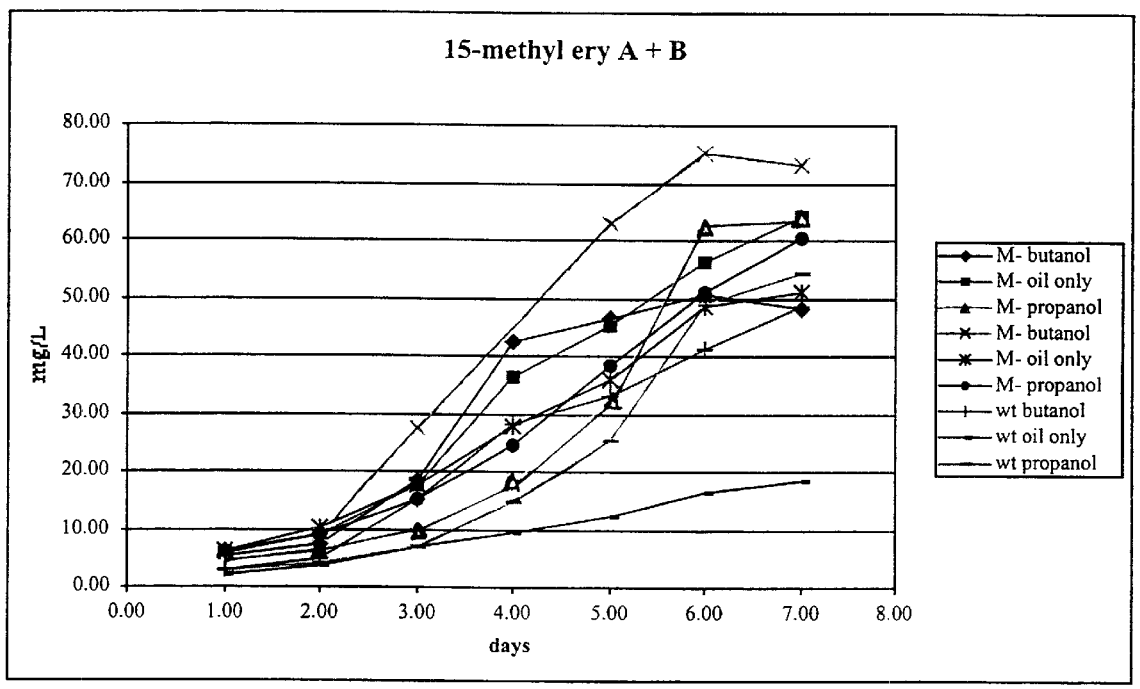
FIG. 4 shows production of 15-methyl erythromycin A and B by a wild type *Saccharopolyspora erythraea* strain and two isolates of the *Saccharopolyspora erythraea* eryM⁻ mutant as described in Example 1.

The parent strain and two isolates of the eryM⁻ mutant were grown using the shake flask procedure. In addition to the oil plus propanol feed, culture flasks were fed equivalent levels of oil alone, oil plus butanol, oil plus propionate, and oil plus butyrate. The cultures were killed by the propionate and butyrate feeds, and these flasks were discarded. Samples were taken from the other flasks each day and the set was analyzed by ion counting. The results are shown graphically below. The first graph shows a time-course of production of erythromycins A and B for the wild-type and mutant strains with the different feeding regimes. The second graph shows the same for 15-methyl-erythromycins A and B (FIG. 4). The ion count at 748.6 amu is not all due to 15-methyl-erythromycin A. LC-MS analysis of ethyl acetate extracts of day 7 samples fed oil alone or oil and butanol suggested that only about 10% of the 748.6 peak was 15-methyl-erythromycin A. The exact amount of PrEryA produced by the strains remains to be determined.

Another fermentation experiment was performed using a lighter medium with the oil omitted to evaluate a wider range of feeding regimes. The results did not show a clear trend, except that the oil feed is beneficial to good production for both strains. Esters of propionate or butyrate, instead of the corresponding alcohols, could also be fed but produced no substantial improvement.

Because overexpression of crotonyl CoA reductase can increase butyryl CoA levels, the *Streptomyces coelicolor* ccr gene could be used to replace the eryM gene, i.e., with an expression cassette for ccr overexpression. Because overexpression of propionyl CoA carboxylase (pcc) can reduce propionyl CoA levels, a similar construct for overexpression of pcc could also be used advantageously with the methods and recombinant strains of the present invention. In addition, in those strains that contain a methylmalonyl CoA transcarboxylase that decarboxylates methylmalonyl CoA to propionyl CoA (putative homologues of both subunits of this enzyme are in the *S. coelicolor* genome), one could disrupt the corresponding gene to improve production.

Production of erythromycin A and B by the eryM⁻ mutant is similar to that of the corresponding wild-type strain when fed oil alone or oil and propanol in rich medium. For both strains, production of erythromycin A and B was depressed with an oil and butanol feed. While knockout of eryM does not reduce production of erythromycin A and B in rich medium in the dramatic way reported by Hsieh & Kolattukudy, the rich medium used (which is necessary for high level production) probably masks the effect of the eryM knockout.

The high-producing wild-type strain appeared to produce low levels of 15-methyl-erythromycins when butanol is fed instead of propanol. Thus, in one aspect the present invention provides a method for producing 15-methyl-erythromycins by feeding a culture of erythromycin-producing cells by culturing said cells in a medium containing butanol. If the ion count at 748.6 amu for the culture fed oil and propanol is subtracted as background, the oil and butanol feed causes 15-methyl-erythromycin A and B production at up to 5% of the total erythromycin production, although the actual amount of 15-methyl-erythromycin A and B is probably much lower. The eryM⁻ mutant produced a higher maximum percentage 15-methyl-erythromycin A and B (~15%) with an oil and butanol feed compared to the wild-type strain, demonstrating that propionyl CoA levels are reduced in the eryM⁻ strain and confirming that the methods of the present invention can be used to increase production of 15-methyl-erythromycins.

EXAMPLE 2

Construction of a Loading Domain for a DEBS PKS

While Example 1 illustrates the aspect of the invention in which butyryl CoA is loaded by the loading domain of DEBS to produce 15-methyl-6-deoxyerythronolide B, this and the following Example illustrate an alternative aspect of the invention, in which a recombinant PKS that comprises an altered loading domain is used to produce the compound. This altered loading domain can be employed with any number of extender modules from any one or more PKS. In a preferred embodiment, the loading domain is used in conjunction with the six extender modules of DEBS, or the oleandolide PKS (see PCT patent publication No. WO 00/026349, incorporated herein by reference), or the megalomicin PKS (see U.S. patent application Serial No. 60/190, 024, filed Mar. 17, 2000, and the application Ser. No. 09/679,279, filed Oct. 4, 2000, naming the same inventors and claiming priority to the former applicaton, each of which is incorporated herein by reference), to produce 15-methyl-erythromycins in *Saccharopolyspora erythraea* host cells.

An illustrative hybrid PKS of the invention is made by replacing the AT domain of the loading module of the oleandomycin PKS with the ethylmalonyl-CoA specifying AT domain of the fourth extender module of the FK520 PKS. The resulting hybrid PKS contains the KSQ domain and downstream interdomain region of OleA1 (aa 1–562) fused to the FKAT4 domain (aa 562–896) fused to the OleA1 AT-ACP interdomain region, adjoining OleA1 ACP of the loading domain and the remainder of the OlePKS (897–end). The amino acid sequence of the hybrid portion of this PKS is shown in FIGS. 10A–C.

Another illustrative hybrid PKS of the invention is made by fusing the following in order specified: the first 9 aa of OleAI (1–9 in sequence below); 846 aa of the FK520 PKS encompassing the KS and AT domains of module 4 as well as the KS-AT interdomain region (10–855); the ATL-ACPL interdomain region of OleAI, followed by the ACPL domain and the rest of the OLE PKS (856–end). The amino acid sequence of the hybrid portion of this PKS is shown in FIGS. 11A–B.

The hybrid PKS above is then changed in the DNA sequence corresponding to aa 177 so that the C is replaced by a Q residue in the final hybrid PKS, yielding the amino acid sequence of FIGS. 12A–B.

These hybrid PKS loading domains can be employed in the methods of the invention as described and illustrated in Example 3.

EXAMPLE 3

Production of 15-Methyl-Erythromycins in *Saccharopolyspora erythraea* and *Streptomyces fradiae*

This Example describes methods and recombinant host cells of the invention for efficient and economical production of 15-methylerythromycin A and/or 15-methylerythromycin C, both of which can be converted to ketolides with potent anti-bacterial activity. The recombinant host cells of the invention directly produce high levels of 15-methylerythromycin A or 15-methylerythromycin C without diketide feeding. Products from these strains can be used in the production of potent ketolide antibiotics. More specifically, this Example describes methods to:

(1) introduce a series of genes to construct a pathway or series of pathways in *Sac. erythraea* or an eryM derivative to produce butyryl-CoA or ethylmalonyl-CoA at levels sufficient to permit high level synthesis of 15-methylerythromycins, and concomitantly, determine whether the level of propionyl-CoA can be reduced in a directed fashion without affecting the pools of other required precursors, so that DEBS can make 15-methylerythromycins exclusively;

(2) re-engineer the loading domain of DEBS to initiate the synthesis of 15-methylerythromycin A with butyryl-CoA or ethylmalonyl-CoA in a high-producing strain of *Sac. erythraea*; and (3) introduce a series of genes into a high-producing strain of *Streptomyces fradiae* to enable production of 15-methylerythromycin C, including genes enabling the host to produce TDP-desosamine, transfer desosamine and mycarose to the erythromycin backbone, and hydroxylate 15-methylerythromycin at the appropriate positions.

References cited in this example by reference number in parentheses, and the numbered listing of references is located at the end of the example. Compound numbers are bracketed.

The benefits provided by the present invention can be better appreciated with some understanding of the need for improved antibiotic compounds. Erythromycin A [1] and its semisynthetic derivatives clarithromycin [2] and azithromycin [3] are widely used antibiotics in human healthcare because of their broad spectrum of activity and their minimal side-effects. They are used primarily against respiratory tract pathogens (*Streptococcus pneumoniae, St. pyogenes, Hemophilus influenzae*), some Gram-positive pathogens of skin and soft-tissue (*Staphylococcus aureus*) and, to a lesser extent, the opportunistic pathogens belonging to the Enterococcus species. Clarithromycin is used in combination with a proton-pump inhibitor in the treatment of the gastic ulcer-associated bacterium *Helicobacter pylori*. World-wide sales of macrolides exceed U.S. $3 B annually.

Continued use of these macrolide antibiotics is threatened by the rise of resistance to these agents, often accompanied by the presence of other genetic determinants conferring resistance to many antibiotics. Of importance is MRSA (methicillin-resistant *Staph. aureus*), most strains of which also carry macrolide resistance. Only vancomycin is currently available for treatment of these agents. Macrolide-resistant *Strep. pneumoniae* is emerging in the U.S., Europe, and Japan, particularly strains which have also acquired penicillin resistance. There is a growing need, therefore, to discover and develop novel antibiotics that can overcome current resistance mechanisms. One approach is to discover agents that attack essential bacterial targets not hit by existing drugs, and thus not expected to exhibit pre-existing resistance patterns. This approach is generally based upon screening either large combinatorial chemical or natural product libraries. Another approach is to modify existing agents, such as macrolides, so as to overcome the resistance mechanisms. The ketolides fulfill this second objective.

Macrolides block protein synthesis by binding to the 50S ribosomal subunit and causing premature release of peptidyl tRNA (1). The segment of nucleotides surrounding the A-2058 (*Bacillus subtilis* numbering) residue in domain V of the RNA molecule interacts with erythromycin and other macrolides (2) and is the target of ERM methylases which confer resistance through methylation of A-2058 and subsequent blocking of macrolide binding. This resistance is also referred to as MLS (macrolide-lincosamine-streptogramin B) resistance (3). Both inducible and constitutive MLS resistance is found in pathogenic bacteria. In inducible strains, methylase activity develops in the presence of the antibiotic. In constitutive strains, the activity is present even in the absence of the drug, although drug often increases the level of resistance. Macrolides such as tylosin [4] and spiramycin [5] do not appear to induce MLS resistance in inducible strains, but constitutively MLS-resistant strains are resistant to tylosin and other 16-membered macrolides.

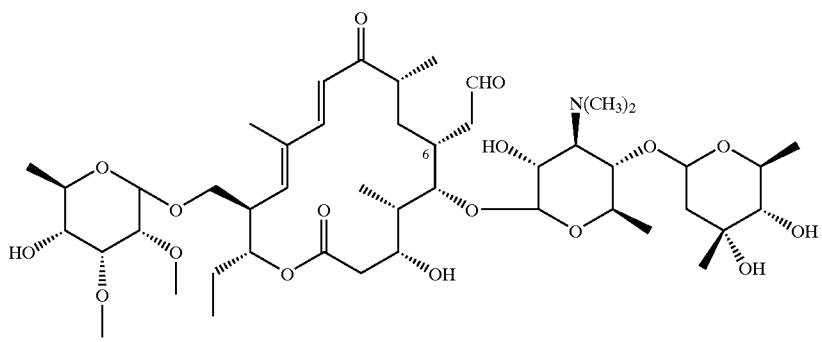

4

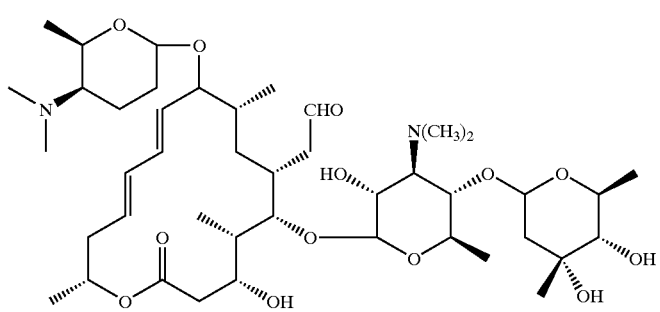

5

A second mechanism of resistance in Gram positive pathogens, efflux, uses export of the compound from the host to keep intracellular concentrations of the drug low and can be either inducible or constitutive. Several genes (mef) in Streptococcus sp. have been found to confer efflux-based resistance (4). The 16-membered macrolides appear to bypass the efflux mechanism and can be used against some of these strains.

A novel series of semisynthetic macrolides called ketolides introduced by Hoechst-Marion-Roussel (HMR 3647 [6]) and Abbott (ABT-773 [7]) show excellent activity against Gram-positive pathogens, including those carrying inducible MLS resistance and many S. pneumoniae and S. pyogenes strains carrying constitutive MLS resistance (5,6). These compounds are also active against S. pneumoniae strains carrying efflux resistance. It is believed that the N11-aralkyl side chains of these molecules attach themselves to the ribosome at a site distinct from domain V and thus enable binding to methylated ribosomes. Compounds 6 and 7 are currently in clinical development.

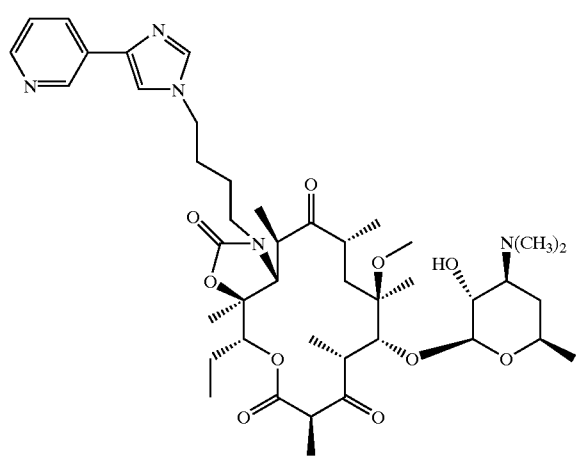

6

-continued

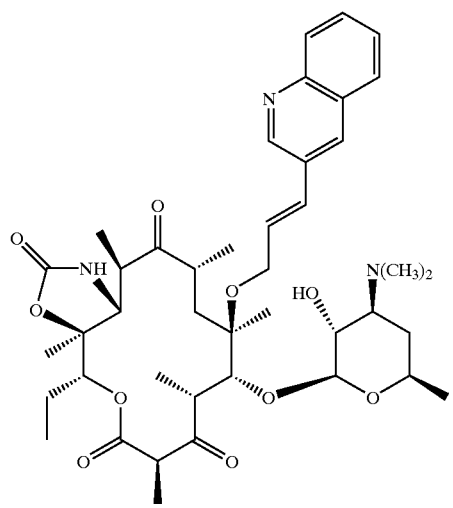

7

The biosynthesis of macrolide antibiotics is best understood for erythromycin (in *Saccharopolyspora erythraea*) and tylosin (in *Streptomyces fradiae*). For erythromycin (see the figure below), the polyketide 6-deoxyerythronolide B [6-dEB; 8], is produced by the successive condensation of one propionyl-CoA (p-CoA) and six methylmalonyl-CoA (mm-CoA) molecules. The polyketide synthase (PKS) that assembles 6-dEB, 6-deoxyerythronolide B synthase (DEBS), is determined by the genes eryAI, eryAII and eryAIII. Polyketide synthesis is followed by 6-hydroxylation (eryF) to yield erythronolide B [9]. Addition of the sugar L-mycarose (via TDP-mycarose) to yield 3-O-alpha-mycarosyl-erythronolide B [10] and the addition of desosamine (via TDP-desosamine) yields erythromycin D [11]. The two sugars are produced by independent pathways not shown here but controlled by the genes designated eryB (mycarose) and eryC (desosamine). The final steps are hydroxylation of 11 to yield erythromycin C [12] by a second P450 enzyme (eryK) and O-methylation of the mycarosyl residue (eryG) to yield the cladinosyl moiety in erythromycin A [1]. A side product is erythromycin B [13], which results from the methylation of 11 and is only poorly converted to 1.

Figure 5:
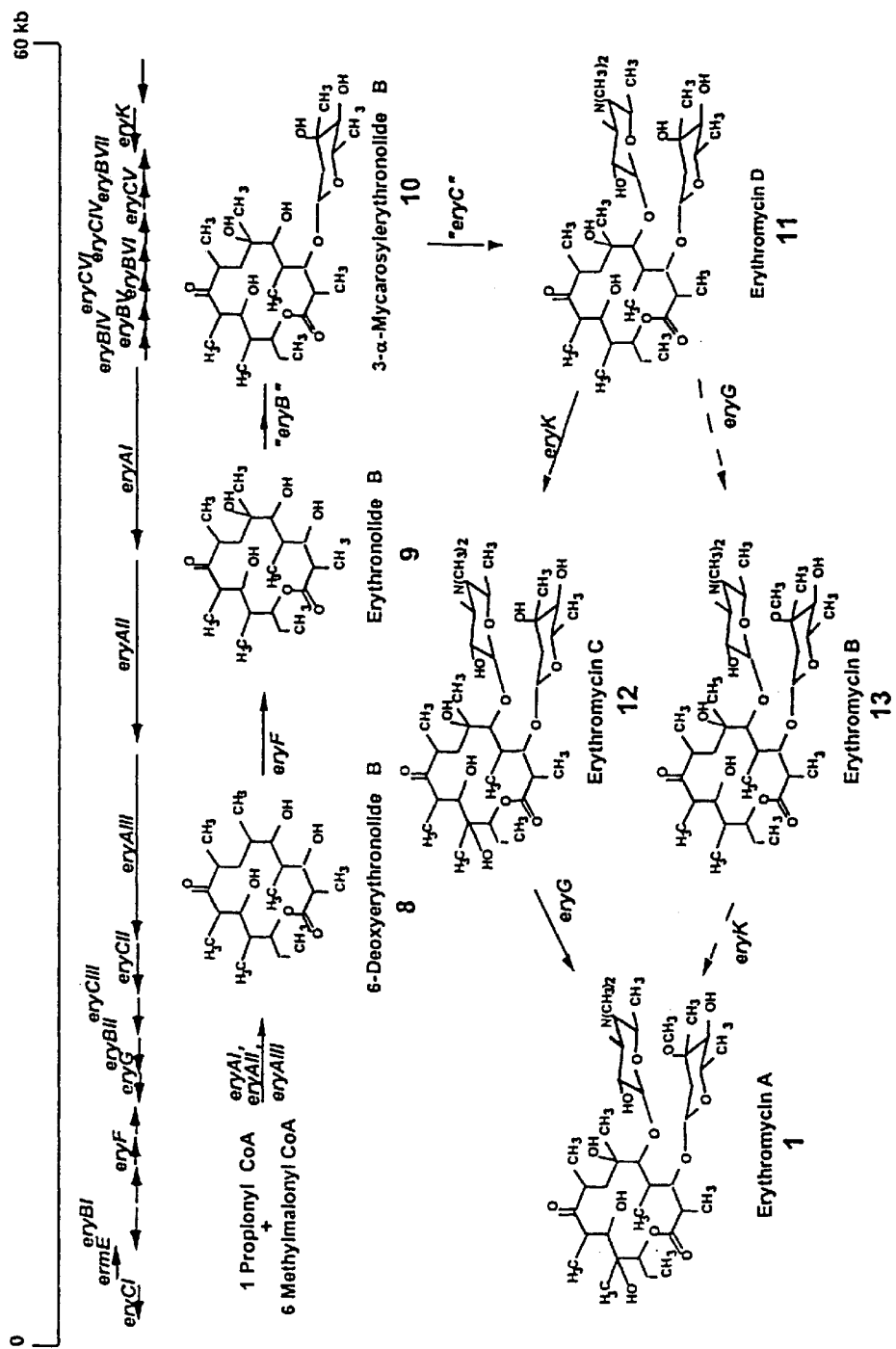
FIG. 5 shows the pathway and genes for erythromycin biosynthesis in *Saccharopolyspora erythraea*.

FIG. 5 shows the pathway and genes for erythromycin biosynthesis in *Sac. erythraea*.

Tylosin [4] is produced in a similar fashion: formation of the polyketide, oxidation of the C-6b methyl to the aldehyde, addition of the three sugars in succession, and finally, methylation of the sugar. In addition to the single additional condensation required to construct the 16-membered macrolactone ring, named protylonolide or tylactone, the ring itself is built from condensations that employ the precursors in the following order of use: p-CoA (or mm-CoA; see below), mm-CoA, mm-CoA, malonyl-CoA (m-CoA), mm-CoA, ethylmalonyl-CoA (em-CoA), mm-CoA, m-CoA.

Production of erythromycin depends upon the cells having a supply of the precursors p-CoA and mm-CoA. Tylosin requires mm-CoA, m-CoA and em-CoA, which is built from butyryl-CoA (b-CoA). Although the wild type cultures of *Sac. erythraea* and *S. fradiae* produce 10–100 mg/L of erythromycin and tylosin, respectively, in fermentation broths, strains of the two cultures exist that can produce the compounds at higher levels. The biochemical basis for high level production is not understood, but it is clear that the supply of precursors does not limit the production of the drugs at high levels in such hosts. Some work has been done on precursor supply in macrolide producing organisms, but work on high producing strains has not been reported. Schemes for the synthesis of the components used for erythromycin synthesis, p-CoA and mm-CoA and also required for tylosin synthesis, as well as m-CoA and em-CoA, required for the latter are shown in FIG. 2 and below.

The degradation of valine through the route shown below has been demonstrated in *Streptomyces avermitilis*, the producer of avermectin, a complex polyketide that utilizes ib-CoA as the starter, and employs mm-CoA in building the polyketide ring (7). Valine utilization can produce the n-butyrate-derived units in tylosin (8). In addition, the rate of valine degradation has been shown to have major impact on tylosin and spiramycin production (9–12). Addition of valine increases tylosin production and has been shown to increase the level of ib-CoA (ib-CoA), most likely resulting in increases in the em-CoA, p-CoA, and mm-CoA required for tylosin synthesis. Conversion of ib-CoA to mm-CoA takes place through methacrylyl-CoA (13) and is probably a major source of mm-CoA from valine-fed fermentations (14,15). High utilization of valine would require high flux through the pathway to mm-CoA, not yet reported for high producing strains. It has been shown that increasing the copy number of valine dehydrogenase in a low tylosin-producing strain results in the increase in the titer of tylosin produced (11,12). For *Sac. erythraea*, addition of proteinaceous material to the fermentation also increases the titers of erythromycin produced (16). It is possible that high levels of mm-CoA required for the synthesis of erythromycin can be achieved from the carboxylation of p-CoA by the enzyme propionyl CoA carboxylase, although the disruption of p-CoA carboxylase activity in a low erythromycin-producing *Sac. erythraea* strain did not affect the antibiotic titer (17). On the other hand, the finding that the disruption of the gene eryM, which encodes a methylmalonyl CoA decarboxylase, results in the cell running out of the supply of p-CoA and arresting erythromycin synthesis in a low-producing strain of *Sac. erythraea* (18) suggests that p-CoA is derived from mm-CoA and not that mm-CoA is derived from p-CoA. It can be seen from the biosynthetic pathway shown below that p-CoA can be produced from alternate sources such as the degradation of leucine and the breakdown of odd-chain fatty acids, and it has been shown that addition of oils can improve the titers of erythromycin (19).

Figure 6:
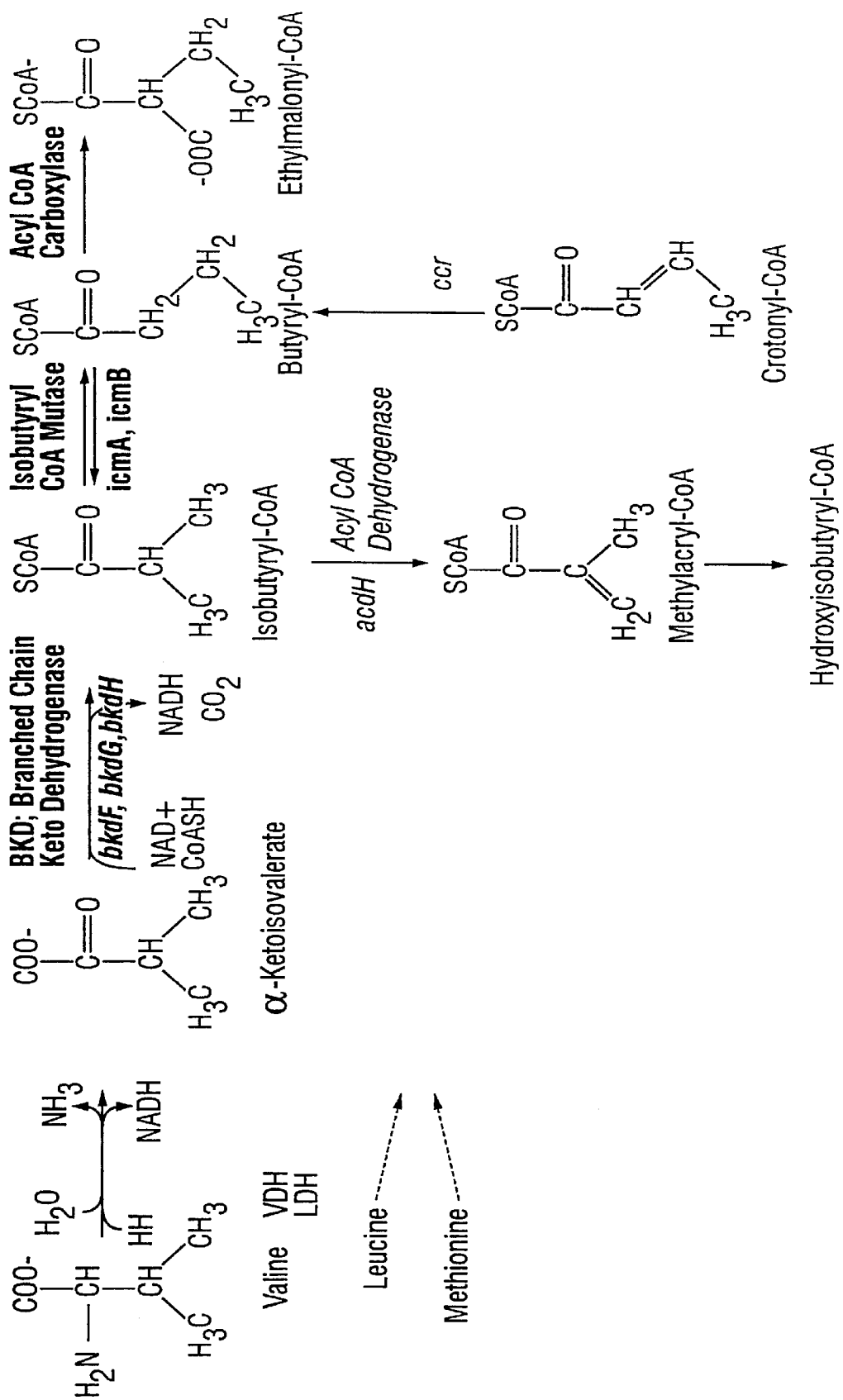
FIGS. 6A–6C show pathways for the synthesis of acyl-CoA precursors in Streptomyces.
Figure 6:
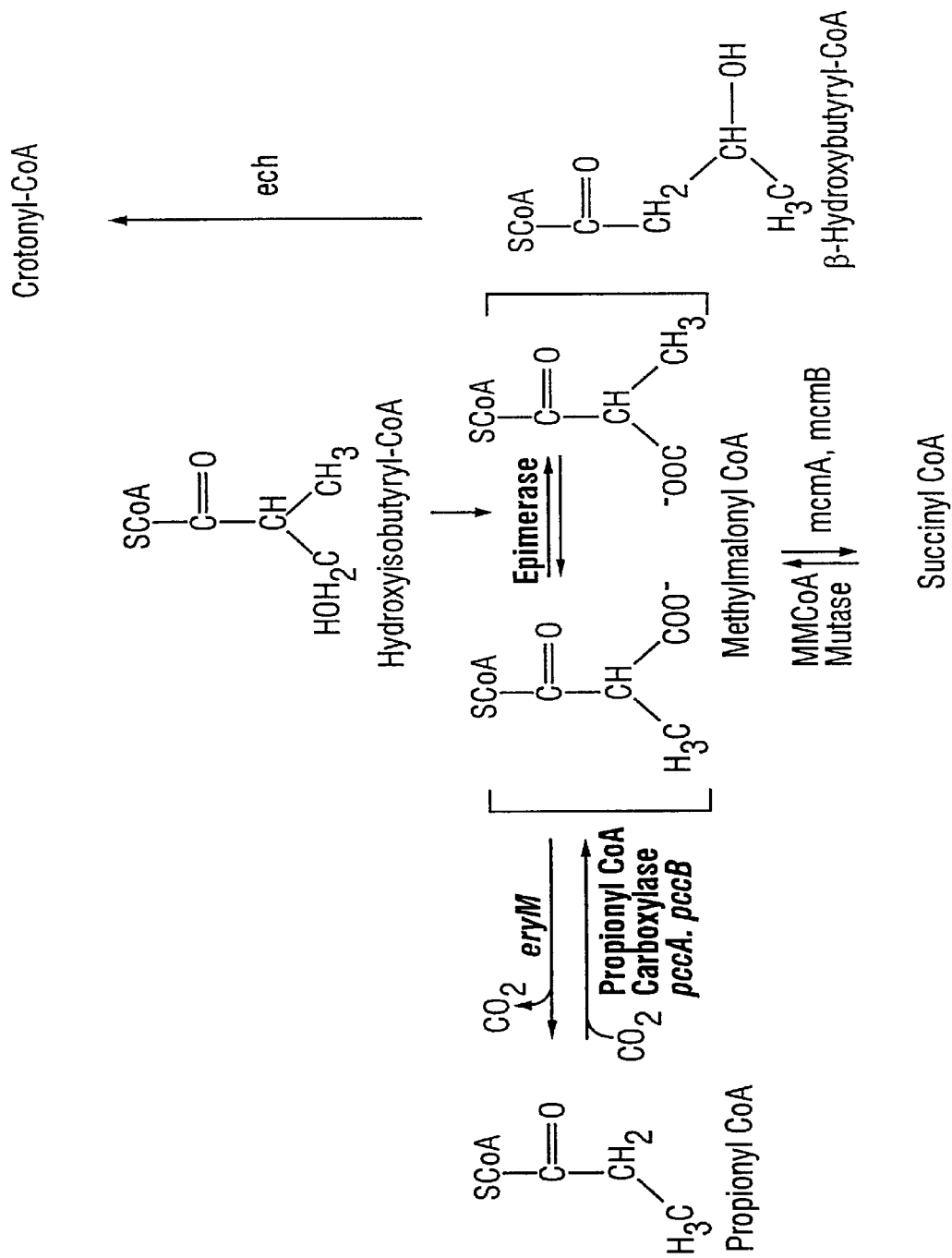
Figure 6:
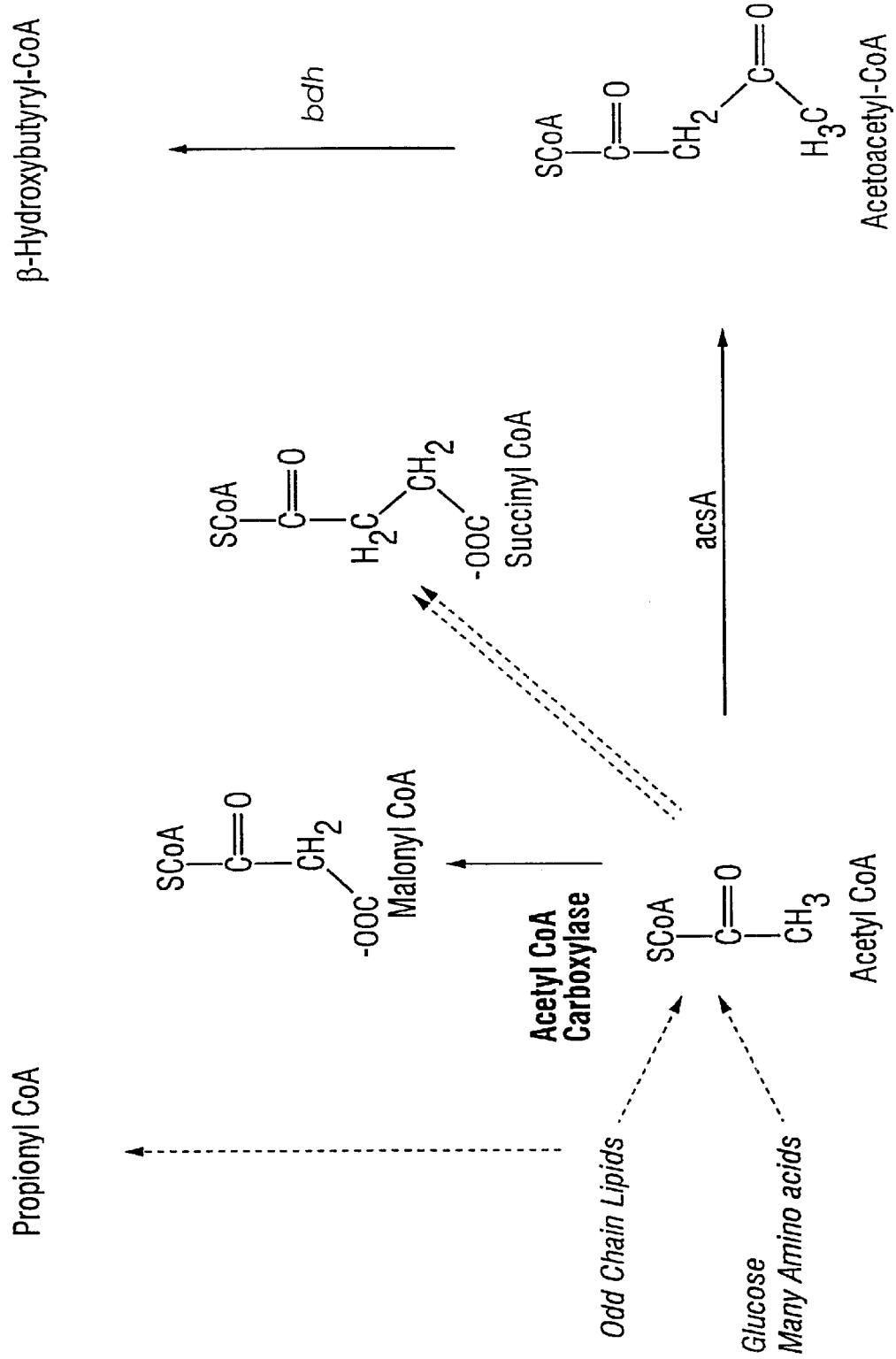

Several other routes to mm-CoA are shown below. One is the conversion of succinyl-CoA to mm-CoA via the enzyme methylmalonyl CoA mutase, which has been identified in *S. cinnamonensis*, producer of the polyketide monensin (20). Succinyl-CoA arises from the oxidation of acetyl-CoA via the Krebs cycle, but requires the input of oxaloacetate, which would be derived from the breakdown of glucose. Because the utilization of glucose is generally controlled in high-titer fermentations, and because it serves as the principal source for the synthesis of the deoxysugars present in macrolide antibiotics, it is unlikely that it serves as a significant source of precursors. Succinyl-CoA could also come from alphaketoglutarate, produced from deamination of glutamate. Fermentations fed with succinate or its purported precursors have only shown marginal increases in titers of polyketides, indicating that the succinyl-CoA pathway is not a major contributor to the large precursor pools required for high level synthesis, but this has not been ruled out in the high titer strains. FIGS. 6A–C shows pathways for the synthesis of acyl-CoA precursors in Streptomyces. Enzymes are shown in bold: VDH, valine dehydrogenase; LDH, leucine dehydrogenase; MMCoA mutase, methylmalonyl CoA mutase.

A rather circuitous route to mm-CoA shown in the figure above is the conversion of acetyl-CoA to b-CoA, conversion to ib-CoA, and then degradation to mm-CoA. This pathway in its entirety has been shown to exist in *S. cinnamonensis* (20), and the enzyme that converts ib-CoA to methyacrylyl-CoA has been found in *S. coelicolor* and *S. avermitilis* (13). This pathway is believed to exist in *S. fradiae*. It allows acetyl-CoA, the most abundant precursor in the cell, to be converted into mm-CoA. The pathway depends on the enzyme crotonyl-CoA reductase (ccr), which reduces crotonyl-CoA to b-CoA. CCR activity has not been demonstrated in wild type *Sac. erythraea*, nor does this organism contain a DNA sequence hybridizing with the *Streptomyces collinus* ccr gene (21,22). *Sac. erythraea* thus probably cannot make mm-CoA from acetyl-CoA, and probably relies on the degradation of valine, oils and other amino acids to produce mm-CoA in sufficient quantities to sustain high level synthesis of erythromycin. *S. fradiae* has a ccr gene and is believed to contain a complete pathway to make mm-CoA from acetyl-CoA (23). Thus, the mm-CoA precursor, at least for tylosin, can be made via several sources.

Little is known about the supply of butyrate-derived precursors in *S. fradiae*, although some work has been done in *S. collinus* and *S. cinnamonensis*, both of which make b-CoA. The pathway from acetyl-CoA to b-CoA shown above is best understood in *Clostridum acetobutylicum*, which produces high levels of butanol. Genes for the pathway have been cloned from various sources, but at least one counterpart of each gene has been shown to be present in the genome of *Streptomyces coelicolor* A3(2) (Sanger Web site). Genes for the entire pathway from acetyl-CoA to b-CoA are thus accessible. The *S. collinus* ccr gene supports incorporation of low levels of em-CoA into 6-ethylerythromycin in a strain of *Sac. erythraea* expressing a mutant DEBS (22), demonstrating that *Sac. erythraea* has the capability of utilizing b-CoA as a precursor for polyketide synthesis.

Wallace et al. (24) demonstrated that labeled valine was incorporated into butyrate in *Sac. erythraea*, suggesting the pathway valine→ib-CoA→b-CoA. Yet b-CoA, which can be employed as a starter by DEBS, has not previously been demonstrated to be incorporated into erythromycin in high titer fermentations. The findings of Wallace et al. suggest the presence of an ib-CoA mutase in *Sac. erythraea*, but this activity has not been examined. The genes for ib-CoA mutase, icmA and icmB, have been cloned from *S. cinnamonensis* (25,26). Thus, in accordance with the methods of the invention, pathways to produce b-CoA in high levels in *Sac. erythraea* are available and transferable from related polyketide producers. Only a minimum number of additional steps are needed to convert intermediates into b-CoA in *Sac. erythraea*.

DEBS has been extensively studied genetically and biochemically, and the details will thus not be reviewed here. FIG. 1 shows the linear modular organization of the enzyme complex, displaying the functional domains within the modules and the structure of the growing acyl chain at the end of each cycle of growth and reduction. DEBS consists of 6 extender modules and a loading module. Precursor specificity is provided by the AT domains (27). The DEBS loading module shows relaxed specificity, loading various acyl-CoAs depending upon the environment (28–30). Tylosin is produced similarly by a 7-module PKS. The loading module of the tylosin PKS, fully sequenced (31) contains a $KS^Q$ domain that has decarboxylase activity (32,33) and an AT domain having the signature sequence for mm-CoA binding. It is likely, therefore, that the tylPKS employs mm-CoA, malonyl-CoA and em-CoA to make tylosin.

PKS genes for other complex polyketides such as rapamycin (34), pikromycin (35), avermectin (36), FK506 (37) and rifamycin (38) all show similar organizations as the erythromycin and tylosin PKSs. AT, KR, DH and ER domains may be exchanged between different PKSs, even in combinations to result in the creation of polyketides with novel but predicted structures (39–42). The loading domain of one PKS can be exchanged for a loading domain of another to produce a hybrid polyketide (43,44). In accordance with the methods of the present invention, a loading domain is exchanged for an extender domain, and then converted back to a loading domain.

Figure 7:
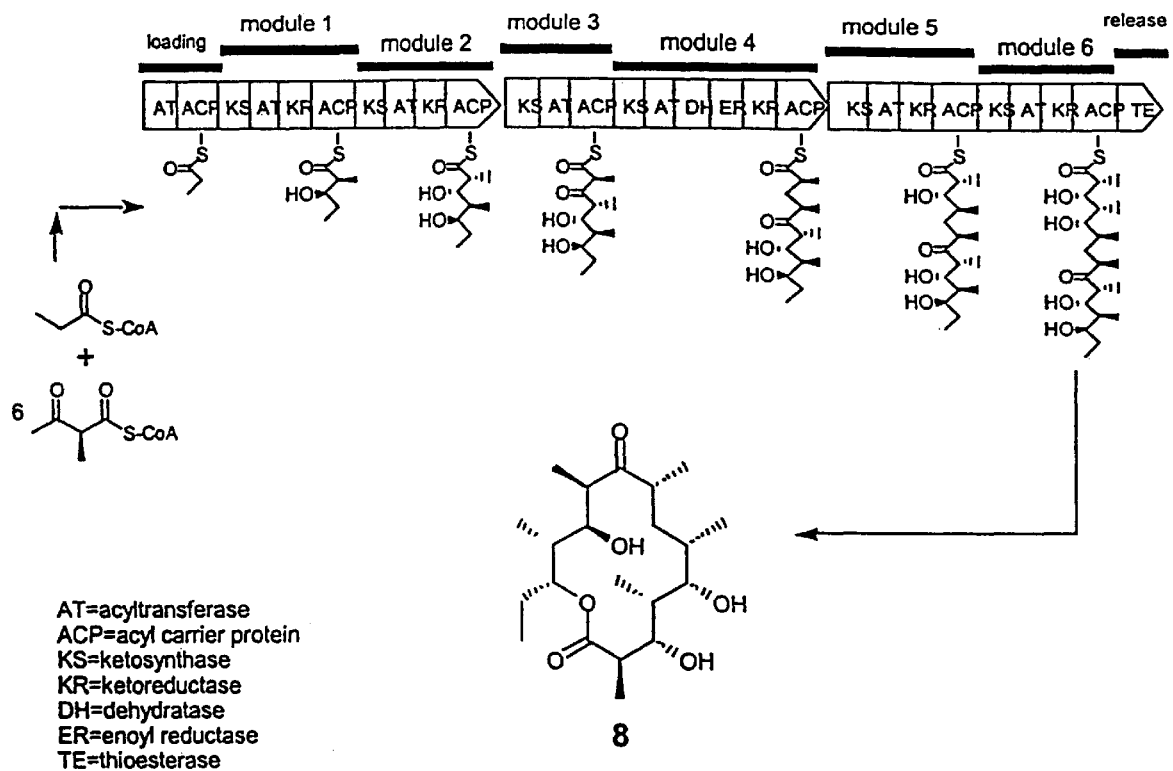
FIG. 7 shows the erythromycin PKS and synthesis of 6-deoxyerythronolide B.

Heterologous expression of DEBS in *S. coelicolor* (45) yielded a mixture of 6-dEB and 8,8a-deoxyoleandolide, at levels up to 50 mg/L. DEBS can thus initiate polyketide synthesis in vivo either from p-CoA or acetyl-CoA. Similarly, the DEBS1 protein (containing the loading module and modules 1 and 2) was re-engineered by placing the TE domain after the ACP domain of module 2. In *S. coelicolor*, the DEBS1-TE construct yielded the predicted triketide products 2,4-dimethyl-3,5-dihydroxyheptanoic acid delta-lactone [14] and 2,4,-dimethyl-3,5-dihydroxyhexanoic acid-delta-lactone [15] shown below (46). It is thus not always necessary to replace the DEBS loading domain to alter the starter unit. FIG. 1 and FIG. 7 show the erythromycin PKS and synthesis of 6-deoxyerythronolide B.

Inactivation of the module 1 KS domain of DEBS has been used to bypass the loading domain specificity. This KS1 null (KS1°) mutation produces novel polyketides when supplied with analogs of the normal product of module 1, a diketide thioester (47,48). This technology has been used to convert (2S,3R)-2-methyl-3-hydroxyhexanoate N-acetylcysteamine (SNAC) thioester into 15-methyl-6-dEB (6-deoxy-15-methylerythronolide B) [16]. This compound is converted to the antibiotic 15-methylerythromycin A when fed to a KS1° strain of *Sac. erythraea*.

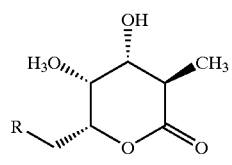

14, R = CH₃

21, R = CH₂CH₃

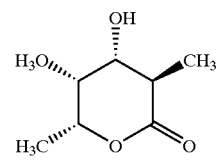

15

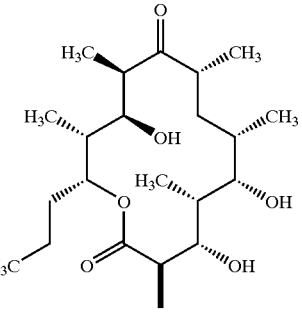

16

The desosamine of erythromycin and the mycaminose of tylosin differ only by a C4-hydroxyl, and are made by similar routes, shown schematically below. Biosynthesis of TDP-mycaminose requires only two steps past common intermediate 1', C-3 amination and N-dimethylation, whereas TDP-desosamine synthesis requires dehydration and reduction at C-4, then C-3 amination and N-dimethylation. The genes for TDP-desosamine biosynthesis (eryC) in *Sac. erythraea* cluster with the other ery biosynthesis genes. It is believed that the dehydration and reduction functions are encoded by the genes eryCIV and eryCV (49–51). The genes for TDP-mycaminose synthesis have also been described (51a,b). Both *Sac. erythraea* and *S. fradiae* make TDP-mycarose; thus, the gene distinguishing the pathways in the two hosts is the one encoding the mycarosyltransferase. In *Sac. erythraea* it is designated eryBV. There is no expectation that the *S. fradiae* mycarosyltransferase can use erythronolide B as a substrate should one desire to make an erythromycin analog in this host.

Figure 8:
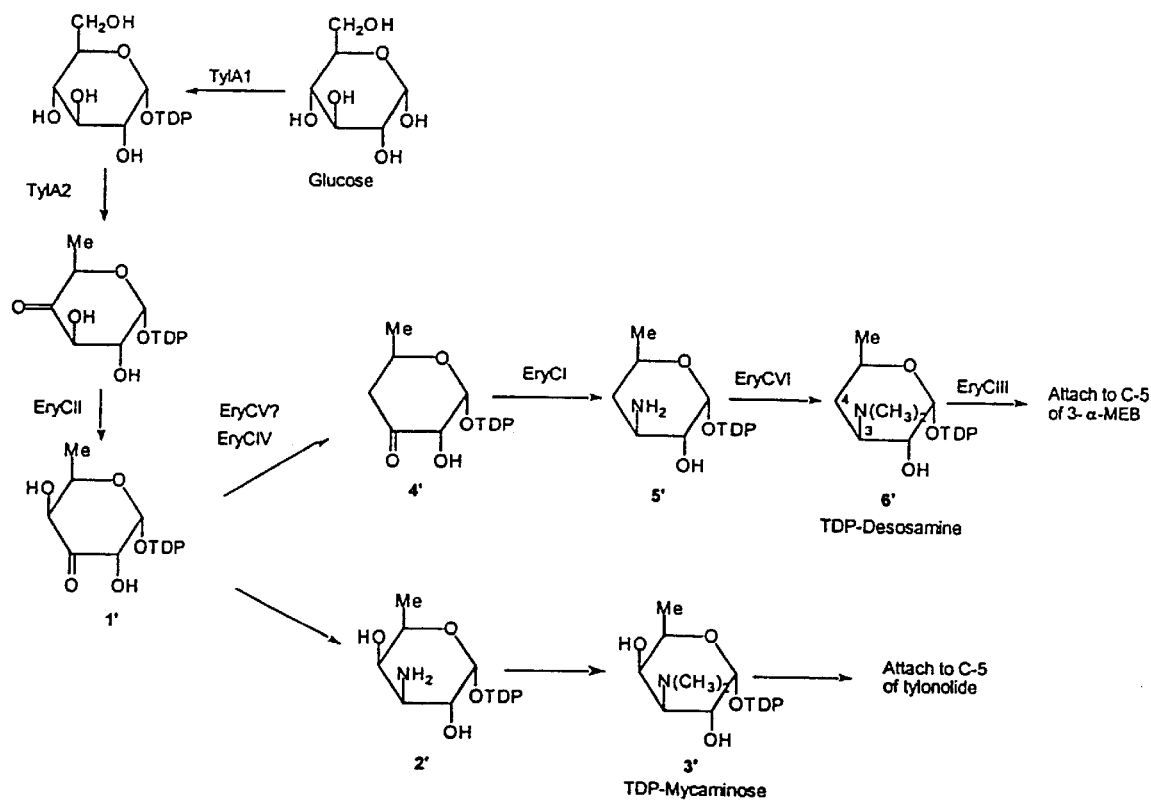
FIG. 8 shows the pathways to TDP-desosamine and TDP-mycaminose.

FIG. 8 shows the pathways to TDP-desosamine and TDP-mycaminose.

Novel ketolide compounds with improved antibacterial activity over the currently marketed macrolides clarithromycin and azithromycin have been produced. A number of diketide-SNAC thioesters were synthesized and fed to *S. coelicolor* CH999/pJRJ2 (deleted for the actinorhodin PKS and carrying the [KS1°]-DEBS genes). The resulting macrolactones were purified and fed to *Sac. erythraea* (KS1' strain K39-14) to convert the macrolactone to the erythromycin A analog. After preliminary antibacterial testing, 15-methylerythromycin A [17] was of great interest. Samples of 17 were chemically converted into the 3-descladinosyl-3-oxo-6-O-methyl-10,11-anhydro derivative [18] and then to a number of ketolide derivatives, of general structure 19 with compound 20 as an example.

Compounds related to 20 have been subjected to extensive in vitro testing and in vivo testing.

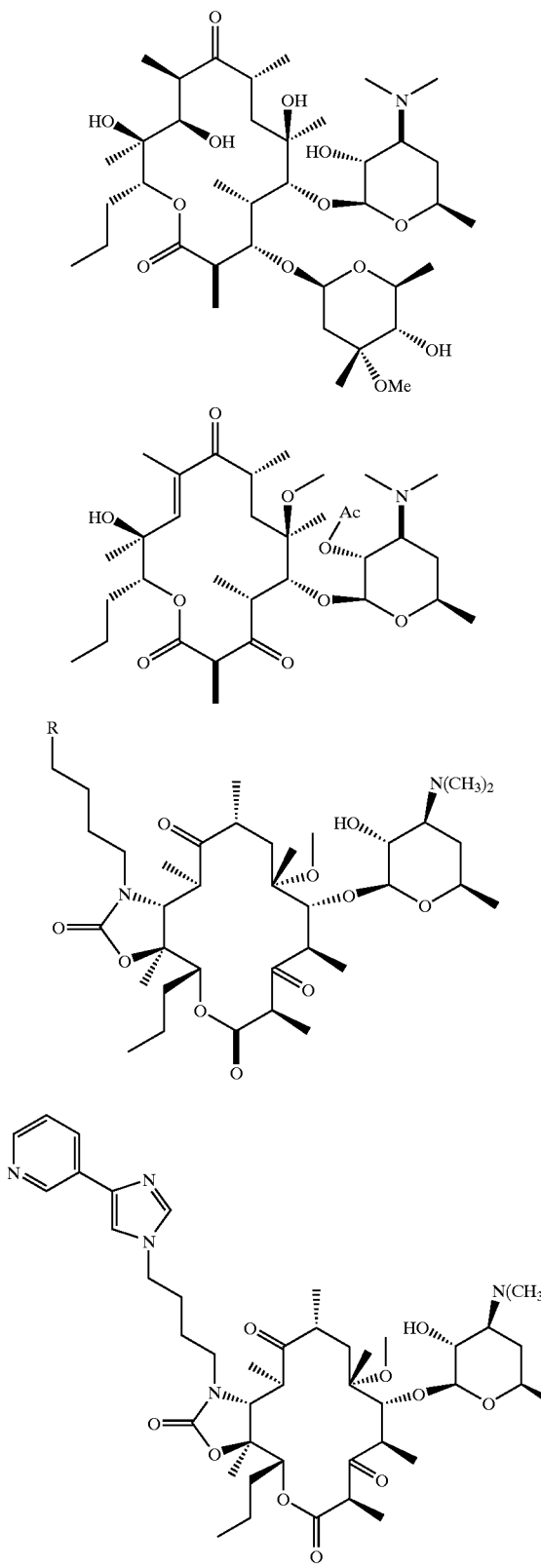

Figure 9:
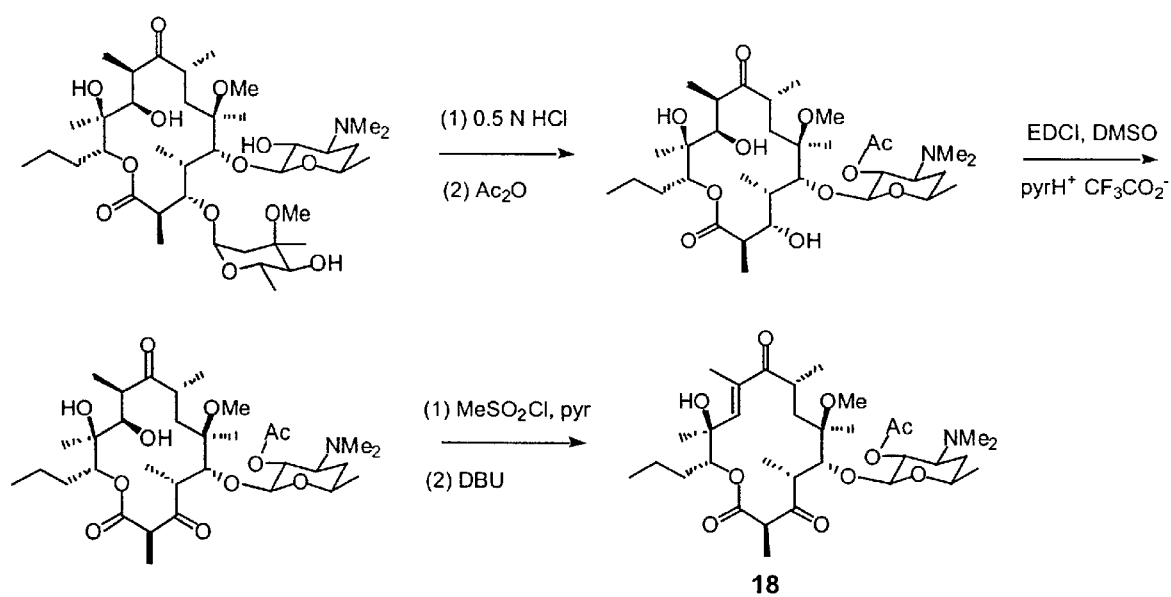
FIG. 9 shows production of a 10,11-alkene from 15-methylerythromycin A.

The initial transformation of 15-methylerythromycin A into the 6-O-methyl derivative follows standard procedures (52) and proceeds in good overall yield. The key intermediate in the synthetic process is the 10,11-alkene [18], which is produced similarly to reported ketolides (53). The 6-O-methyl analog is subjected to acid-mediated removal of the cladinose, and the resulting 3-hydroxy group is oxidized to the ketone after protection of the desosamine 2'-hydroxyl as the acetate. The 11-hydroxyl group is converted to the mesylate, then eliminated by treatment with diazabicycloundecene (DBU) to introduce a 10,11-alkene functionality. This procedure results in an overall 10–15% yield of 18 starting from the initial 15-methylerythromycin A (see FIG. 9).

Thus, it would be advantageous to produce 15-methylerythromycin A [15-MeEryA] or 15-methylerythromycin C [15-MeEryC] in a recombinant strain of Sac. erythraea or S. fradiae. This example describes three approaches, two using the erythromycin producer Sac. erythraea and one using the tylosin producer S. fradiae. In Sac. erythraea, the approaches employ replacing p-CoA as the starter for 15-MeEryA synthesis with either b-CoA or em-CoA. Both involve building a supply of b-CoA in the host at sufficient levels so that it does not limit the synthesis of the antibiotic. In S. fradiae, which is not limited for b-CoA because it makes high levels of tylosin, genes concerned with the production of the erythromycin polyketide and its C6 and C12 hydroxylation and glycosylation with desosamine are introduced.

The first method using Sac. erythraea aims to reduce the level of p-CoA so that it does not compete with b-CoA for loading of DEBS. As described in Example 1, disruption of the eryM gene, which encodes a decarboxylase that converts mm-CoA to p-CoA (18), did not result in a notable decrease in erythromycin production by the strain of Sac. erythraea grown in a rich production medium that supports high level antibiotic production. A minimal medium and washed cells were used in the work that reported the lack of erythromycin production by an eryM mutant (18). A considerable decrease was anticipated if the supply of p-CoA made from mm-CoA had been reduced markedly and caused a corresponding decrease in the rate of initiation of 6dEB biosynthesis. The effect of the eryM mutation on the p-CoA level has not been examined. One can reduce the level of p-CoA through fermentation conditions (e.g., supplementation with butyric acid or butanol) and by overexpression of p-CoA carboxylase, the enzyme that converts p-CoA to mm-CoA.

In the second method, the normal ATL domain of the loading module of DEBS in Sac. erythraea is mutated to a form that preferentially uses b-CoA over p-CoA or is replaced with an extender $AT_E$ domain that is specific for em-CoA. In the latter case, a $KS^Q$ domain is introduced immediately preceding the $AT_E$ domain to decarboxylate the PKS-bound em-CoA and thus provide b-CoA on the PKS to initiate 15-MeEryA synthesis. Alternatively, the entire loading module of DEBS1 is replaced with one that specifies formation or utilization of a saturated C4 alkyl starter unit, such as can be obtained from the rimocidin PKS genes that can be cloned from the oxytetracycline producing Streptomyces rimosus strain (53a).

These methods may require or benefit from the introduction of a pathway to produce b-CoA or em-CoA derived from it in Sac. erythraea in levels sufficient to support high level production of 15-MeEryA. The invention provides several different methods to this end. First, intermediates from the breakdown of valine can be directed into the b-CoA pathway by introducing and overexpressing genes encoding the ib-CoA mutase. If the breakdown of valine is limiting, one can enhance the pathway by introducing and overexpressing the genes for branched chain alpha-keto acid dehydrogenase (bkd). If this approach fails to provide the required levels of b-CoA or in the alternative, one can introduce and overexpress up to the four genes that encode enzymes required to convert the abundant acetyl-CoA to b-CoA.

In an alternative method of the invention, the desired compound can be produced in the tylosin producer *S. fradiae*. Because the synthesis of tylosin employs em-CoA, synthesis of 15-MeEryA in this strain should not be limited by the supply of the b-CoA precursor. However, the pathway to the erythromycins must be assembled in *S. fradiae* using a modified DEBS that employs b-CoA or em-CoA as the starter. This can be achieved by the method of Hu et al. (53b) that enables the directed transfer of large DNA segments between streptomycetes. In one embodiment, the entire erythromycin gene cluster is transferred into an *S. fradiae* strain so as to replace the tylosin PKS genes. As described below, the recombinant DEBS genes employed contain a coding sequence for a hybrid loading module, six extender modules, and a thioesterase. The coding sequences for the six extender modules and thioesterase can originate from, for example, the ery genes (involved in the synthesis of erythromycin), the ole genes (involved in the synthesis of oleandomycin), or the meg genes (involved in the synthesis of megalomicin).

Because the strain can be used in the production of 15-MeEryA, one may wish to avoid employing methods that introduce genes on autonomous plasmids that require the addition of a drug to select for their maintenance in the culture. Such addition of drugs could add significant costs to the production process. In addition, because the cultures could ultimately be used in large scale manufacturing processes, one may again wish to avoid adding drug resistance genes to the producing cultures (*Sac. erythraea* or *S. fradiae*) even if one does not intend to employ the drugs. Therefore, the invention enable one to employ plasmids to deliver genes that integrate in the chromosome through site-specific integration or double-site homologous recombination. For the integration, one can choose sites in the genome that are neutral with respect to erythromycin biosynthesis. One such site is the native attB site used by vectors that contain the phiC31 attP gene and another is an approx. 5 kb region adjacent to the eryK gene in *Sac. erythraea*, that when disrupted has been shown to have no effect on erythromycin synthesis (54). In *S. fradiae* as well, a number of neutral sites in the chromosome are available for homologous recombination (55).

In constructing the strains of the invention, one may desire to determine accurately the levels of acyl-CoAs in cells grown under various conditions. The methods of Hosokawa et al. (56) and Kikuchi et al. (57) can be used for extraction of the CoA esters from cells and HPLC analysis employing authentic standards. Because there are no published reports of acyl-CoA determinations in actinomycetes, one must be concerned primarily with a potentially high background that can obscure accurate measurement. Hosokawa et al. (56) found that passage of liver tissue extracts over a Sep-Pak $C_{18}$ cartridge greatly reduced background and allowed accurate determinations. This approach can be followed, with other columns that can partially purify and concentrate CoA esters also employed. The identities of the CoA esters can be confirmed by LC/MS analysis. Inclusion of an internal standard such as benzoyl-CoA will allow for quantitation of the acyl-CoA levels. One may wish to correlate p-CoA and mm-CoA levels in an erythromycin producing strain with erythromycin production under fermentative conditions. In *S. fradiae*, one can repeat this for p-CoA, mm-CoA, and b-CoA. To set a baseline for precursor effects, one can compare different strains of *Sac. erythraea* that produce different amounts of erythromycin for acyl CoA levels. In addition one can compare levels when a given strain is grown under different conditions.

As shown in Example 1, disruption of the eryM gene in a high-producing *Sac. erythraea* strain does not reduce erythromycin synthesis noticeably in rich medium. If one determines that the eryM mutation does not significantly affect the p-CoA level (by comparing the levels of this compound in the eryM$^+$ and eryM mutant backgrounds in cells grown in rich medium), then one can reduce levels of p-CoA further through its increased conversion to mm-CoA. The genes for a p-CoA carboxylase activity (pccA and pccB) of *S. coelicolor* can be employed for this purpose. These genes, under the control of the strong ermE* promoter, can be inserted into a site in the chromosome of the eryM strain, as described above, and the effect on production of erythromycin and various acyl-CoA levels can be examined. The desired result is a diminution of erythromycin synthesis, a drop in p-CoA levels, and an increase or no change in the level of mm-CoA. If this is not observed, one can reduce the intracellular p-CoA levels by altering the fermentation medium, e.g. by removing lipids and amino acids that break down to p-CoA. This approach may also limit the supply of mm-CoA, and if this occurs, one can alter the erythromycin PKS so that it no longer will use p-CoA, as described in Example 2 and below.

A novel method for altering the DEBS loading domain (or any loading domain that has an AT domain that binds propionyl CoA) provided by the present invention involves site specific mutation of the $AT_L$ domain. An Arg residue in an $AT_E$ domain that normally utilizes em-CoA was mutated to an Ala or Trp, and each of the mutated AT domains was substituted for the wild-type $AT_L$ domain of DEBS1. Tests of both mutant proteins by single turnover experiments in vitro revealed that each one prefers b-CoA over p-CoA as substrate. Acetyl-CoA appears to compete for b-CoA, however. This behavior is consistent with the effect of the same mutation on the substrate specificity of the AT domain in animal FAS (57a). A plasmid containing the mutant DEBS1 plus DEBS2 and DEBS3 genes can be constructed in accordance with the methods of the present invention to assess whether either mutation results in preferential formation of 15-methyl-6dEB instead of 6-dEB in vivo under conditions that provide an adequate level of b-CoA and minimize the amounts of acetyl-CoA and p-CoA.

If preferential formation of 15-methyl-6dEB is not observed in a strain of interest, one can employ the following alternative method provided by the present invention. A segment of DNA is assembled through directed or PCR-cloning that encodes $KS^Q$, $AT_E$ (specific for em-CoA) and $ACP_L$ in the DEBS1 (or other) loading module, as illustrated in Example 2. In this case, synthesis is initiated with em-CoA, which is subsequently decarboxylated to yield butyryl-ACP (33) that can be extended by DEBS in the usual way. The DEBS1 gene mutant is combined with the DEBS2 and DEBS3 genes (or analogous genes from, for example the meg or ole gene clusters) to assess the effect on production of 15-methyl-6dEB vs. 6-dEB in vivo.

PKS domain/module switches can result in significant reductions in the amount of polyketide produced (40,42) even though the predicted structure is made. It may be necessary to employ several different $KS^Q$, $AT_E$ and $ACP_L$ domains and employ them in various combinations to construct the PKS capable of producing 15-methyl-6dEB at satisfactory levels. $KS^Q$ domains from the oleandomycin and picromycin/methymicin PKSs have been cloned and characterized at Kosan and can be used to construct the corresponding DEBS1 segment. The $AT_E$ domain from module 4 of the FK520 PKS has also been sequenced, as have those in module 5 of the niddamycin and tylosin gene clusters (31,58). These $AT_E$ sequences can be employed in constructing the novel loading domain coding sequences of the invention. For the ACP in the loading domain one can use the natural DEBS domain or replace it with ones from the cognate modules that are used for the $KS^Q$ or $AT_E$ domains. One should take care to ensure that the native interdomain sequences are maintained as much as is possible and that the spacing distances are kept constant. Because one can test rapidly how efficient each construct is in producing 15-methyl-6dEB, one can let the results guide the domains, interdomain regions, and other factors to achieve the best construct.

Another method of the invention utilizing a novel loading domain involves cloning the portion of the genes from Streptomyces rimosus ATCC 10970 that encodes the loading module and extender module 1 of the rimocidin PKS. Rimocidin is a polyene macrolide produced by this strain along with oxytetracycline, a widely used antibacterial drug. The structure of rimocidin [23] shows a polyketide backbone built from a saturated four carbon starter unit. This could simply be b-CoA or could be formed from acetyl-CoA and m-CoA by the first module of the rimocidin PKS wherein carbon chain assembly involves complete reduction of the initial diketide intermediate. Either case would provide a means for making 15-methylerythromycins. One can clone the desired genes from a cosmid library of S. rimosus DNA using a specific probe for the type I PKS genes involved in rimocidin production. Sequence analysis of approx. 7 kb of DNA from the end of the cluster of PKS genes that contains module 1 of the rimocidin PKS will identify the desired genes and reveal which way the first four carbons of the polyketide backbone are built. If b-CoA is the starter unit, one replace the loading domain of DEBS1 (or the analogous domain of MEG1) with one from the rimocidin PKS, following the guidelines above and then determine whether the plasmid containing the full set of DEBS genes directs preferential production of 15-methyl-6dEB. In contrast, if the first four carbons are built from acetyl-CoA and m-CoA by extender module 1 of the rimocidin PKS, one can replace the loading module of DEBS1 with that module, assuming that the butyryl-ACP formed by it will be accepted by module 1 of DEBS1 to allow elongation of the polyketide chain. Formation of a functional DEBS1 PKS by addition of a complete module to form a trimodular PKS is precedented (58a). This construct can be evaluated as described above for the other PKS genes to assess whether 15-methyl-6dEB is formed preferentially. Success would avoid establishing fermentation conditions favorable to a high b-CoA instead of p-CoA level in vivo.

One can use well established conditions for preparation of recombinant cells, their growth in liquid fermentation media, and the isolation and assay of the desired products in all of the above methods. In particular, to make 15-methyl-6dEB and then 15-methylEryA, the normal DEBS loading module can be exchanged with the engineered loading module/module 1 in a Sac. erythraea strain through homologous recombination employing crossover sites upstream and downstream of the altered sequence in the eryA region. This can be done to result in 15-methyl-6dEB or 15-methylEryA production.

One can build a de novo b-CoA pathway in Sac. erythraea with the aim of producing 15-MeEryA (at high level) in the absence of background EryA. This will take place when the level of p-CoA is low enough and that of b-CoA high enough to allow the optimal form of DEBS employed to use b-CoA (or the em-CoA derived from b-CoA) exclusively as the starter unit. Although the methods described above involving introduction of the p-CoA carboxylase genes or manipulation of the fermentation conditions can allow one to achieve the desired goal, alternative methods are provided by the present invention. Because there is no precedent for employing a genetic approach to diversion of metabolism to produce a novel secondary metabolite, an empirical approach is described here to achieve this goal.

As described above, there are several routes to the synthesis of the various acyl-CoAs required for polyketide biosynthesis (illustrated in FIGS. 6A–C). Because the valine utilization pathway represents a major route to the required precursors, one can shunt some of the pathway intermediate ib-CoA to b-CoA. First, one can check the levels of b-CoA in fermentations fed with high valine content proteinaceous substrates to establish a baseline. Then, one can introduce the S. cinnamonensis genes icmA and icmB for ib CoA mutase into the Sac. erythraea host under the control of the ermE* promoter and examine the cells for the amount of 15-MeEryA and EryA produced. One can also examine cells for the levels of b-CoA and ib-CoA. The degree of success of this method depends on the host either containing a large pool of ib-CoA or there being sufficient flux through the valine degradation pathway to provide enough ib-CoA to be converted efficiently to the required b-CoA to promote its high level incorporation in polyketide synthesis.

If one does not see the desired effect of the icmA and B genes on 15-MeEryA or b-CoA levels in a cell and the cells contain ib-CoA mutase activity, particularly in cultures fed with high valine containing proteins, one can examine pathway flux by measuring the level of BKD activity in erythromycin-producing Sac. erythraea cultures (see FIG. 6A). If one finds indistinguishable levels of activity in low and high erythromycin-producing strains, one can in accordance with the methods of the invention overexpress the S. coelicolor bkdF, G and H genes, which have been identified in the S. coelicolor genome, in the appropriate Sac. erythraea host containing icmA and icmB and determine the effect on 15-MeEryA and b-CoA levels.

A second method provided by the invention is to build the b-CoA pathway from acetyl-CoA or intermediates to b-CoA, such as crotonyl-CoA, produced by fatty acid utilization. As a first step, one can introduce an overexpressed ccr gene from S. collinus or which is cloned from the chromosome of S. coelicolor or S. fradiae into Sac. erythraea. The impact on 15-MeEryA production and b-CoA levels is measured when the host is grown under conditions that permit fatty acid oxidation or with the addition of crotonic acid (or an esterified derivative). One can measure the activity of crotonyl-CoA reductase in the host containing this gene. If the activity of the enzyme is high (relative to published reports) but the level of b-CoA is low, one can clone the remaining three genes acsA, bdh and ech from the chromosome of S. coelicolor and introduce them into the chromosome of Sac. erythraea under control of the ermE* promoter. These genes can be combined, if necessary, with the icmA and icmB (and bkdF, G & H) genes within a given host.

The present invention also provides host cells in addition to Sac. erythraea for production of 15-methylEryA. An illustrative and preferred embodiment is an S. fradiae strain that makes high titers of tylosin. This degree of success with this method depends on an adequate supply of b-CoA. One can employ a model system to establish first the basic requirements for preferential utilization of b-CoA as the starter unit in a strain of interest. This involves formation of 2,4-dimethyl-3,5-dihydroxyheptanoic acid delta-lactone [14] and its 2,4-dimethyl-3,5-dihydroxyoctanoic acid delta-lactone homolog [21] in the strain. Compounds 14 and 21 are made from p-CoA and b-CoA, respectively; therefore, preferential production of 21 will be an indicator of success. Conditions that achieve this should also be the ones that will favor production of 15-methylEryA over EryA.

To achieve a high level of production of 21 in *S. fradiae*, one can clone segments of the DEBS1-TE gene behind the tylG promoter (tylGp) from this strain. An 864 nt sequence immediately upstream of the first tylosin PKS gene has been sequenced. This sequence can be used to isolate the tylG promoter (along with the $KS^Q$ domain) from a genomic library of *S. fradiae* DNA prepared in a cosmid vector in *E. coli*. One can sequence the tylG promoter region and then clone it into the vector used to introduce the constructs into *S. fradiae*. The tylG promoter from the a high level tylosin promoter is preferred, but other systems, such as for example, the actIp-actII-ORF4 expression system, can be employed. The latter system has been used to produce~200 mg/L of 6dEB in *S. coelicolor* but has not been examined for polyketide synthesis in *S. fradiae*. The tylG promoter in *S. fradiae* can produce high levels of tylosin, so tylGp is a good choice for 21 production in this host. One can standardize delta-lactone production in the various constructs extracted from the same fermentation sample because the syntheses of both tylosin and 21 will be under the control of tylGp (see below). Furthermore, because one ultimately desires to express the altered (or unaltered) DEBS such that it produces 15-MeEryA under control of the tylGp, one can subsequently transfer the ultimate construct within the context of the full DEBS PKS into *S. fradiae*.

Various plasmids that either replicate autonomously or integrate site-specifically at the phage phiC31 attachment site have been used to introduce genes into *S. fradiae* by protoplast transformation (59). Versions of both sets of plasmids carrying the oriT locus are available for conjugal transfer from *E. coli* (60). One can employ a set of plasmids that replicate autonomously or integrate into the chromosome site-specifically that contain or lack oriT. One can examine the frequency of transfer of these plasmids into the *S. fradiae* host employing the published methods to determine which plasmid and which transfer system is best to use to make the necessary constructs that make 21 and introduce them into the *S. fradiae* strain.

The *S. fradiae*/DEBS1-TE constructs are examined for production of the corresponding deltalactone 21 and tylosin, using growth conditions and metabolite isolation and assay methods for tylosin from the literature in conjunction with suitable methods for the delta-lactone. One will grow a number of independent isolates (transformants or transconjugants) of each strain under precise fermentation conditions and assay replicate samples. Polyketide products will be extracted from whole broth samples using $C_{18}$ reversed-phase resin and analyzed by LC-mass spectroscopy. Low-level products will be quantitated by comparison of integrated ion currents with a standard curve generated using pure samples. High-level products will be quantitated by evaporative light scattering. If necessary, one can also examine the samples for the pool sizes of various acyl-CoA thioesters to ensure that variations in the levels of production of 21 from the constructs are not the result of precursor supply fluctuations.

Although the normal DEBS1-TE gene under the control of tylGp can be used as a control for delta-lactone production in *S. fradiae*, it cannot be stated with certainty for any particular strain whether 14 or 21 will be made. This will depend upon the relative pool sizes of p-CoA and b-CoA and their relative rates of incorporation into the corresponding growing polyketide chains. If 21 is produced exclusively, it will not be necessary to re-engineer DEBS for 15-MeEryA production in *S. fradiae*.

After one determines which of the constructs yields the highest production of 21, one can use the exact segment to rebuild a PKS that can make 15-methyl-6dEB in *S. fradiae*. The most straightforward way to exchange the normal DEBS loading module with the altered loading module is to exchange a suitable restriction fragment containing tylGp-DEBS loading or altered DEBS loading domains—DEBS module 1 (to a convenient restriction site) with the corresponding fragment in eryA1 that includes sequences to eliminate upstream promoters. This will yield a segment containing the three DEBS (or modified DEBS) genes behind the tylG promoter. One can then insert these genes in a vector that can site specifically integrate in the chromosome of *S. fradiae* and disrupt the resident tylG genes. If this approach yields too little 15-methyl-6dEB, one can engineer the replacement of the tylG genes with the DEBS genes under the control of the tylG promoter. To accomplish this, one can clone the segment immediately downstream of the beginning of the tylG genes taking care to maintain the same PKS-downstream gene orientation as was present in the tyl cluster. This entire segment is placed in a suicide vector for the two-step recombination required for exchange of the tyl PKS with the ery (or modified ery) PKS genes. Production of 15-methyl-6dEB instead of 6dEB itself by this recombinant strain yields the desired result.

With this achieved, one can introduce the entire set of erythromycin biosynthesis genes, containing the engineered DEBS1 gene, into *S. fradiae*. Ideally, one will transfer the ery gene cluster from a suitable donor strain into a properly marked *S. fradiae* recipient by the method of Hu et al. (53b). One can employ a plasmid containing the entire ery gene cluster from *Sac. erythraea* and marked with a second gene tsr encoding thiostrepton resistance. The ery genes in this construct are flanked with approx. 2 kb segments of the tylosin gene cluster flanking the region into which the engineered ery genes are to be inserted. The eryAI PKS gene is replaced with the engineered version of DEBS1 described above. Finally, the two tra genes from pIJ101 that mediate the conjugal transfer of the ery gene cluster from the donor strain to *S. fradiae* are cloned onto the vector or provided in trans in the donor strain. Once these constructs and strains are made, conjugal mating of the donor strain (preferably a streptomycin-sensitive strain of *S. coelicolor*) with a streptomycin resistant, thiostrepton sensitive *S. fradiae* recipient strain followed by selection for thiostrepton resistance and counterselection of the donor strain by streptomycin results in transfer of the ery genes into *S. fradiae*. Preferably, the incoming genes replace most of the tylosin gene cluster, which should be sufficient to allow erythromycin production even if some of the other tylosin biosynthesis genes are still present. Because one can select for the desired result via thiostrepton, one can obtain the recombinant albeit at a very low transfer frequency. Alternatively, the following method can be employed.

One can provide *S. fradiae* the ability to produce and transfer desosamine and mycarose to 15-methylEB in accordance with the methods of the present invention. Because TDP-desosamine is required for the synthesis of 15-MeEryA, one can provide for its synthesis in *S. fradiae* as followings. The addition of the two desosaminyl-specific genes, eryCIV and eryCV, which are adjacent to each other and probably co-transcribed in *Sac. erythraea*, should divert the mycaminosyl pathway to result in the synthesis of the 5-O-desosaminyltylonolide [22] when cloned in *S. fradiae*.

22

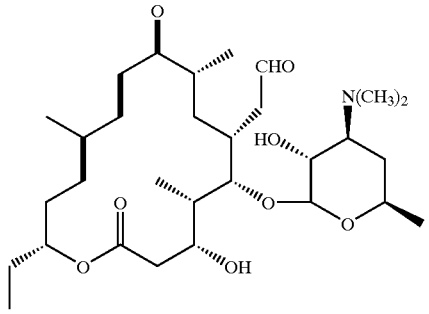

One can also add the gene eryCIII, the desosaminyltransferase, that is required to make 15-MeEryA in *S. fradiae*. The synthesis of 22 will require that 4' (see the schematic above) is produced by the addition of eryCIV and eryC, can be converted to TDP-desosamine by the enzyme that aminates 2' (see the schematic above) to yield TDP-mycaminose, and that the TDP-mycaminosyltransferase can add TDP-desosamine to the C-5 hydroxyl of tylonolide. Because one is not disrupting any of the tyl genes at this step, this all-or-none result would take place within the background of the host that still produces tylosin.

In the normal pathway of tylosin biosynthesis, the cognate intermediate (5-O-mycaminosyltylonolide) undergoes glycosylation at C-4' of the mycaminosyl moiety with TDP-mycarose. The absence of an OH group at C-4' would be expected to interrupt the pathway and result in the production of 22 as a final product. One can examine the fermentation broth for the presence of 22 by LC/MS and perform rigorous analyses to confirm the structure. If the compound is not produced, one can add 3-O-alphamycarosylerythronolide B, the natural substrate for the eryCIII-catalyzed transfer of TDP-desosamine, and look for the production of erythromycin D in the fermentation broth. Finding this compound will validate that the pathway to desosamine has been achieved in *S. fradiae*, even if one does not see 22 produced. If one does not observe erythromycin D, one can add the additional genes eryCI and eryCVI to *S. fradiae* and again look for the synthesis of 22 in unfed cultures or erythromycin D in cultures fed with 3-O-alpha-mycarosylerythronolide B. Once the desosamine pathway in *S. fradiae* is produced, one can then introduce the gene eryBV, the transferase which adds mycarose to the C-3 OH position of erythronolide B. One can confirm the activity of EryBV by the identification of the compound 3-O-alphamycarosylerythronolide B in fermentations which are fed with erythronolide B. If the presence of the TDP-mycaminose pathway interferes with the production of 22, one can disrupt tylJ to eliminate the synthesis of this sugar (61).

The gene eryF (or a gene with similar activity) is introduced, under the control of the ermE* promoter into the *S. fradiae* host that contains the eryC and B genes. Its activity will be confirmed by demonstrating efficient conversion of 6-dEB to erythromycin D when 6-dEB is fed to fermentation cultures. Similarly, eryK (or a gene with similar activity) is introduced in the host containing the required eryB, eryC and eryF genes and its function confirmed by demonstrating efficient conversion 6-dEB to erythromycin C when 6-dEB is fed to fermentation cultures.

Placement of DEBS in the *S. fradiae* chromosome behind the tylG promoter can be done in three steps: (i) a delivery plasmid containing the DEBS genes behind tylGp and at least a 1 kb sequence downstream of tylG5 (tylG5ds) is built using PCR or restriction fragments from the genome of *S. fradiae*, the loading module from tylGp-DEBS1 (or modified tylGp-DEBS1-TE), and the full DEBS genes; (ii) the tylG genes are removed from the chromosome of *S. fradiae* in a two-step homologous replacement experiment employing similar tylGp and downstream sequences; and (iii) the tylGp-DEBS-tylG5ds segment is exchanged in a two-step homologous recombination experiment with the tylG-free sequence in the chromosome. This will leave the host with DEBS free of tylG PKS sequences. Furthermore, the expression of the DEBS genes under tylGp will be regulated similarly to those of the tylG genes in the unmodifed *S. fradiae* host. The cloning described allows the *S. fradiae* host to produce 15-MeEryC from b-CoA and mm-CoA.

Conversion of 15-MeEryC to 15-MeEryA is dependent upon the presence of the gene eryG. Because ketolide antibacterials have no sugar at the 3-position, either 15-MeEryC or 15-MeEryA is a suitable starting material. Therefore, if one obtain 15-MeEryC through the cloning in *S. fradiae* described here, one can attempt its conversion to 15-MeEryA through the introduction of eryG if desired, but this is not required if the strain is used to make an intermediate used in ketolide production.

The following references have been referred to in this example by the number preceding each reference listed below.

1. Brisson-Noel, A., et. al. Mechanism of action of spiramycin and other macrolides. *J. Antimicrob. Chemother.* 22 (Supp. B), 13–33 (1988).
2. Moazed, D. & Noller, H. F. Chloramphenicol, carbomycin and vernamycin B protect overlapping 5sites in the peptidyl transferase region of 23S ribosomal RNA. *Biochemie* 69, 879–884 (1987).
3. Lai, C. & Weisblum, B. Altered methylation of ribosomal RNA in an erythromycin-resistant strain of *Staphylococcus aureus*. *Proc. Nat. Acad. Sci. USA* 68, 856–860 (1971).
4. Sutcliffe, J. Resistance to macrolides mediated by efflux mechanisms. *Curr. Opin. Anti-infect. Investig. Drugs* 1, 403–412 (1999).
5. Biedenbach, D. J. & Jones, R. N. In vitro evaluation of new ketolides RU-64004 and RU-66647 against macrolide-resistant Gram positive pathogens. 36*th Intersci. Conf. Antibact. Agents Chemother.*, F221 (1996).
6. Ma, Z., et al. Design, synthesis, and characterization of ABT-773; a novel ketolide highly active against multidrug-resistant pathogens. 39*th Intersci. Conf. Antimicrob. Agents. Chemother.*, 345 (1999).
7. Skinner, D. D., et al. Cloning and sequencing of a cluster of genes encoding branched-chain alpha-keto acid dehydrogenase from *Streptomyces avermitilis* and the production of a functional E1 [alpha beta] component in *Escherichia coli*. *J Bacteriol* 177, 183–190 (1995).
8. Omura, S. et al. Valine as a precursor of n-butyrate unit in the biosynthesis of macrolide aglycone. *J. Antibiot.* 36, 614–616 (1983).
9. Lee, S. H. & Rho, Y. T. Improvement of tylosin fermentation by mutation and medium optimization. *Lett. Appl. Microbiol.* 28, 142–144 (1999).
10. Lounes, A., et. al. Regulation of valine catabolism by ammonium in *Streptomyces ambofaciens*, producer of spiramycin. *Can. J. Microbiol.* 41, 800–808 (1995).
11. Tang, L., et al. Amino acid catabolism and antibiotic synthesis: valine is a source of precursors for macrolide biosynthesis in *Streptomyces ambofaciens* and *Streptomyces fradiae*. *J. Bacteriol* 176, 6107–6119 (1994).
12. Tang, L. & Hutchinson, C. R. Regulation of expression of the valine (branched-chain amino acid) dehydrogenase-encoding gene from *Streptomyces coelicolor. Gene* 30, 69–74 (1995).
13. Zhang, Y. X., et al. Genes encoding acyl-CoA dehydrogenase (AcdH) homologues from *Streptomyces coelicolor* and *Streptomyces avermitilis* provide insights into the metabolism of small branched-chain fatty acids and macrolide antibiotic production. *Microbiology* 145, 2323–2334 (1999).
14. Wallace, K., et al. In vivo and in vitro effects of thiolactomycin on fatty acid biosynthesis in *Streptomyces collinus. J Bacteriol* 179, 3884–3891 (1997).
15. Reynolds, K. A., et al. Butyrate metabolism in streptomycetes. Characterization of an inter-change rearrangement linking isobutyrate and butyrate in *Streptomyces cinnamonensis. J. Chem. Soc. Perkin Trans. I*, 3195–3207 (1988).
16. Tuan, J. S. et al. Cloning of genes involved in erythromycin biosynthesis from *Saccharopolyspora erythraea* using a novel actinomycete-*Escherichia coli* cosmid. *Gene* 90, 21–29 (1990).
17. Donadio, S., et al. Erythromycin production in *Saccharopolyspora erythraea* does not require a functional propionyl-CoA carboxylase. *Mol. Microbiol.* 19, 977–984 (1996).
18. Hsieh, Y. J. & Kolattukudy, P. E. Inhibition of erythromycin synthesis by disruption of malonyl-coenzyme A decarboxylase gene eryM in *Saccharopolyspora erythraea. J Bacteriol* 176, 714–724 (1994).
19. McAlpine, J. B. et al. New antibiotics from genetically engineered actinomycetes I. 2-norerythromycins, isolation and structural determinations. *J. Antibiot.* 40, 1115–1122 (1987).
20. Vrijbloed, J. W., et al. Insertional inactivation of methylmalonyl coenzyme A (CoA) mutase and isobutyryl-CoA mutase genes in *Streptomyces cinnamonensis*: influence on polyketide antibiotic biosynthesis. *J Bacteriol* 181, 5600–5605 (1999).
21. Wallace, K. K. et al. Purification of crotonyl-CoA reductase from *Streptomyces collinus* and cloning, sequencing and expression of the corresponding gene in *Escherichia coli. Eur J. Biochem* 233, 954–962 (1995).
22. Stassi, D. L. et al. Ethyl-substituted erythromycin derivatives produced by directed metabolic engineering. *Proc. Natl. Acad. Sci. USA* 95, 7305–7309 (1998).
23. Bate, N., et al. Multiple regulatory genes in the tylosin biosynthetic cluster of *Streptomyces fradiae. Chem Biol* 6, 617–624 (1999).
24. Wallace, K., et al. In vivo analysis of straight-chain and branched-chain fatty acid biosynthesis in three actinomycetes. *FEMS Microbiol Lett*, 227–234 (1995).
25. Zerbe-Burkhardt, K. et al. Cloning, sequencing, expression, and insertional inactivation of the gene for the large subunit of the coenzyme B 12-dependent isobutyryl-CoA mutase from *Streptomyces cinnamonensis. J Biol Chem* 273, 6508–6517 (1998).
26. Ratnatilleke, A., et al. Cloning and sequencing of the coenzyme B12-binding domain of isobutyryl-CoA mutase from *Streptomyces cinnamonesis*. Reconstitution of mutase activity, and characterization of the recombinant enzyme produced in *Escherichia coli. Biological Chemistry* 274, 1–7 (1999).
27. Katz, L. Manipulation of modular polyketide synthases. *Chem. Rev.* 97, 2557–2575 (1997).
28. Kao, C. M., et al. Engineered biosynthesis of a triketide lactone from an incomplete modular polyketide synthase. *J. Am. Chem. Soc.* 116, 11612–11613 (1994).
29. Marsden, A. F. et al. Engineering broader specificity into an antibiotic-producing polyketide synthase. *Science* 279, 199–202 (1998).
30. Pieper, R., et al. Remarkably broad substrate specificity of a modular polyketide synthase in a cell-free system. *J. Am. Chem. Soc.* 117, 11373–11374 (1995).
31. DeHoff, B. S., et al. GenBank Accession No. U78289.
32. Witkowski, A., et al. Conversion of a b-ketoacyl synthase to a malonyl decarboxylase by replacement of the active-Site cysteine with glutamine. *Biochemistry* (in press).
33. Bisang, C. et al. A chain initiation factor common to both modular and aromatic polyketide synthases. *Nature* 401, 502–505 (1999).
34. Schwecke, T. et al. The biosynthetic gene cluster for the polyketide immunosuppressant rapamycin. *Proc Natl Acad Sci USA* 92, 7839–7843 (1995).
35. Xue, Y., et al. A gene cluster for macrolide antibiotic biosynthesis in *Streptomyces venezuelae*: architecture of metabolic diversity. *Proc Natl Acad Sci USA* 95, 12111–12116 (1998).
36. Ikeda, H., et al. Organization of the biosynthetic gene cluster for the polyketide anthelmintic macrolide avermectin in *Streptomyces avermitilis. Proc Natl Acad Sci USA* 96, 9509–9514 (1999).
37. Motamedi, H. & Shafiee, A. The biosynthetic gene cluster for the macrolactone ring of the immunosuppressant FK506. *Eur J Biochem* 256, 528–534 (1998).
38. Tang, L., et al. Characterization of the enzymatic domains in the modular polyketide synthase involved in rifamycin B biosynthesis by *Amycolatopsis mediterranei. Gene* 216, 255–265 (1998).
39. Donadio, S., et al. Modular organization of genes required for complex polyketide biosynthesis. *Science* 252, 675–679 (1991).
40. Ruan, X. et al. Acyltransferase domain substitutions in erythromycin polyketide synthase yield novel erythromycin derivatives. *J Bacteriol* 179, 6416–6425 (1997).
41. Oliynyk, M., et al. A hybrid modular polyketide synthase obtained by domain swapping. *Chem Biol* 3, 833–839 (1996).
42. McDaniel, R. et al. Multiple genetic modifications of the erythromycin polyketide synthase to produce a library of novel "unnatural" natural products [published erratum appears in *Proc Natl Acad Sci USA* May 11, 1999;96(10):5890]. *Proc Natl Acad Sci USA* 96, 1846–1851 (1999).
43. Kuhstoss, S. et al. Production of a novel polyketide through the construction of a hybrid polyketide synthase. *Gene* 183, 231–236 (1996).
44. Marsden, A. F. et al. Engineering broader specificity into an antibiotic-producing polyketide synthase. *Science* 279, 199–202 (1998).
45. Kao, C. M., et al Engineered biosynthesis of a complete macrolactone in a heterologous host. *Science* 265, 509–512 (1994).
46. Kao, C. M., et al. Engineered biosynthesis of a triketide lactone from an incomplete modular polyketide synthase. *J. Am. Chem. Soc.* 116, 11612–11613 (1994).
47. Jacobsen, J. R., et al. Precursor-directed biosynthesis of erythromycin analogs by an engineered polyketide synthase. *Science* 277, 367–369 (1997).
48. Weissman, K. J. et al. Evaluating precursor-directed biosynthesis towards novel erythromycins through in vitro studies on a bimodular polyketide synthase. *Chem Biol* 5, 743–754 (1998).

49. Summers, R. G. et al. Sequencing and mutagenesis of genes from the erythromycin biosynthetic gene cluster of *Saccharopolyspora erythraea* that are involved in L-mycarose and D-desosamine production. *Microbiology* 143, 3251–3262 (1997).
50. Gaisser, S., et al. Analysis of seven genes from the eryAI-eryK region of the erythromycin biosynthetic gene cluster in *Saccharopolyspora erythraea. Mol Gen Genet* 256, 239–251 (1997).
51. Gaisser, S. et al. Analysis of eryBI, eryBIII and eryBVII from the erythromycin biosynthetic gene cluster in *Saccharopolyspora erythraea. Mol Gen Genet* 258, 78–88 (1998).
51a. Merson-Davies et al., Analysis of five tylosin biosynthetic genes from the tylBA region of the *Streptomyces fradiae* genome. *Mol. Microbiol.* 13, 349–355 (1997)
51b. Gandecha, A. R. et al. Analysis of four tylosin biosynthetic genes from the tylLM region of the *Streptomyces fradiae* genome. *Gene* 184, 197–203 (1994).
52. Morimoto, S., et al. Chemical modification of erythromycins. I. Synthesis and antibacterial activity of 6-O-methylerythromycins A. *J. Antibiot.* 37, 187–189 (1984).
53. Agouridas, C. et al. Synthesis and antibacterial activity of ketolides (6-O-methyl-3-oxoerythromycin derivatives): a new class of antibacterials highly potent against macrolide-resistant and -susceptible respiratory pathogens. *J. Med. Chem.* 41, 4080–4100 (1998).
53a. Davisson, J. W. et al. Rimocidin, a new antibiotic. *Antibiot. Chemother.* 1, 289–290 (1951).
53b. Hu, Z. et al. Directed transfer of large DNA fragments between Streptomyces species. *Appl. Environ. Microbiol.* 66, 2274–2277 (2000).
54. Pereda, A., et al. Nucleotide sequence of the ermE distal flank of the erythromycin biosynthesis cluster in *Saccharopolyspora erythraea. Gene* 193, 65–71 (1997).
55. Baltz, R. H. & Hosted, T. J. Molecular genetic methods for improving secondary-metabolite production in actinomycetes. *Tibtech* 14, 245–250 (1996).
56. Hosokawa, Y., et al. Determination of short-chain acyl-coenzyme A esters by high-performance liquid chromatography. *Analytical Biochemistry*, 45–49 (1985).
57. Kikuchi, M., et al. Assay of methylmalonyl CoA mutase with high-performance liquid chromatography. *Clinica Chimica Acta* 184, 307–314 (1989).
57a. Rangan V S & Smith S. Alteration of the substrate specificity of the malonyl-CoA/acetyl-CoA:acyl carrier protein S-acyltransferase domain of the multifunctional fatty acid synthase by mutation of a single arginine residue. *J Biol Chem.* 272, 11975–8 (1997).
58. Kakavas, S. J., et al. Identification and characterization of the niddamycin polyketide synthase genes from *Streptomyces caelestis. J Bacteriol* 179, 7515–7522 (1997).
58a. Ranganathan A. et al. Knowledge-based design of bimodular and trimodular polyketide synthases based on domain and module swaps: a route to simple statin analogues. *Chem. Biol.* 6, 731–741 (1999).
59. Matsushima, P. & Baltz, R. H. Efficient plasmid transformation of *Streptomyces ambofaciens* and *Streptomyces fradiae* protoplasts. *J Bacteriol* 163, 180–185 (1985).
60. Bierman, M. et al. Plasmid cloning vectors for the conjugal transfer of DNA from *Escherichia coli* to Streptomyces spp. *Gene* 116, 43–49 (1992).
61. Bate, N. & Cundliffe, E. The mycinose-biosynthetic genes of *Streptomyces fradiae*, producer of tylosin. *J Ind Microbiol Biotechnol* 23, 118–122 (1999).

The invention having now been described by way of written description and example, those of skill in the art will recognize that the invention can be practiced in a variety of embodiments and that the foregoing description and examples are for purposes of illustration and not limitation of the following claims.

What is claimed is:

1. A recombinant *Saccharopolyspora erythraea* host cell, said host cell lacking a functional eryM gene or gene product and comprising an expression vector for a ccr gene from *Streptomyces collinus* or *Streptomyces coelicolor*, wherein said host cell makes 15-methyl-6-deoxyerythronolide B and butyryl CoA.

2. The host cell of claim 1, wherein said host cell further comprises a propionyl CoA carboxylase produced by recombinant pccA and pccB genes of *Streptomyces coelicolor* that converts propionyl CoA to methylmalonyl CoA.

3. The host cell of claim 1, wherein said host cell further comprises recombinant acsA, bdh, and ech genes from *Streptomyces coelicolor*.

4. The host cell of claim 1, wherein said host cell further comprises a recombinant vdh gene of *Streptomyces coelicolor*, *Streptomyces fradiae*, or *Streptomyces cinnamonensis*.

5. The host cell of claim 3, wherein said host cell further comprises recombinant icmA and icmB genes of *Streptomyces cinnamonensis*.

6. The host cell of claim 1 that comprises a recombinant eryAI gene in which the coding sequence for the loading domain has been altered
from having a methylmalonyl-specific acyltransferase (AT) domain and an acyl carrier protein (ACP) domain, designated mmAT-ACP,
to having a ketosynthase (KS) domain of a modular polyketide synthase, an ethylmalonyl-specific AT domain, and an ACP domain, designated $KS^Q$-emAT-ACP,
wherein the added KS domain has a glutamine instead of a cysteine in its active site ($KS^Q$).

7. The host cell of claim 6, wherein said host cell further comprises a propionyl CoA carboxylase produced by recombinant pccA and pccB genes of *Streptomyces coelicolor* that converts propionyl CoA to methylmalonyl CoA.

8. The host cell of claim 6, wherein said host cell further comprises recombinant acsA, bdh, and ech genes from *Streptomyces coelicolor*.

9. The host cell of claim 6, wherein said host cell further comprises a recombinant vdh gene of *Streptomyces coelicolor*, *Streptomyces fradiae*, or *Streptomyces cinnamonensis*.

10. The host cell of claim 6, wherein said host cell further comprises recombinant icmA and icmB genes of *Streptomyces cinnamonensis*.

11. The host cell of claim 1, wherein said ccr gene is from *Streptomyces collinus*.

12. The host cell of claim 6, wherein said ccr gene is from *Streptomyces collinus*.

* * * * *

SEQUENCE LISTING

```
<160> NUMBER OF SEQ ID NOS: 5

<210> SEQ ID NO 1
<211> LENGTH: 1980
<212> TYPE: DNA
<213> ORGANISM: Saccharopolyspora erythraea
<220> FEATURE:
<221> NAME/KEY: CDS
<222> LOCATION: (343)...(1594)

<400> SEQUENCE: 1
gatctggatg tcgaagccgg gacggagcgg gatgacggcg tcagcggcgt cttccatgtg      60
gaactcctta tccggacgac tcgacctggt tggctaagcg gagattaggt ctgcgcgcgc     120
gaaaccgccc agcggagcgc cgagatcctc acctgatcag gtaaggatct tcattcgatg     180
tcatgtagcc agatttcggc tgaactggtc cacgatcccg attcgtgacc atgcgtgtcc     240
actttggagc gggtgcgttc gttcggccta gtggcgtgct ccgcggtgat caagtgttag     300
gttagcctca gctcagcggg gtcgacggat ggagtgaacg gc gtg gcg ggc gac        354
                                                Val Ala Gly Asp
                                                  1 gtg gaa ctc gcg gac agg gct cga cga cgc gcg tgc cgg ctg ctc agg      402
Val Glu Leu Ala Asp Arg Ala Arg Arg Ala Cys Arg Leu Leu Arg
  5              10              15              20 cgt tgg ctg gcc gag acg cac act ccg gtg gag ccc ggc ccg ctg tcc      450
```

```
Arg Trp Leu Ala Glu Thr His Thr Pro Val Glu Pro Gly Pro Leu Ser
                25                  30                  35 ctg cgg atc ggc ccg gtg cgg gtg tcg gcc gag gtc gct tac cgc tcg      498
Leu Arg Ile Gly Pro Val Arg Val Ser Ala Glu Val Ala Tyr Arg Ser
            40                  45                  50 ccg acg ggc gcc cac ggg ttc ggc ccg atc cgc gtc ctc gat gcc gag      546
Pro Thr Gly Ala His Gly Phe Gly Pro Ile Arg Val Leu Asp Ala Glu
        55                  60                  65 ggt gtg ccg gtg gcg ctc gcc gat ccg gtg ctg ctg gcg gcc gcc tgc      594
Gly Val Pro Val Ala Leu Ala Asp Pro Val Leu Leu Ala Ala Ala Cys
    70                  75                  80 tcg gcg gac tcg cgg agc cgc tcg ctg ccg agc gcg ccg atc aac gcc      642
Ser Ala Asp Ser Arg Ser Arg Ser Leu Pro Ser Ala Pro Ile Asn Ala
85                  90                  95                 100 ccg gac gcc ggt acc gct gtc gac tgg gtg ctc tcg tcg ctc gcc gac      690
Pro Asp Ala Gly Thr Ala Val Asp Trp Val Leu Ser Ser Leu Ala Asp
                105                 110                 115 gac gag gac gac gag gtg ccc gcc ggc atg acc gcg gag gag gcg gtg      738
Asp Glu Asp Asp Glu Val Pro Ala Gly Met Thr Ala Glu Glu Ala Val
            120                 125                 130 cgc ctg ctg tcg cgg cag gtc gac gac ctg ccg cgg tcg ccg ggc gcc      786
Arg Leu Leu Ser Arg Gln Val Asp Asp Leu Pro Arg Ser Pro Gly Ala
        135                 140                 145 gac ccg tgg tcg ctg gtc gcc ggc ccg ctg gcg gcc atc ggg cgg ttc      834
Asp Pro Trp Ser Leu Val Ala Gly Pro Leu Ala Ala Ile Gly Arg Phe
    150                 155                 160 ggg cgg gcc ggg atc gcc gac gag tgc tgg ttg ctg gag gtg ctc gcc      882
Gly Arg Ala Gly Ile Ala Asp Glu Cys Trp Leu Leu Glu Val Leu Ala
165                 170                 175                 180 ggg cgg ctc cgc gcg gtc gac gac gac ctg tcc cgc tcg tgg ctg agc      930
Gly Arg Leu Arg Ala Val Asp Asp Asp Leu Ser Arg Ser Trp Leu Ser
                185                 190                 195 agt ccg acg ctc gcc gac cgc gct gtg ctc gtg ggt gag ggg ttg cgc      978
Ser Pro Thr Leu Ala Asp Arg Ala Val Leu Val Gly Glu Gly Leu Arg
            200                 205                 210 tac cgg ccg gat gtg cgg ccg gtg ccg ttc gac gtg ccg aac ccg ctg     1026
Tyr Arg Pro Asp Val Arg Pro Val Pro Phe Asp Val Pro Asn Pro Leu
        215                 220                 225 cac gag ggc aag tcc gac gtc ccg ccg ccg ccc gtg ccc gtg ctg ggc     1074
His Glu Gly Lys Ser Asp Val Pro Pro Pro Pro Val Pro Val Leu Gly
    230                 235                 240 ggg ccg tgg tcg ctg cgt ccg gtc gag gtc gcg gtc cac ggg gat ggc     1122
Gly Pro Trp Ser Leu Arg Pro Val Glu Val Ala Val His Gly Asp Gly
245                 250                 255                 260 ggg cct gac gtc gca ctg gtg cac cgc tgg atg aac acc ccg cac gtc     1170
Gly Pro Asp Val Ala Leu Val His Arg Trp Met Asn Thr Pro His Val
                265                 270                 275 gcg cac cac tgg aac cag gcg tgg ccg ctg gag cgc tgg cgg gag gaa     1218
Ala His His Trp Asn Gln Ala Trp Pro Leu Glu Arg Trp Arg Glu Glu
            280                 285                 290 ctc gcc cac cag ctc ggc ggt gag cac tcc ctg ccc tgc gtg gtc gga     1266
Leu Ala His Gln Leu Gly Gly Glu His Ser Leu Pro Cys Val Val Gly
        295                 300                 305 cac gag gga cgc gag gtc gcg tat ctg gag ctc tac cgg gtg acc cgc     1314
His Glu Gly Arg Glu Val Ala Tyr Leu Glu Leu Tyr Arg Val Thr Arg
    310                 315                 320 gac aag ctt gcg ggc tgc tac ccg tac ggg ccg cac gac ctc ggg gtc     1362
Asp Lys Leu Ala Gly Cys Tyr Pro Tyr Gly Pro His Asp Leu Gly Val
325                 330                 335                 340
```

-continued

```
cac atc gcg atc ggc gag cgg gag gtg ctc ggg cgc ggt ttc ggg tcg      1410
His Ile Ala Ile Gly Glu Arg Glu Val Leu Gly Arg Gly Phe Gly Ser
            345                 350                 355 tcg ctg ctg cgc gcg gtc gcg ggt gcg ctg ctg gac gcc gat ccg cgg      1458
Ser Leu Leu Arg Ala Val Ala Gly Ala Leu Leu Asp Ala Asp Pro Arg
        360                 365                 370 tgc gcg cgg gtg gtc gcc gag ccg aat gtg cac aac gag gct tcg gtg      1506
Cys Ala Arg Val Val Ala Glu Pro Asn Val His Asn Glu Ala Ser Val
    375                 380                 385 cgc gcc ttc gcc aag gcc ggg ttc gtc cgg gag agg gag atc ggc ctg      1554
Arg Ala Phe Ala Lys Ala Gly Phe Val Arg Glu Arg Glu Ile Gly Leu
390                 395                 400 ccc gcc aag aac tcg gct ctg atg gtc ttc tcc cgg gtc t gacgaccggt    1604
Pro Ala Lys Asn Ser Ala Leu Met Val Phe Ser Arg Val
405                 410                 415 catgcccctg tgtgaacgcg tgagtaagcg caccgtgacg tgatccccg cttgaaccaa    1664 ggttagcctt acttttattg gtggagaacg atgccggagc gctccgccgt gtcgttgccg    1724
ctgaccacag cgcagtaggg catctggttc gcccagcaac tcgaccggac gaacccgatc    1784
tacaacaccg gcgagtgcgt cgagatcagc ggccggtgg agccggtggt gttcgagcag    1844
gccctgcggt ggggcgtggc ggaggccgag gcgctgcgag cccgcgtggt cgtcgacggc    1904
gacgagccgc gccaggtcgt ggagccggag gtggacttcc cgctgccgtg ctcgacgtca    1964
gcgccgaggc ggaccc                                                    1980
```

<210> SEQ ID NO 2
<211> LENGTH: 417
<212> TYPE: PRT
<213> ORGANISM: Saccharopolyspora erythraea

<400> SEQUENCE: 2

```
Val Ala Gly Asp Val Glu Leu Ala Asp Arg Ala Arg Arg Arg Ala Cys
1               5                   10                  15

Arg Leu Leu Arg Arg Trp Leu Ala Glu Thr His Thr Pro Val Glu Pro
            20                  25                  30

Gly Pro Leu Ser Leu Arg Ile Gly Pro Val Arg Val Ser Ala Glu Val
        35                  40                  45

Ala Tyr Arg Ser Pro Thr Gly Ala His Gly Phe Gly Pro Ile Arg Val
    50                  55                  60

Leu Asp Ala Glu Gly Val Pro Val Ala Leu Ala Asp Pro Val Leu Leu
65                  70                  75                  80

Ala Ala Ala Cys Ser Ala Asp Ser Arg Ser Arg Ser Leu Pro Ser Ala
                85                  90                  95

Pro Ile Asn Ala Pro Asp Ala Gly Thr Ala Val Asp Trp Val Leu Ser
            100                 105                 110

Ser Leu Ala Asp Asp Glu Asp Glu Val Pro Ala Gly Met Thr Ala
        115                 120                 125

Glu Glu Ala Val Arg Leu Leu Ser Arg Gln Val Asp Asp Leu Pro Arg
    130                 135                 140

Ser Pro Gly Ala Asp Pro Trp Ser Leu Val Ala Gly Pro Leu Ala Ala
145                 150                 155                 160

Ile Gly Arg Phe Gly Arg Ala Gly Ile Ala Asp Glu Cys Trp Leu Leu
                165                 170                 175

Glu Val Leu Ala Gly Arg Leu Arg Ala Val Asp Asp Leu Ser Arg
            180                 185                 190

Ser Trp Leu Ser Ser Pro Thr Leu Ala Asp Arg Ala Val Leu Val Gly
```

```
                195                 200                 205
Glu Gly Leu Arg Tyr Arg Pro Asp Val Arg Pro Val Pro Phe Asp Val
            210                 215                 220

Pro Asn Pro Leu His Glu Gly Lys Ser Asp Val Pro Pro Pro Val
225                 230                 235                 240

Pro Val Leu Gly Gly Pro Trp Ser Leu Arg Pro Val Glu Val Ala Val
                245                 250                 255

His Gly Asp Gly Gly Pro Asp Val Ala Leu Val His Arg Trp Met Asn
            260                 265                 270

Thr Pro His Val Ala His His Trp Asn Gln Ala Trp Pro Leu Glu Arg
            275                 280                 285

Trp Arg Glu Glu Leu Ala His Gln Leu Gly Gly Glu His Ser Leu Pro
    290                 295                 300

Cys Val Val Gly His Glu Gly Arg Glu Val Ala Tyr Leu Glu Leu Tyr
305                 310                 315                 320

Arg Val Thr Arg Asp Lys Leu Ala Gly Cys Tyr Pro Tyr Gly Pro His
                325                 330                 335

Asp Leu Gly Val His Ile Ala Ile Gly Glu Arg Glu Val Leu Gly Arg
            340                 345                 350

Gly Phe Gly Ser Ser Leu Leu Arg Ala Val Ala Gly Ala Leu Leu Asp
    355                 360                 365

Ala Asp Pro Arg Cys Ala Arg Val Val Ala Glu Pro Asn Val His Asn
370                 375                 380

Glu Ala Ser Val Arg Ala Phe Ala Lys Ala Gly Phe Val Arg Glu Arg
385                 390                 395                 400

Glu Ile Gly Leu Pro Ala Lys Asn Ser Ala Leu Met Val Phe Ser Arg
                405                 410                 415

Val

<210> SEQ ID NO 3
<211> LENGTH: 929
<212> TYPE: PRT
<213> ORGANISM: Saccharopolyspora eruthraea

<400> SEQUENCE: 3

Met His Val Pro Gly Glu Glu Asn Gly His Ser Ile Ala Ile Val Gly
1               5                   10                  15

Ile Ala Cys Arg Leu Pro Gly Ser Ala Thr Pro Gln Glu Phe Trp Arg
            20                  25                  30

Leu Leu Ala Asp Ser Ala Asp Ala Leu Asp Glu Pro Pro Ala Gly Arg
        35                  40                  45

Phe Pro Thr Gly Ser Leu Ser Ser Pro Pro Ala Pro Arg Gly Gly Phe
    50                  55                  60

Leu Asp Ser Ile Asp Thr Phe Asp Ala Asp Phe Phe Asn Ile Ser Pro
65                  70                  75                  80

Arg Glu Ala Gly Val Leu Asp Pro Gln Gln Arg Leu Ala Leu Glu Leu
                85                  90                  95

Gly Trp Glu Ala Leu Glu Asp Ala Gly Ile Val Pro Arg His Leu Arg
            100                 105                 110

Gly Thr Arg Thr Ser Val Phe Met Gly Ala Met Trp Asp Asp Tyr Ala
        115                 120                 125

His Leu Ala His Ala Arg Gly Glu Ala Ala Leu Thr Arg His Ser Leu
    130                 135                 140

Thr Gly Thr His Arg Gly Met Ile Ala Asn Arg Leu Ser Tyr Ala Leu
```

-continued

```
             145                 150                 155                 160
Gly Leu Gln Gly Pro Ser Leu Thr Val Asp Thr Gln Ser Ser Ser
                 165                 170                 175
Leu Ala Ala Val His Met Ala Cys Glu Ser Leu Ala Arg Gly Glu Ser
                 180                 185                 190
Asp Leu Ala Leu Val Gly Gly Val Asn Leu Val Leu Asp Pro Ala Gly
                 195                 200                 205
Thr Thr Gly Val Glu Arg Phe Gly Ala Leu Ser Pro Asp Gly Arg Cys
             210                 215                 220
Tyr Thr Phe Asp Ser Arg Ala Asn Gly Tyr Ala Arg Gly Glu Gly Gly
225                 230                 235                 240
Val Val Val Leu Lys Pro Thr His Arg Ala Leu Ala Asp Gly Asp
                 245                 250                 255
Thr Val Tyr Cys Glu Ile Leu Gly Ser Ala Leu Asn Asn Asp Gly Ala
                 260                 265                 270
Thr Glu Gly Leu Thr Val Pro Ser Ala Arg Ala Gln Ala Asp Val Leu
                 275                 280                 285
Arg Gln Ala Trp Glu Arg Ala Arg Val Ala Pro Thr Asp Val Gln Tyr
             290                 295                 300
Val Glu Leu His Gly Thr Gly Thr Pro Ala Gly Asp Pro Val Glu Ala
305                 310                 315                 320
Glu Gly Leu Gly Thr Ala Leu Gly Thr Ala Arg Pro Ala Glu Ala Pro
                 325                 330                 335
Leu Leu Val Gly Ser Val Lys Thr Asn Ile Gly His Leu Glu Gly Ala
                 340                 345                 350
Ala Gly Ile Ala Gly Leu Leu Lys Thr Val Leu Ser Ile Lys Asn Arg
             355                 360                 365
His Leu Pro Ala Ser Leu Asn Phe Thr Ser Pro Asn Pro Arg Ile Asp
             370                 375                 380
Leu Asp Ala Leu Arg Leu Arg Val His Thr Ala Tyr Gly Pro Trp Pro
385                 390                 395                 400
Ser Pro Asp Arg Pro Leu Val Ala Gly Val Ser Ser Phe Gly Met Gly
                 405                 410                 415
Gly Thr Asn Cys His Val Val Leu Ser Glu Leu Arg Asn Ala Gly Gly
                 420                 425                 430
Asp Gly Ala Gly Lys Gly Pro Tyr Thr Gly Thr Glu Asp Arg Leu Gly
             435                 440                 445
Ala Thr Glu Ala Glu Lys Arg Pro Asp Pro Ala Thr Gly Asn Gly Pro
             450                 455                 460
Asp Pro Ala Gln Asp Thr His Arg Tyr Pro Pro Leu Ile Leu Ser Ala
465                 470                 475                 480
Arg Ser Asp Ala Ala Leu Arg Ala Gln Ala Glu Arg Leu Arg His His
                 485                 490                 495
Leu Glu His Ser Pro Gly Gln Arg Leu Arg Asp Thr Ala Tyr Ser Leu
                 500                 505                 510
Ala Thr Arg Arg Gln Val Phe Glu Arg His Ala Val Val Thr Gly His
                 515                 520                 525
Asp Arg Glu Asp Leu Leu Asn Gly Leu Arg Asp Leu Glu Asn Gly Leu
             530                 535                 540
Pro Ala Pro Gln Val Leu Leu Gly Arg Thr Pro Thr Pro Glu Pro Gly
545                 550                 555                 560
Gly Leu Val Phe Val Phe Pro Gly Gln Gly Pro Gln Trp Arg Gly Met
                 565                 570                 575
```

-continued

```
Gly Val Glu Leu Met Ala Ala Ser Pro Val Phe Ala Ala Arg Met Arg
            580                 585                 590
Gln Cys Ala Asp Ala Leu Ile Pro His Thr Gly Trp Asp Pro Ile Ala
        595                 600                 605
Met Leu Asp Asp Pro Glu Val Thr Arg Arg Val Asp Val His Pro
    610                 615                 620
Val Cys Trp Ala Val Met Val Ser Leu Ala Ala Val Trp Glu Ala Ala
625                 630                 635                 640
Gly Val Arg Pro Asp Ala Val Ile Gly His Ser Gln Gly Glu Ile Ala
                645                 650                 655
Ala Ala Cys Val Ala Gly Ala Leu Thr Leu Glu Asp Gly Ala Arg Leu
            660                 665                 670
Val Ala Leu Arg Ser Val Leu Leu Leu Arg Glu Leu Ala Gly Arg
        675                 680                 685
Gly Ala Met Gly Ser Val Ala Leu Pro Ala Ala Asp Val Glu Ala Asp
    690                 695                 700
Ala Ala Arg Ile Asp Gly Val Trp Val Ala Gly Arg Asn Gly Ala Thr
705                 710                 715                 720
Thr Thr Thr Val Ala Gly Arg Pro Asp Ala Val Glu Thr Leu Ile Ala
                725                 730                 735
Asp Tyr Glu Ala Arg Gly Val Trp Val Arg Arg Ile Ala Val Asp Cys
            740                 745                 750
Pro Thr His Thr Pro Phe Val Asp Pro Leu Tyr Asp Glu Leu Gln Arg
        755                 760                 765
Ile Val Ala Asp Thr Thr Ser Arg Thr Pro Glu Ile Pro Trp Phe Ser
    770                 775                 780
Thr Ala Asp Glu Arg Trp Ile Asp Ala Pro Leu Asp Asp Glu Tyr Trp
785                 790                 795                 800
Phe Arg Asn Met Arg His Pro Val Gly Phe Ala Thr Ala Val Thr Ala
                805                 810                 815
Ala Arg Glu Pro Gly Asp Thr Val Phe Val Glu Val Ser Ala His Pro
            820                 825                 830
Val Leu Leu Pro Ala Ile Asp Gly Ala Thr Val Ala Thr Leu Arg Arg
        835                 840                 845
Gly Gly Gly Val His Arg Leu Leu Thr Ala Leu Ala Glu Ala His Thr
    850                 855                 860
Thr Gly Val Pro Val Asp Trp Ala Ala Val Pro Ala Thr Ala Thr
865                 870                 875                 880
Ala His Asp Leu Pro Thr Tyr Ala Phe His His Glu Arg Tyr Trp Ile
                885                 890                 895
Ser His Trp Leu Pro Ser Gly Glu Ala His Pro Arg Pro Ala Asp Asp
            900                 905                 910
Thr Glu Ser Gly Thr Gly Arg Thr Glu Ala Ser Pro Arg Pro His
        915                 920                 925
Asp
```

<210> SEQ ID NO 4
<211> LENGTH: 888
<212> TYPE: PRT
<213> ORGANISM: Saccharopolyspora erythraea

<400> SEQUENCE: 4

```
Met His Val Pro Gly Glu Glu Asn Gly Glu Pro Leu Ala Ile Val Gly
1               5                   10                  15
```

-continued

```
Met Ala Cys Arg Leu Pro Gly Gly Val Ala Ser Pro Glu Asp Leu Trp
             20                  25                  30
Arg Leu Leu Glu Ser Gly Gly Asp Gly Ile Thr Ala Phe Pro Thr Asp
             35                  40                  45
Arg Gly Trp Asp Val Asp Gly Leu Tyr Asp Pro Asp Pro Asp His Pro
 50                  55                  60
Gly Thr Ser Thr Val Arg His Gly Gly Phe Leu Ala Gly Val Ala Asp
 65                  70                  75                  80
Phe Asp Ala Ala Phe Phe Gly Ile Ser Pro Arg Glu Ala Leu Ala Met
                 85                  90                  95
Asp Pro Gln Gln Arg Leu Val Leu Glu Thr Ser Trp Glu Ala Leu Glu
                100                 105                 110
His Ala Gly Ile Leu Pro Glu Ser Leu Arg Gly Ser Asp Thr Gly Val
            115                 120                 125
Phe Met Gly Ala Phe Ser Asp Gly Tyr Gly Leu Gly Thr Asp Leu Gly
        130                 135                 140
Gly Phe Gly Ala Thr Gly Thr Gln Thr Ser Val Leu Ser Gly Arg Leu
145                 150                 155                 160
Ser Tyr Phe Tyr Gly Leu Glu Gly Pro Ala Val Thr Val Asp Thr Ala
                165                 170                 175
Cys Ser Ser Ser Leu Val Ala Leu His Gln Ala Gly Gln Ser Leu Arg
                180                 185                 190
Ser Gly Glu Cys Ser Leu Ala Leu Val Gly Gly Val Thr Val Met Ala
            195                 200                 205
Ser Pro Ser Gly Phe Val Glu Phe Ser Gln Gln Arg Gly Leu Ala Pro
        210                 215                 220
Asp Ala Arg Cys Lys Ala Phe Ala Asp Ala Ala Asp Gly Thr Gly Phe
225                 230                 235                 240
Ala Glu Gly Ser Gly Val Leu Ile Val Glu Arg Leu Ser Asp Ala Glu
                245                 250                 255
Arg Asn Gly His Arg Val Leu Ala Val Val Arg Gly Ser Ala Val Asn
                260                 265                 270
Gln Asp Gly Ala Ser Asn Gly Leu Ser Ala Pro Asn Gly Pro Ser Gln
            275                 280                 285
Glu Arg Val Ile Arg Gln Ala Leu Ala Asn Ala Gly Leu Thr Pro Ala
        290                 295                 300
Asp Val Asp Ala Val Glu Ala His Gly Thr Gly Thr Arg Leu Gly Asp
305                 310                 315                 320
Pro Ile Glu Ala Gln Ala Val Leu Ala Thr Tyr Gly Gln Gly Arg Asp
                325                 330                 335
Thr Pro Val Leu Leu Gly Ser Leu Lys Ser Asn Ile Gly His Thr Gln
            340                 345                 350
Ala Ala Ala Gly Val Ala Gly Val Ile Lys Met Val Leu Ala Met Arg
        355                 360                 365
His Gly Thr Leu Pro Arg Thr Leu His Val Asp Thr Pro Ser Ser His
    370                 375                 380
Val Asp Trp Thr Ala Gly Ala Val Glu Leu Leu Thr Asp Ala Arg Pro
385                 390                 395                 400
Trp Pro Glu Thr Asp Arg Pro Arg Arg Ala Gly Val Ser Ser Phe Gly
                405                 410                 415
Val Ser Gly Thr Asn Ala His Val Leu Leu Glu Ala His Pro Ala Gly
            420                 425                 430
```

-continued

```
Glu Pro Pro Ala Glu Pro Ser Ala Ser Lys Pro Gly Glu Pro Leu
            435                 440                 445

Ile Ala Thr Pro Leu Thr Pro Leu Pro Val Ser Ala Arg Thr Ala Thr
            450                 455                 460

Ala Leu Asp Gly Gln Val Arg Arg Leu Arg Glu His Leu Ala Ala Arg
465                     470                 475                 480

Pro Gly His Asp Pro Arg Ala Ile Ala Ala Gly Leu Leu Ala Arg Arg
                    485                 490                 495

Thr Thr Phe Pro His Arg Ala Val Leu Leu Asp Asp Val Val Thr
                500                 505                 510

Gly Thr Ala Leu Thr Glu Pro Arg Thr Val Phe Val Phe Pro Gly Gln
            515                 520                 525

Gly Pro Gln Trp Arg Gly Met Gly Val Glu Leu Met Ala Ala Ser Pro
            530                 535                 540

Val Phe Ala Ala Arg Met Arg Gln Cys Ala Asp Ala Leu Ile Pro His
545                 550                 555                 560

Thr Gly Trp Asp Pro Ile Ala Met Leu Asp Asp Pro Glu Val Thr Arg
                565                 570                 575

Arg Val Asp Val Val His Pro Val Cys Trp Ala Val Met Val Ser Leu
            580                 585                 590

Ala Ala Val Trp Glu Ala Ala Gly Val Arg Pro Asp Ala Val Ile Gly
            595                 600                 605

His Ser Gln Gly Glu Ile Ala Ala Ala Cys Val Ala Gly Ala Leu Thr
            610                 615                 620

Leu Glu Asp Gly Ala Arg Leu Val Ala Leu Arg Ser Val Leu Leu Leu
625                 630                 635                 640

Leu Arg Glu Leu Ala Gly Arg Gly Ala Met Gly Ser Val Ala Leu Pro
                    645                 650                 655

Ala Ala Asp Val Glu Ala Asp Ala Ala Arg Ile Asp Gly Val Trp Val
                660                 665                 670

Ala Gly Arg Asn Gly Ala Thr Thr Thr Thr Val Ala Gly Arg Pro Asp
            675                 680                 685

Ala Val Glu Thr Leu Ile Ala Asp Tyr Glu Ala Arg Gly Val Trp Val
            690                 695                 700

Arg Arg Ile Ala Val Asp Cys Pro Thr His Thr Pro Phe Val Asp Pro
705                 710                 715                 720

Leu Tyr Asp Glu Leu Gln Arg Ile Val Ala Asp Thr Thr Ser Arg Thr
                    725                 730                 735

Pro Glu Ile Pro Trp Phe Ser Thr Ala Asp Glu Arg Trp Ile Asp Ala
                740                 745                 750

Pro Leu Asp Asp Glu Tyr Trp Phe Arg Asn Met Arg His Pro Val Gly
            755                 760                 765

Phe Ala Thr Ala Val Thr Ala Ala Arg Glu Pro Gly Asp Thr Val Phe
            770                 775                 780

Val Glu Val Ser Ala His Pro Val Leu Leu Pro Ala Ile Asp Gly Ala
785                 790                 795                 800

Thr Val Ala Thr Leu Arg Arg Gly Gly Val His Arg Leu Leu Thr
                    805                 810                 815

Ala Leu Ala Glu Ala His Thr Thr Gly Val Pro Val Asp Trp Ala Ala
                820                 825                 830

Val Val Pro Ala Thr Ala Thr Ala His Asp Leu Pro Thr Tyr Ala Phe
            835                 840                 845

His His Glu Arg Tyr Trp Ile Ser His Trp Leu Pro Ser Gly Glu Ala
```

```
              850                 855                 860
His Pro Arg Pro Ala Asp Asp Thr Glu Ser Gly Thr Gly Arg Thr Glu
865                 870                 875                 880

Ala Ser Pro Pro Arg Pro His Asp
                885

<210> SEQ ID NO 5
<211> LENGTH: 888
<212> TYPE: PRT
<213> ORGANISM: Saccharopolyspora erythraea

<400> SEQUENCE: 5

Met His Val Pro Gly Glu Glu Asn Gly Glu Pro Leu Ala Ile Val Gly
  1               5                  10                  15

Met Ala Cys Arg Leu Pro Gly Gly Val Ala Ser Pro Glu Asp Leu Trp
                 20                  25                  30

Arg Leu Leu Glu Ser Gly Gly Asp Gly Ile Thr Ala Phe Pro Thr Asp
             35                  40                  45

Arg Gly Trp Asp Val Asp Gly Leu Tyr Asp Pro Asp Pro Asp His Pro
 50                  55                  60

Gly Thr Ser Thr Val Arg His Gly Gly Phe Leu Ala Gly Val Ala Asp
 65                  70                  75                  80

Phe Asp Ala Ala Phe Phe Gly Ile Ser Pro Arg Glu Ala Leu Ala Met
                 85                  90                  95

Asp Pro Gln Gln Arg Leu Val Leu Glu Thr Ser Trp Glu Ala Leu Glu
            100                 105                 110

His Ala Gly Ile Leu Pro Glu Ser Leu Arg Gly Ser Asp Thr Gly Val
            115                 120                 125

Phe Met Gly Ala Phe Ser Asp Gly Tyr Gly Leu Gly Thr Asp Leu Gly
130                 135                 140

Gly Phe Gly Ala Thr Gly Thr Gln Thr Ser Val Leu Ser Gly Arg Leu
145                 150                 155                 160

Ser Tyr Phe Tyr Gly Leu Glu Gly Pro Ala Val Thr Val Asp Thr Ala
                165                 170                 175

Gln Ser Ser Ser Leu Val Ala Leu His Gln Ala Gly Gln Ser Leu Arg
            180                 185                 190

Ser Gly Glu Cys Ser Leu Ala Leu Val Gly Gly Val Thr Val Met Ala
            195                 200                 205

Ser Pro Ser Gly Phe Val Glu Phe Ser Gln Gln Arg Gly Leu Ala Pro
        210                 215                 220

Asp Ala Arg Cys Lys Ala Phe Ala Asp Ala Ala Asp Gly Thr Gly Phe
225                 230                 235                 240

Ala Glu Gly Ser Gly Val Leu Ile Val Glu Arg Leu Ser Asp Ala Glu
                245                 250                 255

Arg Asn Gly His Arg Val Leu Ala Val Val Arg Gly Ser Ala Val Asn
            260                 265                 270

Gln Asp Gly Ala Ser Asn Gly Leu Ser Ala Pro Asn Gly Pro Ser Gln
        275                 280                 285

Glu Arg Val Ile Arg Gln Ala Leu Ala Asn Ala Gly Leu Thr Pro Ala
    290                 295                 300

Asp Val Asp Ala Val Glu Ala His Gly Thr Gly Thr Arg Leu Gly Asp
305                 310                 315                 320

Pro Ile Glu Ala Gln Ala Val Leu Ala Thr Tyr Gly Gln Gly Arg Asp
                325                 330                 335
```

-continued

```
Thr Pro Val Leu Leu Gly Ser Leu Lys Ser Asn Ile Gly His Thr Gln
        340                 345                 350
Ala Ala Ala Gly Val Ala Gly Val Ile Lys Met Val Leu Ala Met Arg
        355                 360                 365
His Gly Thr Leu Pro Arg Thr Leu His Val Asp Thr Pro Ser Ser His
        370                 375                 380
Val Asp Trp Thr Ala Gly Ala Val Glu Leu Leu Thr Asp Ala Arg Pro
385                 390                 395                 400
Trp Pro Glu Thr Asp Arg Pro Arg Ala Gly Val Ser Ser Phe Gly
                    405                 410                 415
Val Ser Gly Thr Asn Ala His Val Leu Leu Glu Ala His Pro Ala Gly
                    420                 425                 430
Glu Pro Pro Ala Glu Glu Pro Ser Ala Ser Lys Pro Gly Glu Pro Leu
            435                 440                 445
Ile Ala Thr Pro Leu Thr Pro Leu Pro Val Ser Ala Arg Thr Ala Thr
            450                 455                 460
Ala Leu Asp Gly Gln Val Arg Arg Leu Arg Glu His Leu Ala Ala Arg
465                 470                 475                 480
Pro Gly His Asp Pro Arg Ala Ile Ala Ala Gly Leu Leu Ala Arg Arg
                    485                 490                 495
Thr Thr Phe Pro His Arg Ala Val Leu Leu Asp Asp Val Val Thr
                    500                 505                 510
Gly Thr Ala Leu Thr Glu Pro Arg Thr Val Phe Val Phe Pro Gly Gln
            515                 520                 525
Gly Pro Gln Trp Arg Gly Met Gly Val Glu Leu Met Ala Ala Ser Pro
            530                 535                 540
Val Phe Ala Ala Arg Met Arg Gln Cys Ala Asp Ala Leu Ile Pro His
545                 550                 555                 560
Thr Gly Trp Asp Pro Ile Ala Met Leu Asp Asp Pro Glu Val Thr Arg
                    565                 570                 575
Arg Val Asp Val Val His Pro Val Cys Trp Ala Val Met Val Ser Leu
                    580                 585                 590
Ala Ala Val Trp Glu Ala Ala Gly Val Arg Pro Asp Ala Val Ile Gly
            595                 600                 605
His Ser Gln Gly Glu Ile Ala Ala Ala Cys Val Ala Gly Ala Leu Thr
            610                 615                 620
Leu Glu Asp Gly Ala Arg Leu Val Ala Leu Arg Ser Val Leu Leu Leu
625                 630                 635                 640
Leu Arg Glu Leu Ala Gly Arg Gly Ala Met Gly Ser Val Ala Leu Pro
                    645                 650                 655
Ala Ala Asp Val Glu Ala Asp Ala Ala Arg Ile Asp Gly Val Trp Val
                    660                 665                 670
Ala Gly Arg Asn Gly Ala Thr Thr Thr Val Ala Gly Arg Pro Asp
            675                 680                 685
Ala Val Glu Thr Leu Ile Ala Asp Tyr Glu Ala Arg Gly Val Trp Val
            690                 695                 700
Arg Arg Ile Ala Val Asp Cys Pro Thr His Thr Pro Phe Val Asp Pro
705                 710                 715                 720
Leu Tyr Asp Glu Leu Gln Arg Ile Val Ala Asp Thr Thr Ser Arg Thr
                    725                 730                 735
Pro Glu Ile Pro Trp Phe Ser Thr Ala Asp Glu Arg Trp Ile Asp Ala
            740                 745                 750
Pro Leu Asp Asp Glu Tyr Trp Phe Arg Asn Met Arg His Pro Val Gly
```

```
                    755                     760                     765
Phe Ala Thr Ala Val Thr Ala Ala Arg Glu Pro Gly Asp Thr Val Phe
    770                     775                     780

Val Glu Val Ser Ala His Pro Val Leu Leu Pro Ala Ile Asp Gly Ala
785                     790                     795                     800

Thr Val Ala Thr Leu Arg Arg Gly Gly Gly Val His Arg Leu Leu Thr
                    805                     810                     815

Ala Leu Ala Glu Ala His Thr Thr Gly Val Pro Val Asp Trp Ala Ala
                820                     825                     830

Val Val Pro Ala Thr Ala Thr Ala His Asp Leu Pro Thr Tyr Ala Phe
        835                     840                     845

His His Glu Arg Tyr Trp Ile Ser His Trp Leu Pro Ser Gly Glu Ala
        850                     855                     860

His Pro Arg Pro Ala Asp Asp Thr Glu Ser Gly Thr Gly Arg Thr Glu
865                     870                     875                     880

Ala Ser Pro Pro Arg Pro His Asp
                885
```